US009868786B2

(12) United States Patent
Finkelman et al.

(10) Patent No.: US 9,868,786 B2
(45) Date of Patent: Jan. 16, 2018

(54) METHODS FOR SUPPRESSING ALLERGIC REACTIONS

(75) Inventors: Fred D. Finkelman, Cincinnati, OH (US); Marat V. Khodoun, Cincinnati, OH (US); Durga Krishnamurthy, Cincinnati, OH (US); Richard T. Strait, Mason, OH (US); Zeynep (Yesim) Kucuk, Cincinnati, OH (US)

(73) Assignees: University of Cincinnati, Cincinnati, OH (US); Children's Hospital Medical Center, Cincinnati, OH (US); U.S. Department of Veterans Affairs, Washington, DC (US); Medizinische Universität Wien, Vienna (AT)

( * ) Notice: Subject to any disclaimer, the term of this patent is extended or adjusted under 35 U.S.C. 154(b) by 255 days.

(21) Appl. No.: 14/111,208

(22) PCT Filed: Apr. 12, 2012

(86) PCT No.: PCT/US2012/033319
§ 371 (c)(1),
(2), (4) Date: Feb. 25, 2014

(87) PCT Pub. No.: WO2012/142286
PCT Pub. Date: Oct. 18, 2012

(65) Prior Publication Data
US 2014/0314783 A1    Oct. 23, 2014

Related U.S. Application Data

(60) Provisional application No. 61/474,566, filed on Apr. 12, 2011.

(51) Int. Cl.
| | | |
|---|---|---|
| A61K 39/395 | (2006.01) | |
| C07K 16/00 | (2006.01) | |
| C12P 21/08 | (2006.01) | |
| C07K 16/28 | (2006.01) | |
| A61K 45/06 | (2006.01) | |
| C07K 16/42 | (2006.01) | |
| A61K 39/00 | (2006.01) | |

(52) U.S. Cl.
CPC ........ C07K 16/283 (2013.01); A61K 39/3955 (2013.01); A61K 45/06 (2013.01); C07K 16/4291 (2013.01); A61K 2039/505 (2013.01); A61K 2039/507 (2013.01); A61K 2039/545 (2013.01)

(58) Field of Classification Search
None
See application file for complete search history.

(56) References Cited

U.S. PATENT DOCUMENTS

| | | | | |
|---|---|---|---|---|
| 6,165,799 A * | 12/2000 | Kinet | ................. | G01N 33/6854 435/29 |
| 6,488,937 B1 | 12/2002 | Smits | | |
| 7,384,633 B2 * | 6/2008 | Sugimura | ............ | C07K 16/283 424/133.1 |
| 7,655,229 B2 * | 2/2010 | Chan | ..................... | C07K 16/283 424/136.1 |
| 7,662,926 B2 | 2/2010 | Chan et al. | | |
| 7,879,334 B1 | 2/2011 | Saxon et al. | | |
| 8,968,738 B2 * | 3/2015 | Mitre | ................... | C07K 16/283 424/133.1 |
| 2005/0175638 A1 | 8/2005 | Esch | | |
| 2010/0158898 A1 | 6/2010 | Liu et al. | | |

OTHER PUBLICATIONS

Bakema et al. 'The human immunoglobulin A Fc receptor FcalphaRI:a multifaceted regulator of mucosal immunity.' Mucosal Immunity 4(6);612-624, 2011.*
Tang ML, Osborne N, Allen K; Epidemiology of Anaphyliaxis. Curr Opin Allergy Clin Immunol. Aug. 2009; 9(4): 351-6.
Decker WW, Campbell RL, Manivannan V et al, The etiology and incidence of anaphylaxis in Rochester, Minnesota; a report from the Rochester Epidemiology Project. J Allergy Clin Immunol 2008; 122:1161-1165.
Liew WK, Williamson, E., Tang ML; Anaphylaxis fatalities and admissions in Australia; J Allergy Clin Immunol 2008;123:434-442.
Rafi A, Doo LT et al.; Effects of omalizumab in patients with food allergy. Allergy Asthma Proc. Jan. 2010; 31(1) 76-83.
Trevor T. Hansel, et al. The safe and side effects of monoclonal antibodies. Nat Rev Drug Discov. Apr. 2010; 9(4):325-338. ePub 2010 Mar 22, 2010.
Mirkina et al, "Inhibition of human cord-blood-derived mast cell responses by anti-Fc epison R1mAB 15/1 versus anti-IgE Omalizaumab"; Immunology Letters 109 (2007) 120-128.
Zuber D. Mulla, et al., "Anaphylaxis in Olmsted County: Seasonal pattern and suggestions for epidemiologic analysis"; Letter to the Editor; J Allergy Clin Immunol May 2009, p. 1194.

* cited by examiner

*Primary Examiner* — Nora Rooney
(74) *Attorney, Agent, or Firm* — Dinsmore & Shohl LLP

(57) ABSTRACT

Provided are methods for suppressing IgE and IgG-mediated allergic reactions through monoclonal antibody applications. More specifically, methods are herein provided for safe induction of rapid desensitization. Specific embodiments are herein provided for suppressing allergic reactions in a subject, including specific methods of providing a monoclonal antibody selected from the group consisting of anti-FcεRIa and anti-FcγRIIb / RIII; administering the antibody to a subject at a dose that is lower than the level required to induce shock; and administering sequentially escalating doses of the monoclonal antibody so as to induce rapid desensitization to an allergen, thereby suppressing allergic reaction in the subject.

17 Claims, 70 Drawing Sheets

Flow cytometric analysis for mast cell hamster IgG or mouse IgE

Flow cytometric analysis for mast cell hamster IgG or mouse IgE

MK-512 Mice were injected serially with doubling doses of MAR-1 or control mAb, from 100 ng to 25.6 μg at 1.5 hr intervals. Mice received biotin-aIL-4 15 min before 1st dose and were bled 1.5 hr after last dose.

MK-601 Mice were injected with saline or were desensitized with progressive doses of MAR-1 (50 ng, 100 ng, 200 ng, 400 ng, 800 ng, 1.6 µg, 3.2 µg, 6.4 µg, 12.8 µg, 25.6 µg; then, 2 hr later challenged with 100 µg of anti IgE mAb.

MK-509 Mice were injected serially with doubling doses of MAR-1 or control mAb, from 50 ng to 25.6 μg at 2 hr intervals. Mice were injected with 10 μg of IgE anti TNP at the same time as the 25.6 μg dose of MAR-1 or control mAb and challenged with TNP-OVA 7 hr later and injected with anti-IL-4 mAb and 100 μg of EM-95 70 hr after that (along with anti IL-4 mAb) and bled later.

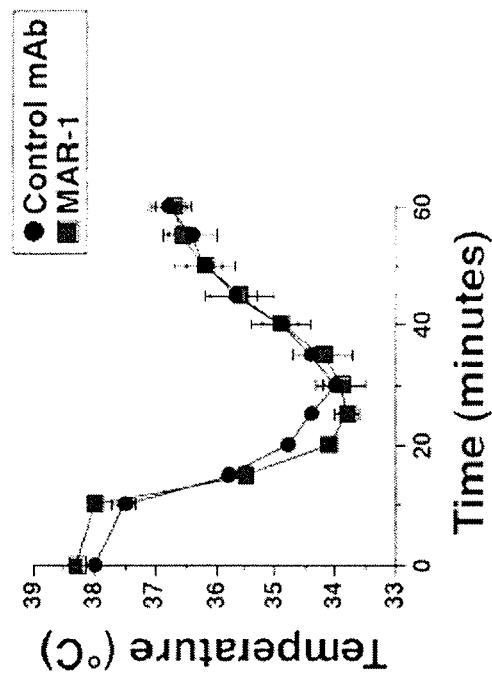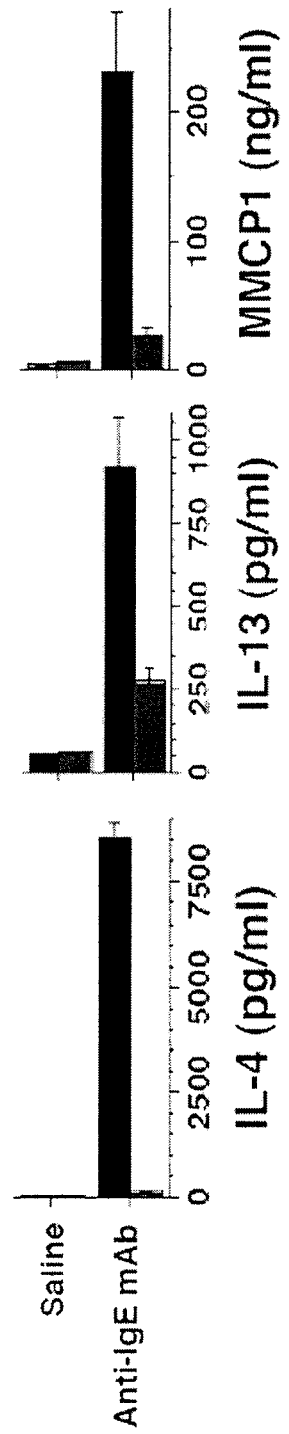
FIG. 28A
FIG. 28B
FIG. 28C
FIG. 28D

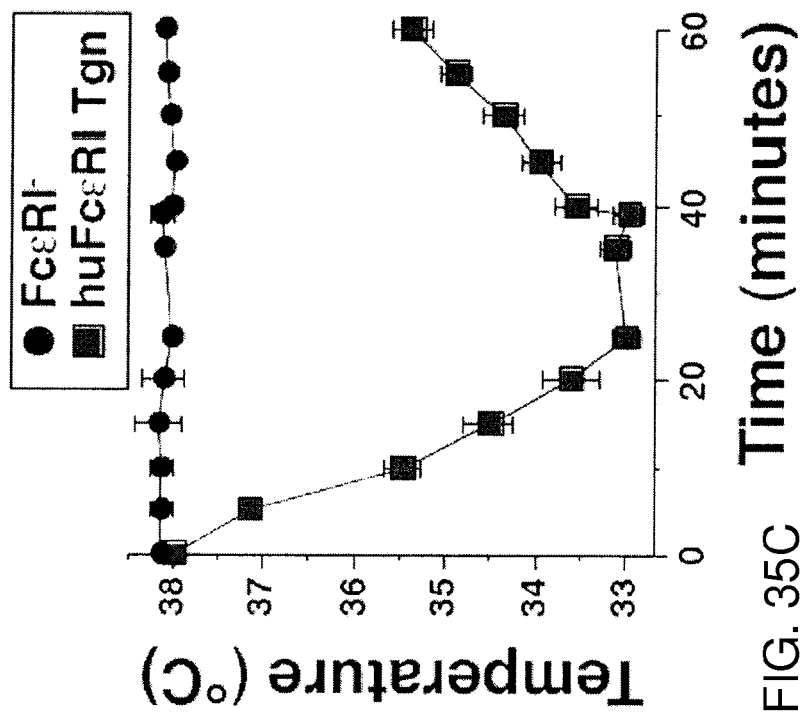
FIG. 35C
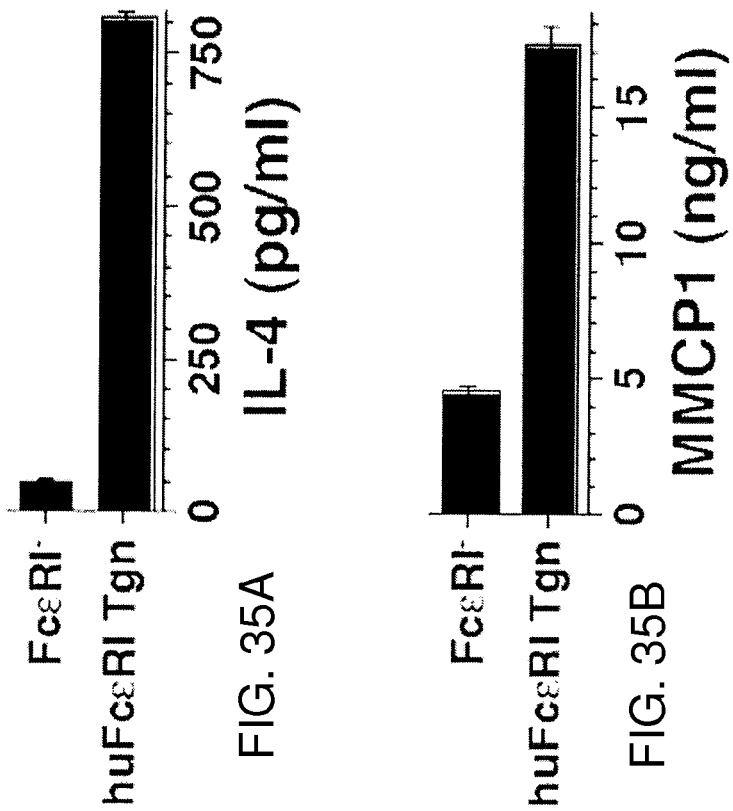
FIG. 35A
FIG. 35B

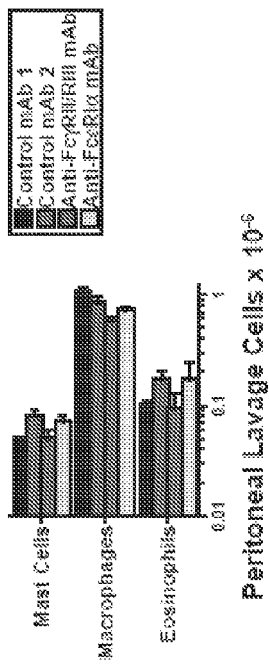
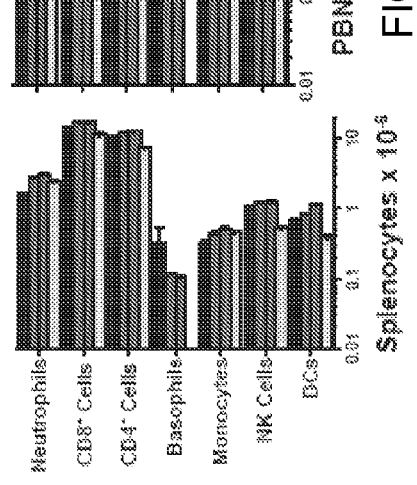
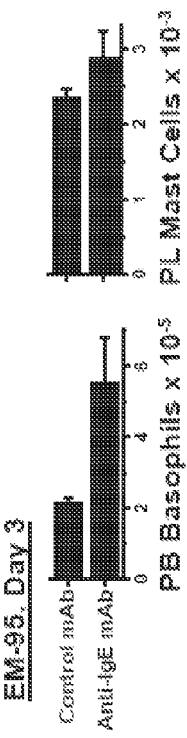
FIG. 53 B
FIG. 53 C

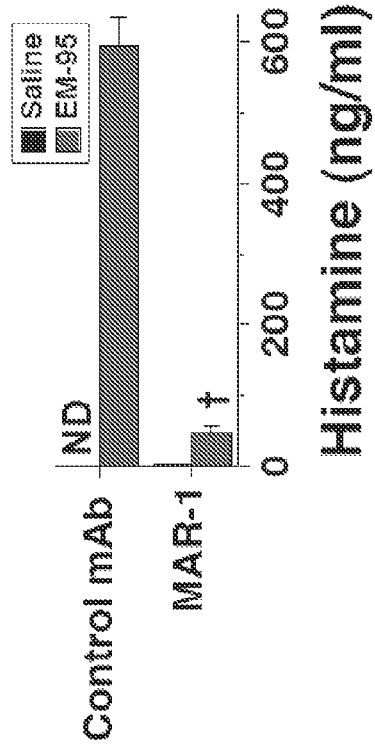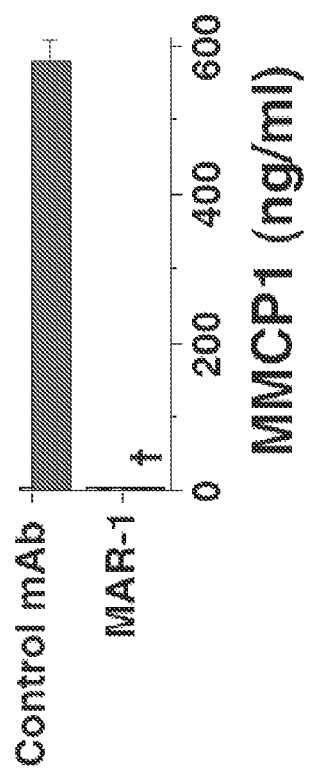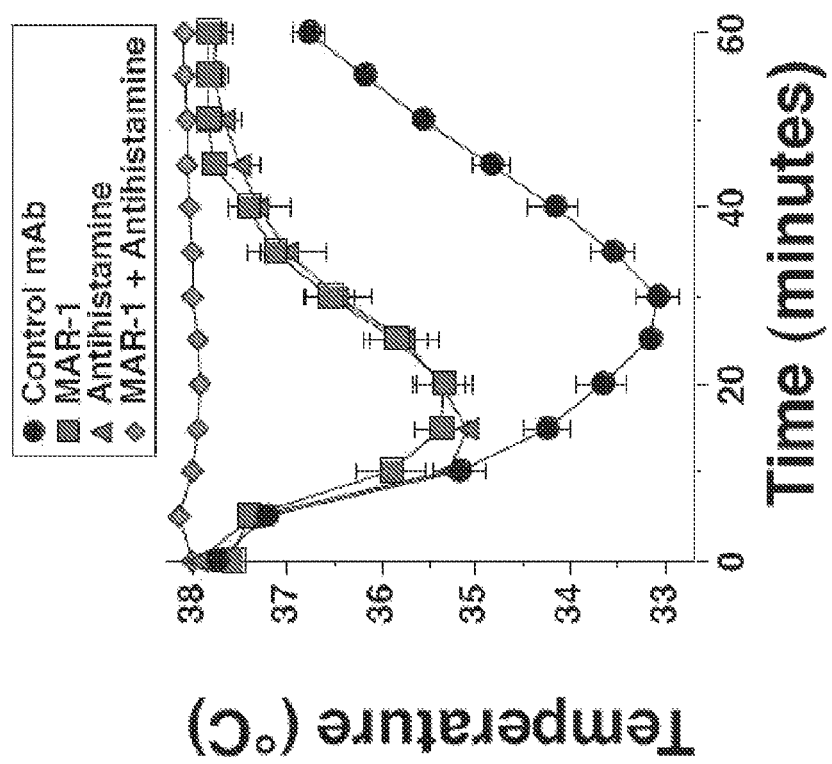

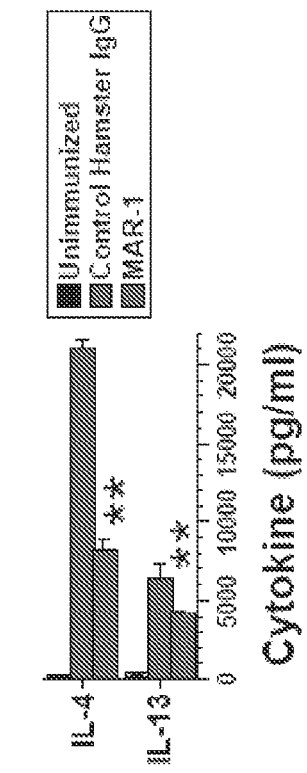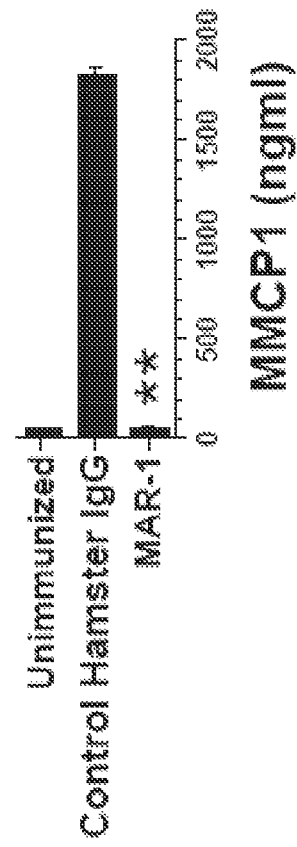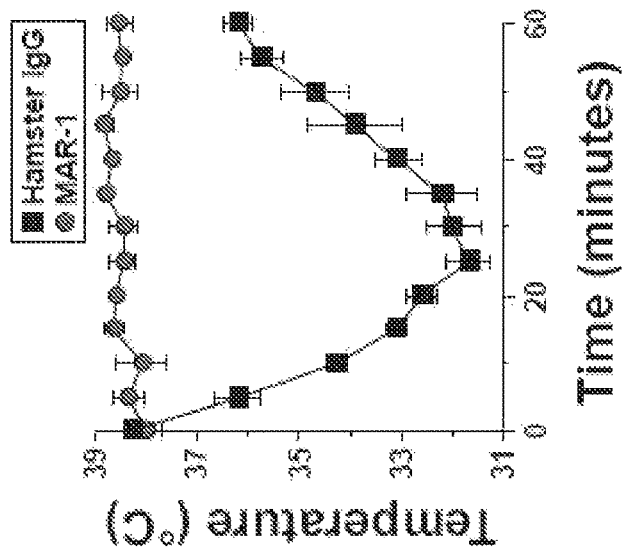
FIG. 61B
FIG. 61C
FIG. 61A

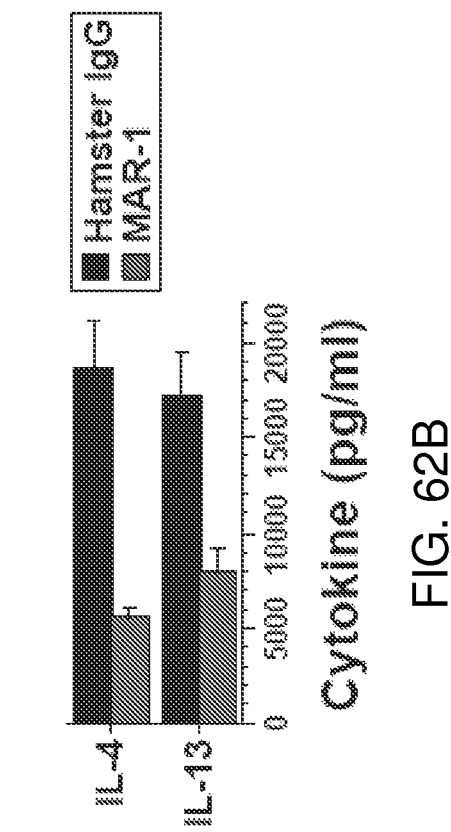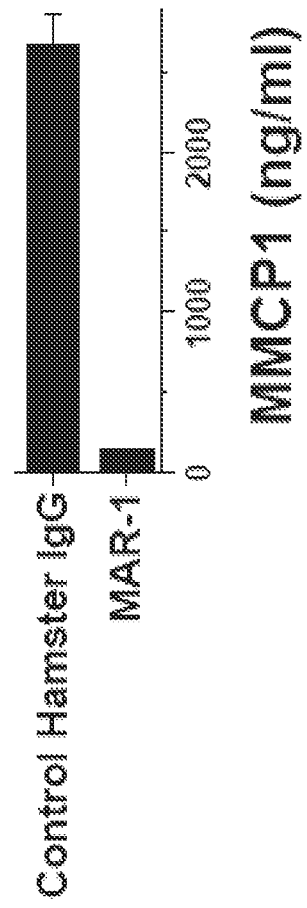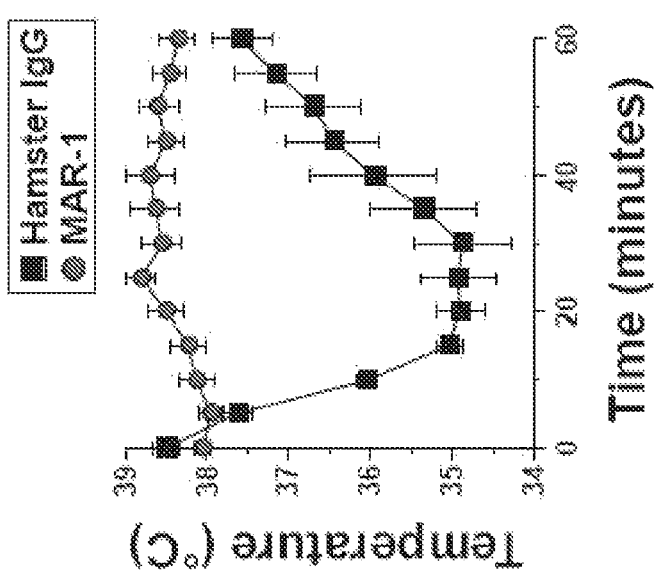
FIG. 62B
FIG. 62C
FIG. 62A

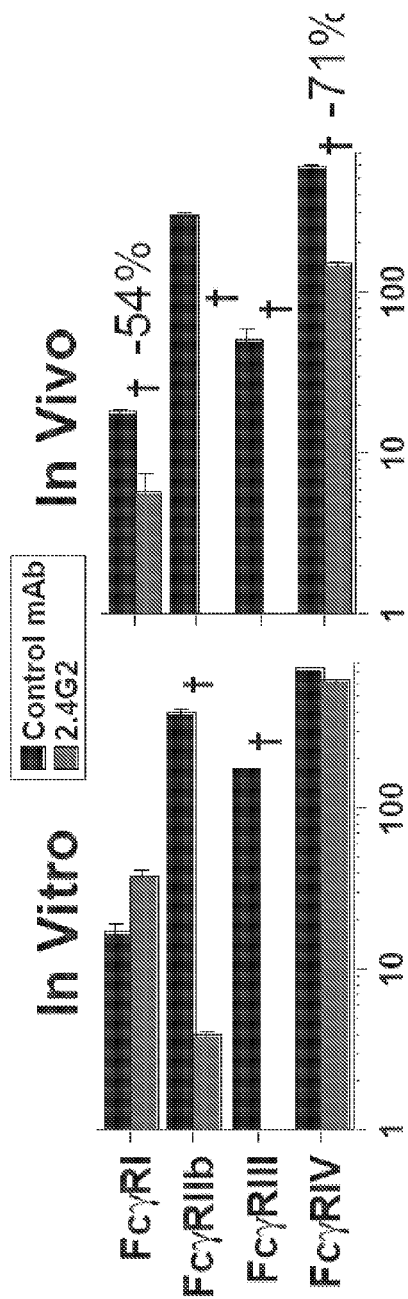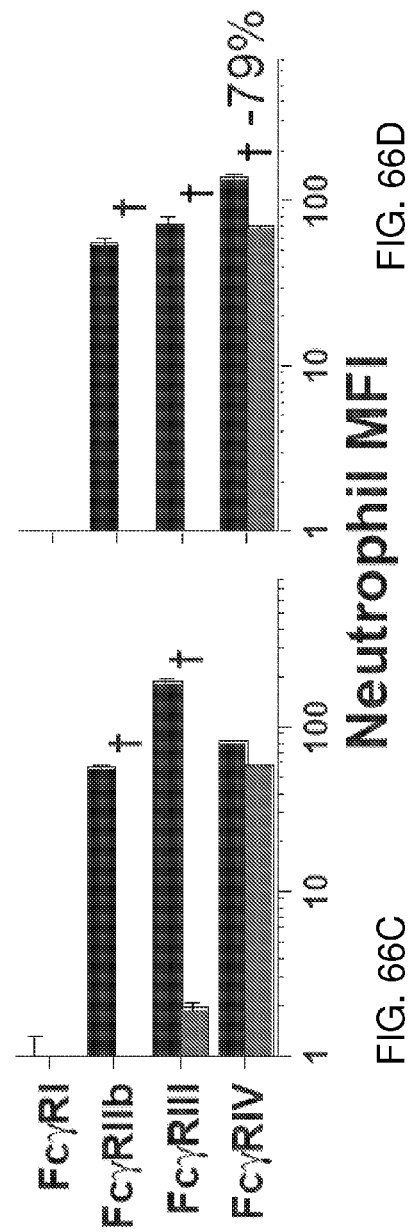
FIG. 66A
FIG. 66B
FIG. 66C
FIG. 66D

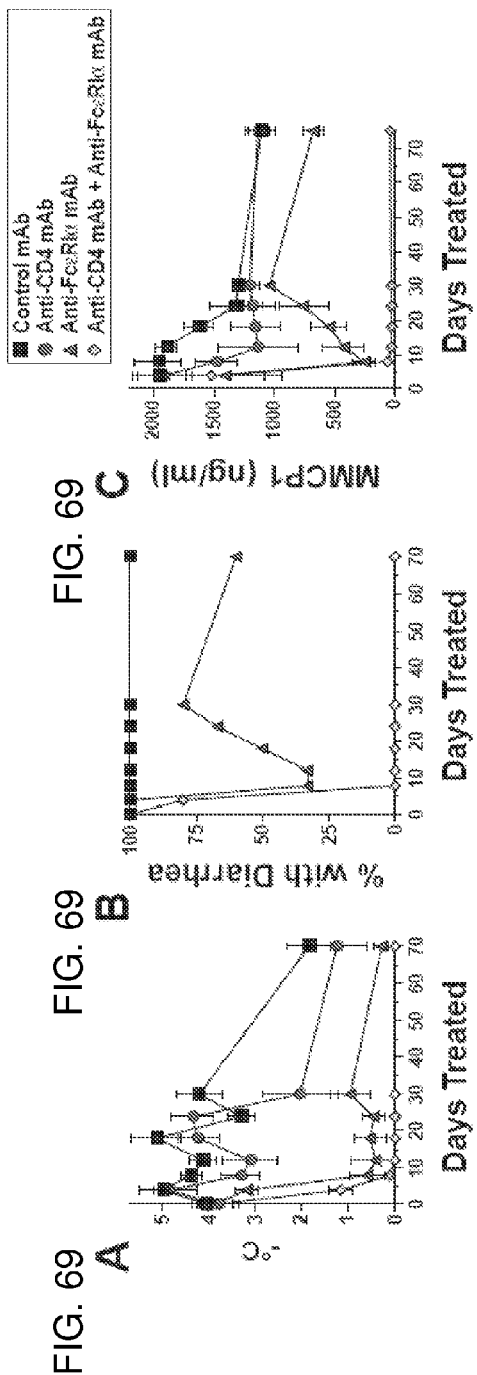
FIG. 69 A
FIG. 69 B
FIG. 69 C
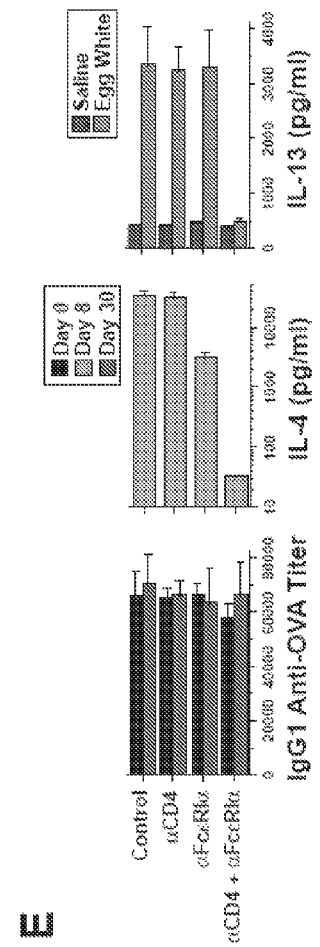
FIG. 69 E
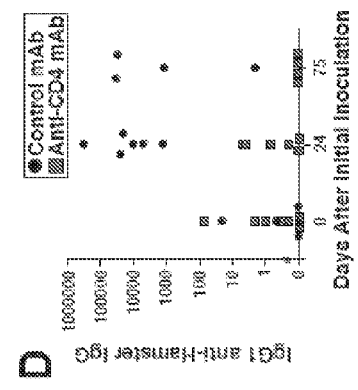
FIG. 69 D

METHODS FOR SUPPRESSING ALLERGIC REACTIONS

CROSS REFERENCE TO RELATED APPLICATIONS

This application claims benefit to U.S. Provisional Application Ser. No. 61/474,566, filed Apr. 12, 2011, and International Application Serial No. PCT/US2012/033319, filed on Apr. 12, 2012, which are incorporated by reference herein in their entirety.

TECHNICAL FIELD

Provided are methods for suppressing IgE- and IgG-mediated allergic reactions through monoclonal antibody applications. More specifically, methods are herein provided for safe induction of rapid desensitization.

BACKGROUND OF THE INVENTION

Allergic disorders, including allergic rhinitis, asthma, atopic dermatitis, food allergy and anaphylaxis are an increasingly common cause of morbidity in developed countries and, in the case of asthma and anaphylaxis, a not infrequent cause of death. All of these disorders are mediated, to some extent, by immediate hypersensitivity reactions in which the activation of inflammatory cells by the crosslinking of immunoglobulin (Ig) Fc receptors (R) leads rapidly to the release of vasoactive mediators, such as histamine and platelet activating factor (PAF), cytokines and proteolytic enzymes. Such immediate hypersensitivity reactions are the critical pathogenic mechanism in anaphylaxis and IgE-mediated food allergy and an important contributing mechanism in asthma, atopic dermatitis and allergic rhinitis. In both humans and mice, immediate hypersensitivity reactions can be mediated by antigen crosslinking of antigen-specific IgE bound to the high affinity IgE receptor, FcεRI, on mast cells and basophils, while the crosslinking of FcγRIII or FcγRIV on macrophages, neutrophils, and/or basophils by IgG/antigen complexes can mediate immediate hypersensitivity in mice and possibly also in humans.

Although some of these allergic disorders can be treated pharmacologically, manipulation of the immune system by administering increasing doses of allergen over time can also be an efficacious, albeit sometimes risky, way to suppress disease. Two different general strategies of allergen immunotherapy have been widely used. Standard immune desensitization involves administration of increasing doses of allergen through a subcutaneous, oral, rectal or sublingual route over a period of weeks to months. This procedure suppresses IgE-mediated disease through at least two mechanisms: 1) increased production of IgG antibodies that can activate an inhibitory Ig receptor, FcγRIIb, and intercept antigen before it can access mast cell and basophil IgE; and 2) induction of regulatory T cells, that can suppress production of IgE. Rapid desensitization procedures, in contrast, administer increasing concentrations of allergen over a period of hours or days. This time period is too short to work by altering Ig production; however, the precise mechanisms are not established. Unlike conventional desensitization, the suppressive effects of rapid desensitization can be quickly lost when allergen administration is discontinued.

To date, rapid desensitization techniques have always involved the administration of allergen. Although effective, this can be of limited utility in individuals who are allergic to multiple antigens. In addition, the presence of serum antibodies, including IgG, which can bind inoculated allergens, may make rapid desensitization more risky if the initial, small allergen doses are neutralized before they can access mast cell or basophil bound IgE, so that the first dose of allergen that interacts with cell-bound IgE is sufficiently large to induce a severe reaction. It has now been found that although administration of a single large dose of the anti-FcεRIα mAb, MAR-1, the anti-IgE mAb, EM-95, or the anti-FcγRIIb/RIII mAb, 2.4G2, can induce an anaphylactic response, administration of sequentially increasing doses of any of these mAbs, starting with a dose too small to induce detectable disease, as in rapid desensitization with allergen, inhibits IgE- or IgG-mediated immediate hypersensitivity. The results of these studies in a mouse model demonstrate the feasibility of this approach.

These and additional objects, embodiments, and aspects of the invention will become apparent by reference to the Figures and Detailed Description below.

SUMMARY

Specific embodiments of the invention provide for a method of suppressing allergic reactions in a subject, the method comprising: providing a monoclonal antibody selected from the group consisting of anti-FcεRIa and anti-FcγRIIb/RIII; administering the antibody to a subject at a dose that is lower than the level required to induce shock; and administering sequentially escalating doses of the monoclonal antibody so as to induce rapid desensitization to an allergen thereby suppressing allergic reaction in the subject.

BRIEF DESCRIPTION OF THE FIGURES

FIG. 28 A-D shows that treatment with MAR-1 for 2-3 days inhibits anti-IgE mAB-induced IL-4 (B) MMCP1 (D) and IL-13 (C) responses, but not anaphylaxis (A).

FIGS. 35A-C show graphs of studies with a model planned to determine whether anti-human FcεRI mABs can be used for desensitization, and more specifically show that anti-human FcεRI mAB induces IL-4 and MMCP1 responses and anaphylaxis in human IgE-primed huFcεRI transgenic mice.

FIGS. 53A-C show that rapid desensitization with MAR-1 anti-FcεRIα monoclonal antibody causes loss of basophils, but not other cell types.

FIGS. 58A-C are graphs showing that anaphylaxis induced by anti-IgE monoclonal antibody after long-term treatment with MAR-1 anti-FcεRIα monoclonal antibody is still histamine-mediated.

FIGS. 61A-C are graphs showing that MAR-1 anti-FcεRIα monoclonal antibody blocks IgE mediated anaphylaxis in mice actively immunized with goat anti-mouse IgD antibody (GaMD).

FIG. 62A-C are graphs showing that treatment with MAR-1 anti-FcεRIα monoclonal antibody suppresses IgE mediated anaphylaxis in mice actively sensitized with ovalbumin (OVA).

FIGS. 66A-D show that 2.4G2 anti-FcγRII/RIII monoclonal antibody does not block binding of FcγRIV mAB but decreases neutrophil and monocyte expression of these receptors.

FIG. 69A-E are graphs showing that MAR-1 hamster IgG anti-mouse FcεRIα mAB and GK1.5 rat IgG anti-mouse CD4 mAB synergistically suppress established IgE-mediated anaphylaxis that is triggered by antigen ingestion.

DETAILED DESCRIPTION

Figures 1A, 1B:
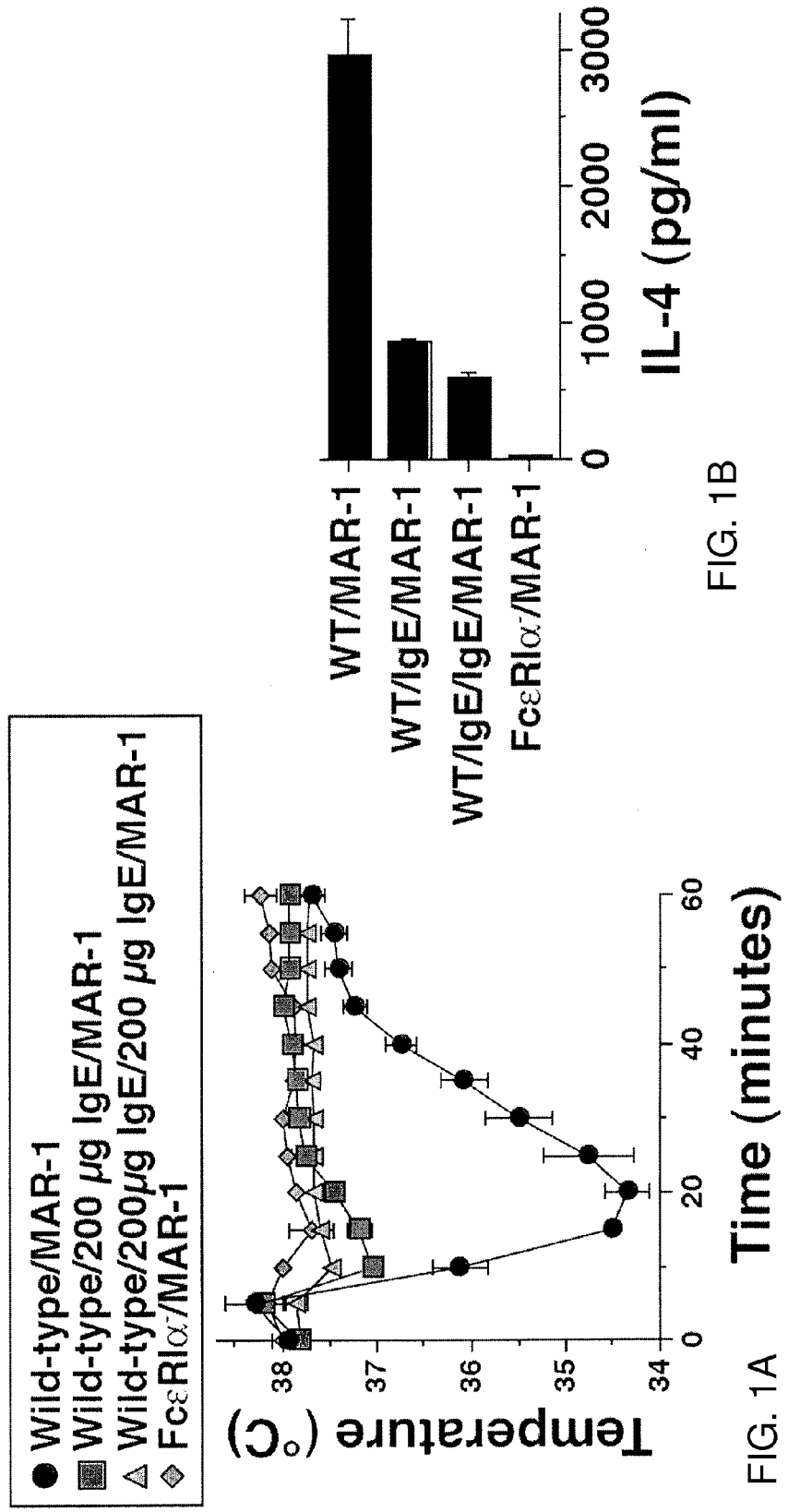
FIGS. 1A-B show in vivo saturation of FcεRI with IgE suppresses the anaphylactic response to MAR-1.

The present invention will now be described with occasional reference to the specific non-limiting embodiments of the invention. This invention may, however, be embodied in different forms and should not be construed as limited to the embodiments set forth herein. Rather, these embodiments are provided so that this disclosure will be thorough and complete, and to fully convey the scope of the invention to those skilled in the art.

Unless otherwise defined, all technical and scientific terms used herein have the same meaning as commonly understood by one of ordinary skill in the art to which this invention pertains. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

As used herein, the term rapid desensitization refers to rapid desensitization to an allergen; rapid desensitization is accomplished by administering increasing concentrations of allergen over a period of hours or days. The administration in certain embodiments can be from two to ten administrations or more over a period of an hour to several days (24 hours, two or three days or more). The doses can be provided at intervals such as 30 minutes, 60 minutes, or 90 minutes or more (or a combination of the times). Rapid desensitization is contrasted with standard immune desensitization that involves administration of increasing doses of allergen through a subcutaneous, oral, rectal or sublingual route over a period of weeks to months.

As used herein, the term sequentially escalating refers to two or more doses, such as doses provided in inducing rapid desensitization, wherein the second dose is greater than the first, the third is greater than the second, and so forth proceeding through all of the injections (the subsequent injection is always greater than the prior). Each subsequent dose can be larger by a determined amount or can be characterized in relation to the first dose or the immediately preceeding dose (such as each subsequent dose is doubled or tripled in relation to the first dose or in relation to the immediately preceeding dose).

As used herein, the term shock can refer to a clinical diagnosis or standard or can refer to signs such as a change in a subject's temperature following an administration of immunoglobulin or during the course or desensitization. Other factors could include changes in circulatory function, pallor, sweating, weak pulse, and very low blood pressure.

As used herein, the term allergen refers to a substance that produces an immune response; such responses can include hypersensitivities and allergies. The allergen can, for example, be a protein, can be from food (such as peanut butter or strawberries) or can be from the environmental surroundings. Allergens may be naturally occurring or of synthetic origin and include among other things pollen, mold spores, dust, animal dander, insect debris, foods, blood serum, and drugs (including cosmetics).

As used herein, the term administering refers to introducing a substance to a subject; this can be through, among other ways, known clinical techniques; non-limiting examples include intravenously, orally, subcutaneously, intraperitoneally, or intramuscularly; and can be in known clinical forms; non-limiting examples include pills, inhalants or injectables (among others).

Anaphylaxis is the most severe form of allergic reaction and, if untreated, can result in death. Around 1% of allergic reactions are severe (Tang M L, Osborne N, Allen K., Epidemiology of anaphylaxis. Curr Opin Allergy Clin Immunol. 2009 August; 9(4): 351-6). Prevalence of anaphylaxis is relatively high in the United States as compared to other developed countries (per 100,000 person-years: USA—49.8; Australia—13; UK—8.4) and has more than doubled in the last two decades. Rates of death from drug induced anaphylaxis have risen in some countries by 300% over the last decade. (Decker W W, Campbell R L, Manivannan V, et al. The etiology and incidence of anaphylaxis in Rochester, Minn.: a report from the Rochester Epidemiology Project. J Allergy Clin Immunol 2008; 122:1161-1165. Liew W K, Williamson E., Tang M L, Anaphylaxis fatalities and admissions in Australia. J Allergy Clin Immunol 2008; 123:434-442). Many cases of the food-, insect-, and drug-related cases of anaphylaxis are associated with elevated IgE level. (Rafi A, Do L T, et al. Effects of omalizumab in patients with food allergy. Allergy Asthma Proc. 2010 January; 31(1) 76-83).

I. Pathways of Anaphylaxis

Figure 3:
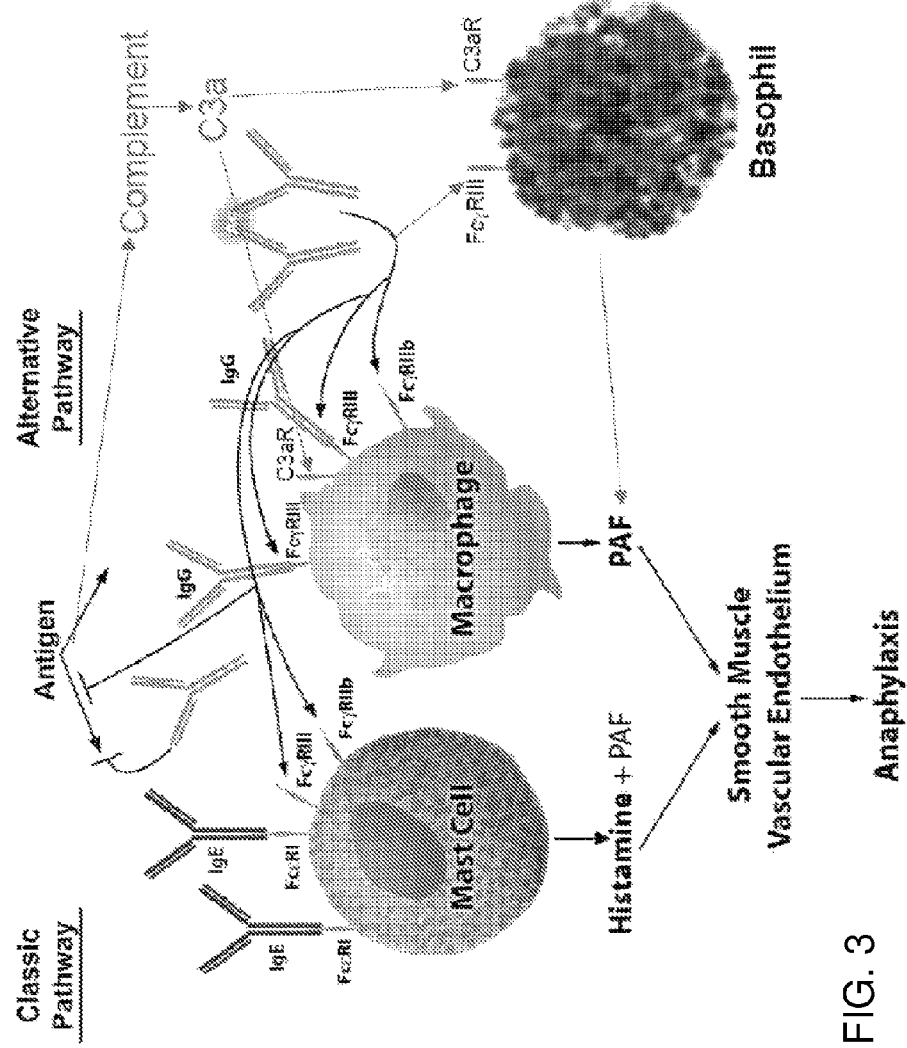
FIG. 3 depicts pathways of anaphylaxis.
Figure 4:
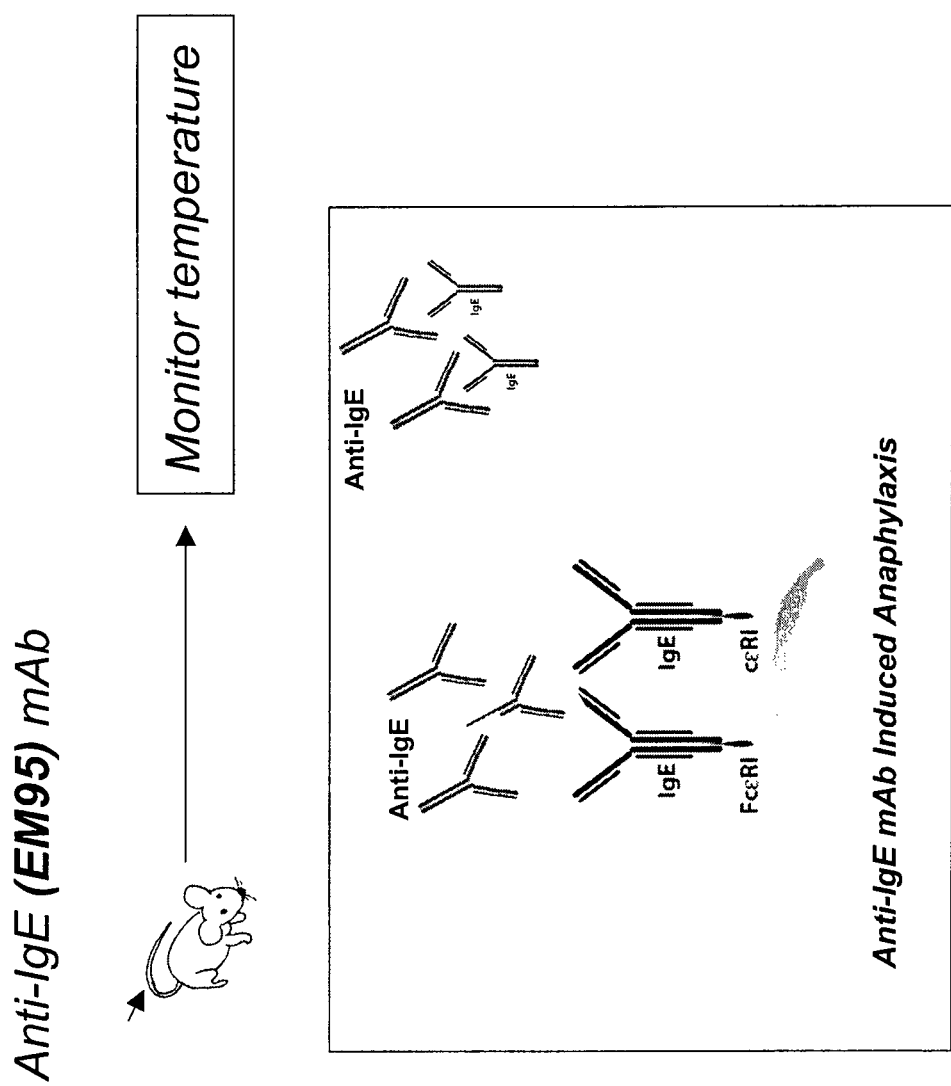
FIG. 4 shows model 1 of mouse passive anaphylaxis.
Figure 5:
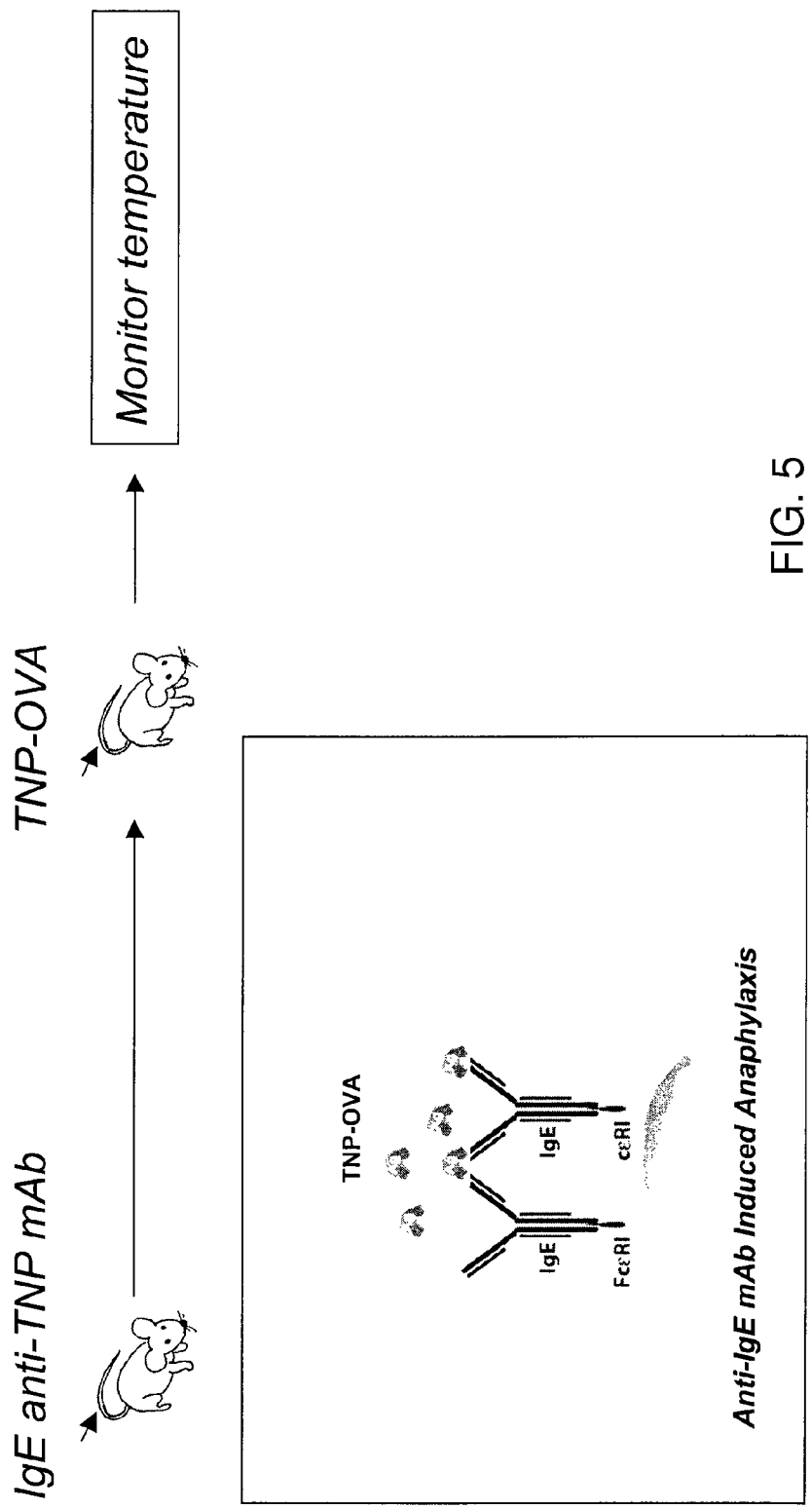
FIG. 5 shows model 2 of mouse passive anaphylaxis.

To study and interpret studies of anaphylaxis it is important to understand the pathways, mechanisms, and clinical implications of anaphylaxis. FIGS. 3-5 show pathways of anaphylaxis (FIG. 3) along with two models of passive anaphylaxis (FIGS. 4-5). As to clinical implications, for example, Omalizumab (Xolair), a humanized monoclonal antibody that binds to serum, but not FcεRI-bound IgE, is an effective treatment for food allergy, asthma, uticaria, angiodema, and atopic dermatitis (Rafi A, Do L T, et al Effects of omalizumab in patients with food allergy. Allergy Asthma Proc. 2010 January; 31(1):76-8).

Side effects of omalizumab therapy include anaphylaxis (0.1% of treated patients), skin reaction, etc. Anaphylaxis has occurred as early as after the first dose of Xolair, but also has occurred beyond 1 year after beginning regularly administered treatment (Thomas Singer, Jane A. Mitchell and Andrew J. T. George The safety and side effects of monoclonal antibodies. Trever T. Hansel, Harold Kropshofer, Nat Rev Drug Discov. 2010 April; 9(4):325-38. Epub 2010 Mar. 22).

Omalizumab cannot be used for individuals who have the highest serum IgE levels and has no direct effects on FcεRI-bound IgE.

Treatment with anti-FcεRI (MAR-1) mAB may inhibit IgE-dependent anaphylaxis, either by desensitizing mast cells or by blocking their ability to bind IgE (removing FcεRI from the mast cell surface and/or blocking its IgE-binding site).

II. Results and Discussion of Selected Data

Rapid Desensitization with an Activating Anti-IgE mAb

Figure 36A:
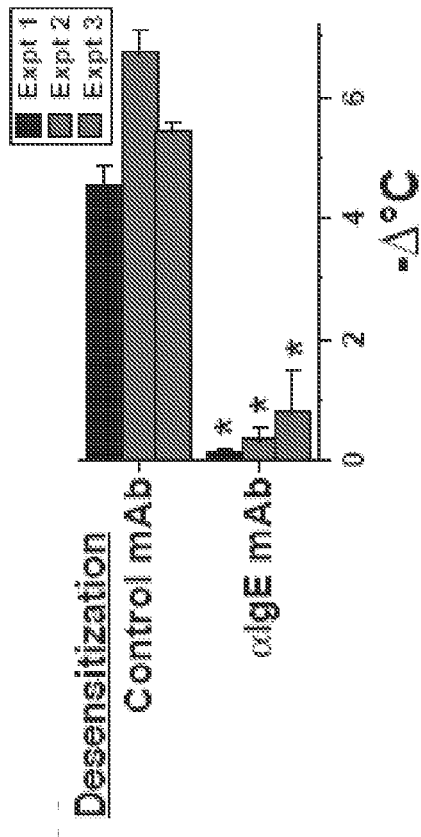
FIGS. 36A-B shows graphs with data showing that mice can be desensitized to IgE-mediated anaphylaxis by rapid desensitization with an activating anti-IgE mAB.
Figure 36B:
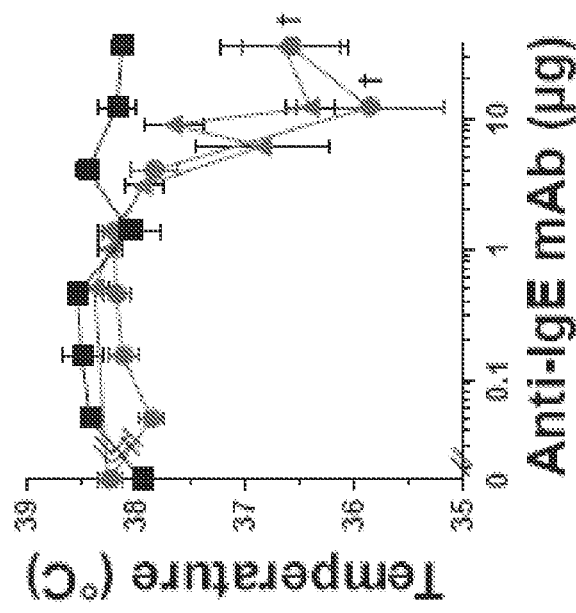

Injection of BALB/c mice with a single >10 μg dose of the activating rat IgG2a mAb to mouse IgE, EM-95, has been shown to induce anaphylaxis characterized by decreased mobility and hypothermia. To determine whether this mAb could be used to rapidly desensitize mice to IgE-mediated responses, mice were first injected i.v. with 50 ng of EM-95, a dose too small to induce hypothermia, and were subsequently injected every hour with 2-3 times the previous dose, until a dose that would normally induce severe shock was reached. This protocol was successful at preventing anaphylaxis induction by a full dose of EM-95 and, in most mice, was performed without a noticeable reaction (FIG. 36A). Some mice, however, did develop relatively mild hypothermia during the desensitization procedure (FIG. 36B). This developed in different individual mice at different doses of EM-95 and may have resulted from neutralization of the initial EM-95 doses by serum IgE, so that the first dose of EM-95 that interacted with mast cell and basophil IgE was sufficient to induce disease. The unpredictability of this problem and its potential severity mitigated against its clinical use for polyclonal desensitization and led to the alternative approach of desensitizing mice with an antibody to FcεRIα, the IgE-binding chain of the high affinity IgER, which is expressed solely on cells.

Rapid Desensitization with an Activating Anti-FcεRIα mAb

Figure 40A:
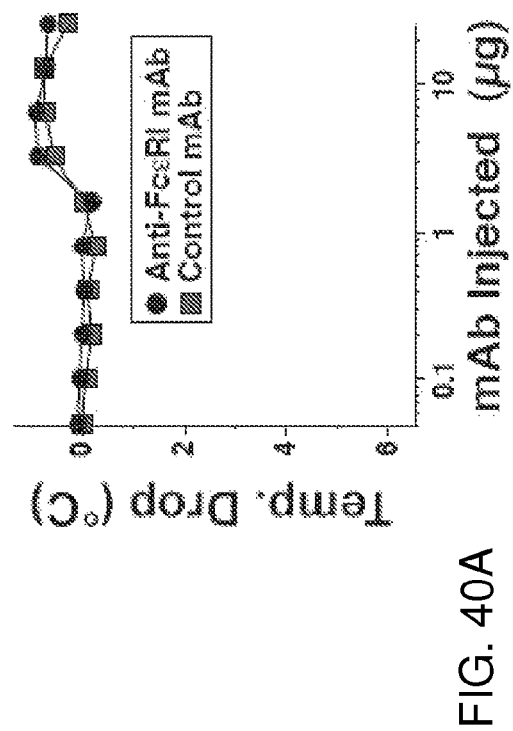
FIGS. 40A-B show that repeated injection of serially increasing doses of MAR-1 prevents the development of an anaphylactic response to this monoclonal antibody.
Figure 42:
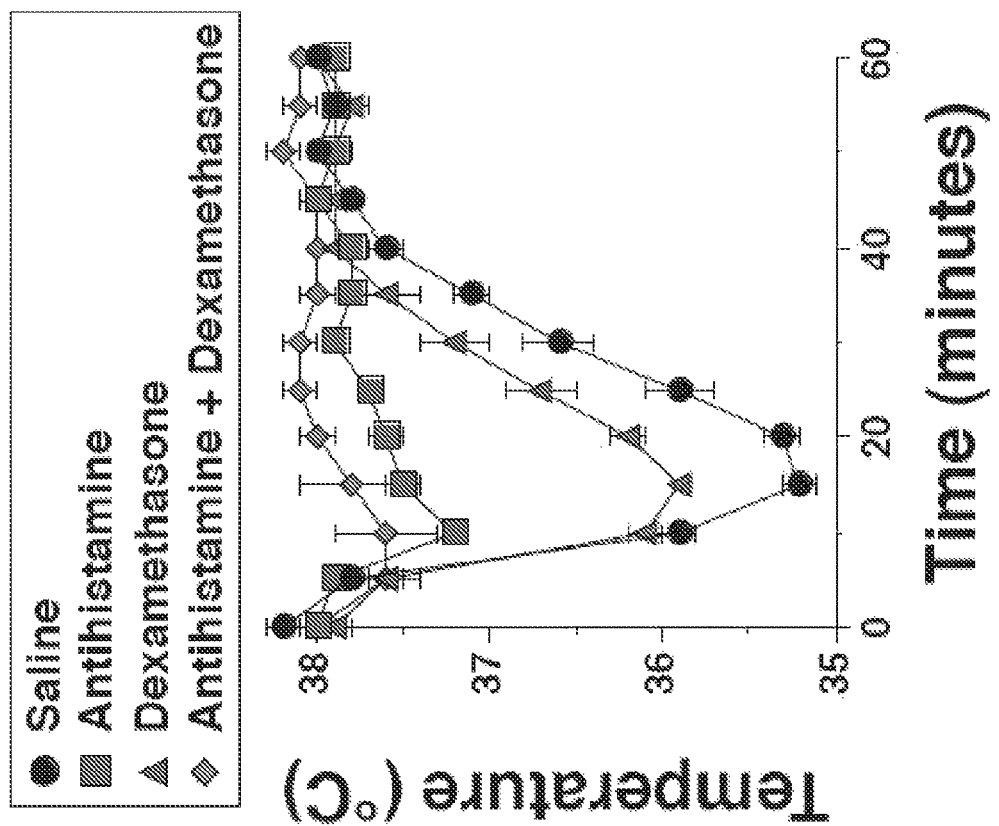
FIG. 42 shows the anaphylactic response to MAR-1 (anti-FcεRIα monoclonal antibody can be inhibited by pretreatment with an antihistamine or a corticosteroid.
Figure 43:
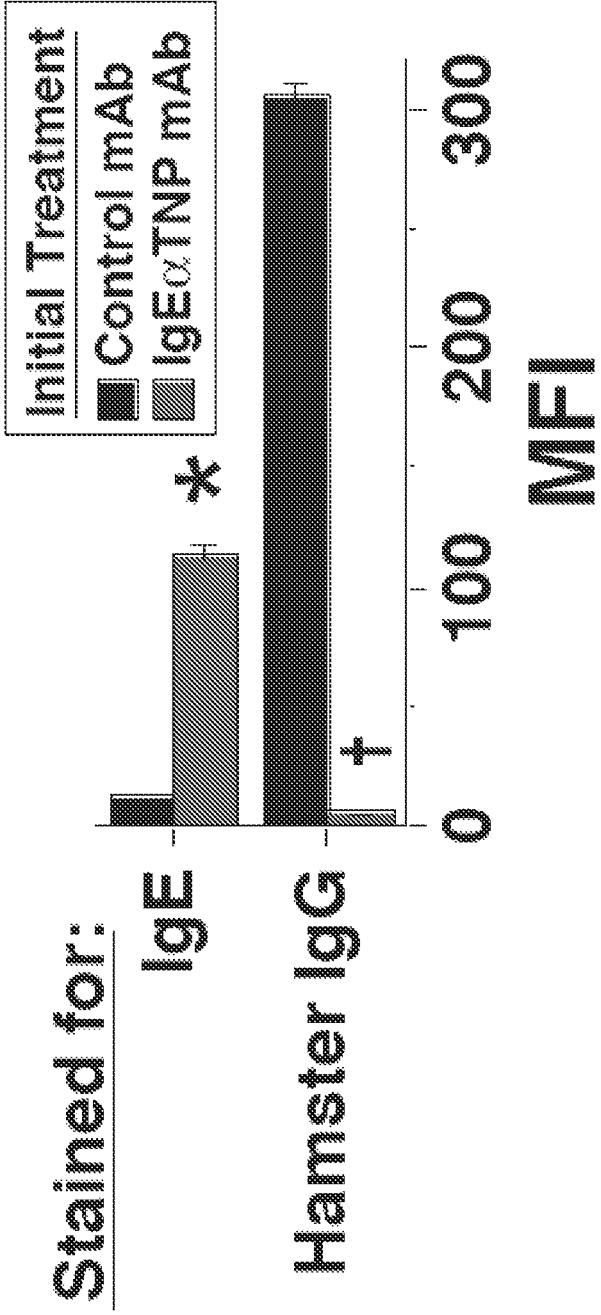
FIG. 43 shows that MAR-1 anti-FcεRIα monoclonal antibody and mouse IgE each blocks the other binding to FcεRI.
Figure 45:
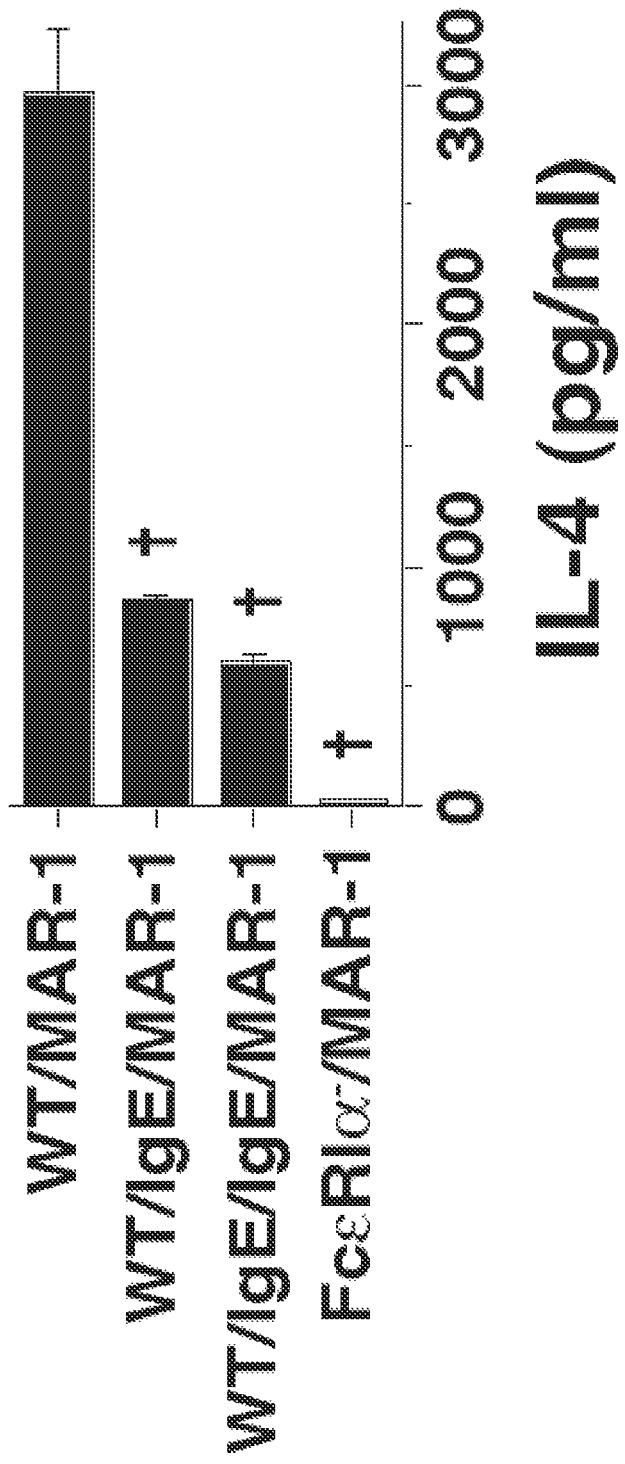
FIG. 45 shows treatment of mice with IgE inhibits the ability of MAR-1 anti-FcεRIα monoclonal antibody to induce an IL-4 response.
Figure 46:
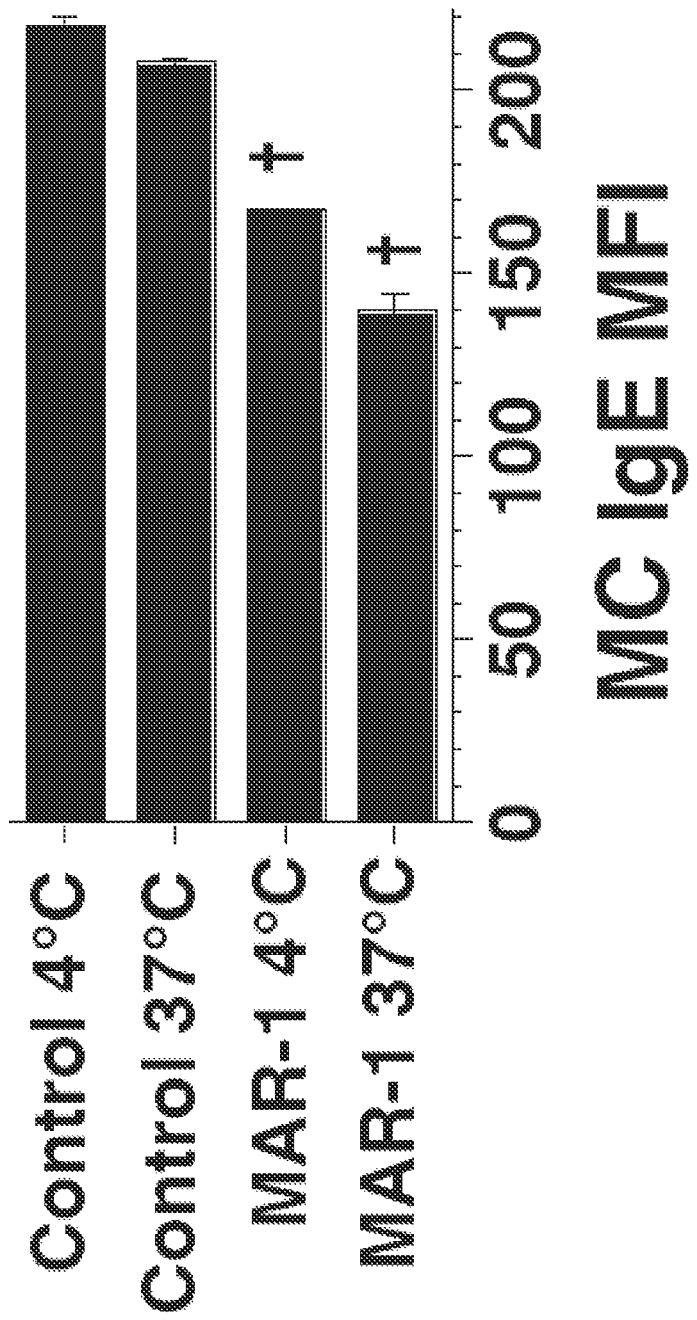
FIG. 46 is a graph showing that treatment of mast cells with MAR-1 anti-FcεRIα monoclonal antibody only slowly decreases IgE expression in vitro.

Initial experiments with MAR-1, a hamster IgG mAb to mouse FcεRIα, confirmed previous demonstrations that it can activate both mast cells and basophils, causing hypothermia, increased serum levels of histamine and MMCP1 and secretion of a large quantity of IL-4 (FIGS. 37, 38A-B, and 39A). Hypothermia could be prevented by administering MAR-1 αFcεRIα mAb through a rapid desensitization approach (FIG. 40A), even when mice were pretreated with a long-acting formulation of IL-4 to make them more sensitive to vasoactive mediators (FIG. 41), or by pretreating mice with an antihistamine and a corticosteroid prior to MAR-1 injection (FIG. 42). However, the interaction of mast cells and basophils with MAR-1 was more complicated than the interaction of these cells with an anti-IgE mAb, because MAR-1 αFcεRIα mAb only bound FcεRI that was not already occupied by IgE (FIG. 43). For this reason, MAR-1 αFcεRIα mAb failed to induce anaphylaxis in mice that had been pretreated with sufficient exogenous IgE to saturate FcεRI (FIG. 44) and induced relatively little IL-4 secretion in these mice (FIG. 45). In addition, MAR-1 αFcεRIα mAb treatment failed to remove most IgE from mast cells during a 1 hr incubation at either 4° C. or 37° C. (FIG. 46). Thus, MAR-1 αFcεRIα mAb, unlike anti-IgE mAb, can only interact with and modulate FcεRI that has not already bound IgE.

Figure 48:
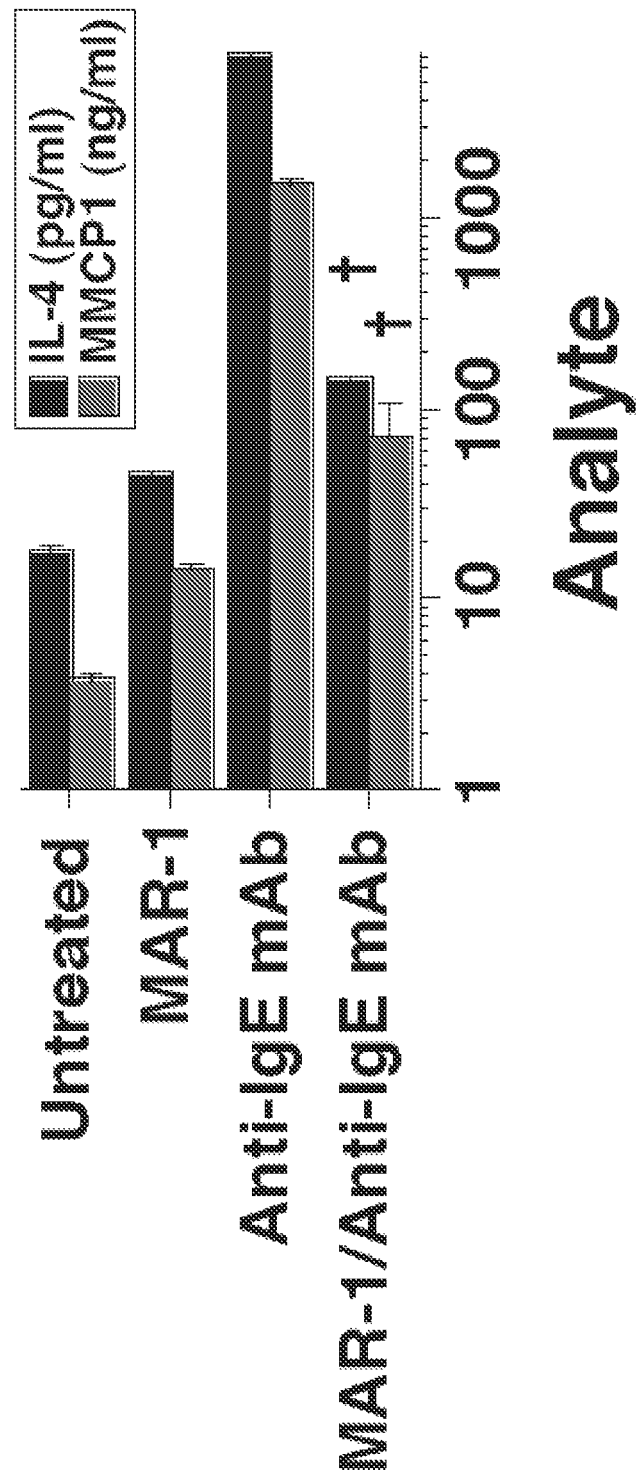
FIG. 48 is a graph showing that rapid desensitization with MAR-1 decreases mast cell MMCP1 secretion and basophil IL-4 secretion.
Figure 49:
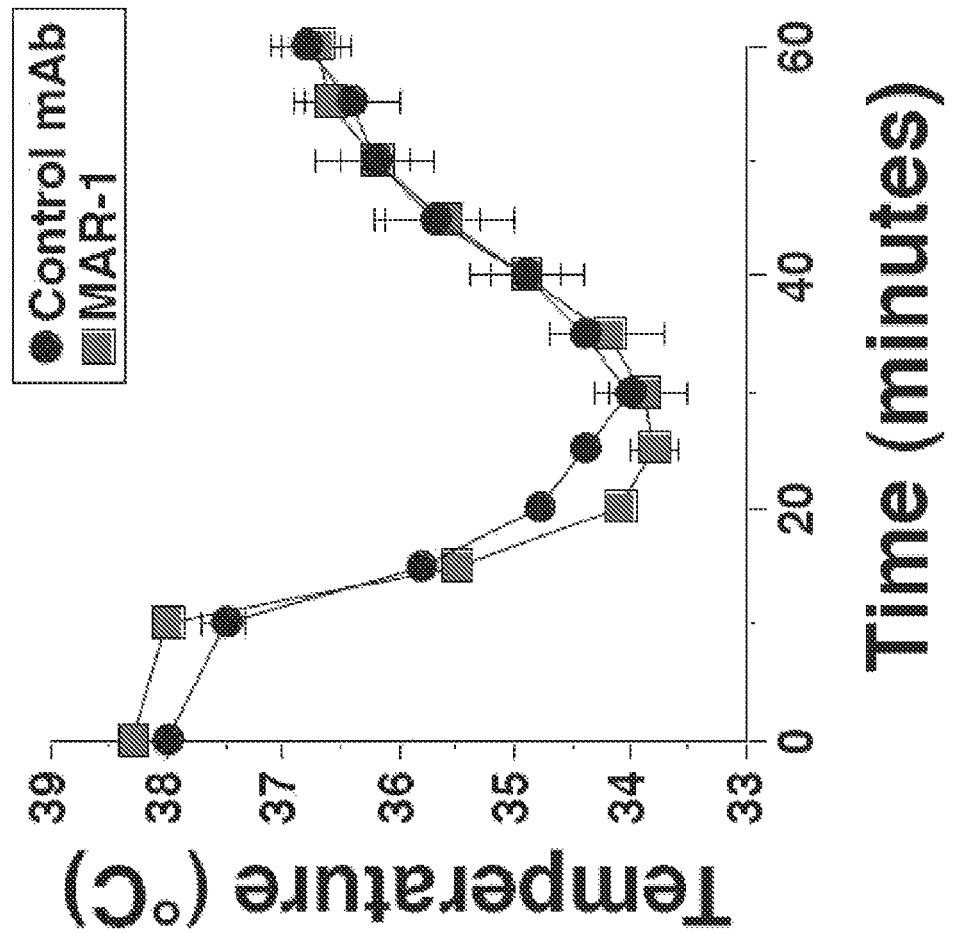
FIG. 49 shows that reduced responsiveness induced by desensitization of mast cells with MAR-1 anti-FcεRIα monoclonal antibody is lost within 48 hours despite the continued presence of MAR-1.
Figures 51A, 51B:
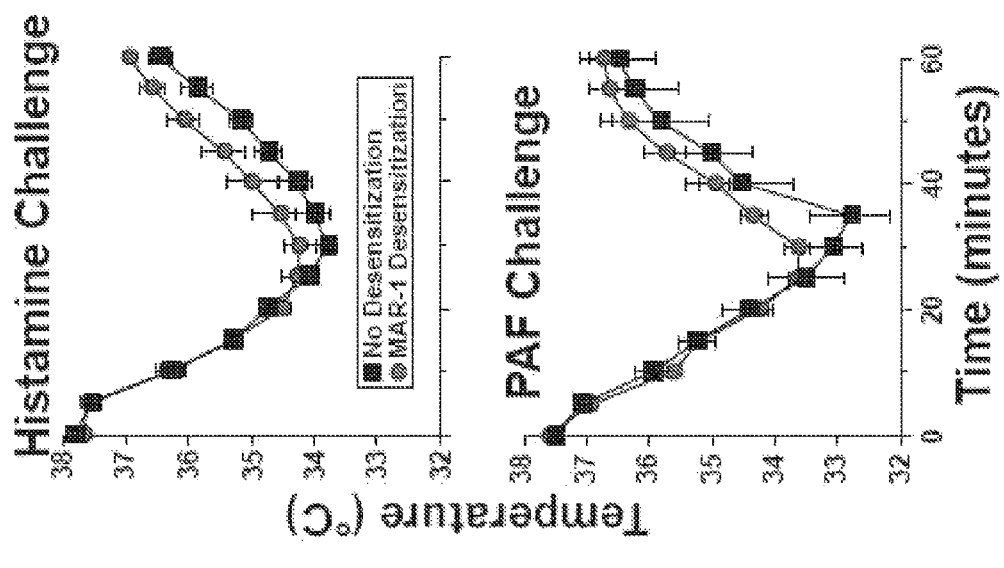
FIGS. 51A-B show that rapid desensitization with MAR-1 does not induce decreased responsiveness to mast cell-produced vasoactive mediators.

This limitation, however, allowed a determination of whether rapid desensitization with MAR-1 αFcεRIα mAb could decrease responsiveness to FcεRI crosslinking, either by EM-95 αIgE mAb or by antigen. Results of this experiment showed a considerable decrease in the degree of hypothermia induced by either EM-95 αIgE mAb or antigen challenge in MAR-1 α FcεRIα mAb-pretreated mice (FIG. 47), as well as decreases in IL-4 and MMCP1 responses to EM-95 αIgE mAb by factors of ~100 and ~30, respectively (FIG. 48). Decreased severity of hypothermia appears to result from temporary mast cell exhaustion rather than decreased mast cell IgE expression, because EM-95 αIgE mAb challenge 2 days later, when MAR-1 αFcεRIα mAb was still present in blood, induced nearly the same degree of hypothermia as was seen in mice that had been pretreated with a control mAb instead of MAR-1 αFcεRIα mAb (FIG. 49). Temporary desensitization did not involve decreased sensitivity of target organs to mediators released by activated mast cells, such as histamine and PAF, because injection of mice that had just undergone rapid desensitization with histamine or PAF induced the same degree of hypothermia as injection of naïve mice with the same dose of the same vasoactive mediator (FIG. 51A). Thus, acute crosslinking of unoccupied FcεRI on mast cells temporarily decreases susceptibility to IgE-mediated anaphylaxis by inducing a relatively short-lived decrease in mast cell responsiveness to signaling through IgE-occupied FcεRI, rather than by removing sufficient IgE-occupied FcεRI to prevent Ag- or anti-IgE mAb-induced mast cell activation or by decreasing sensitivity to mast cell-secreted mediators.

Figures 54A, 54B:
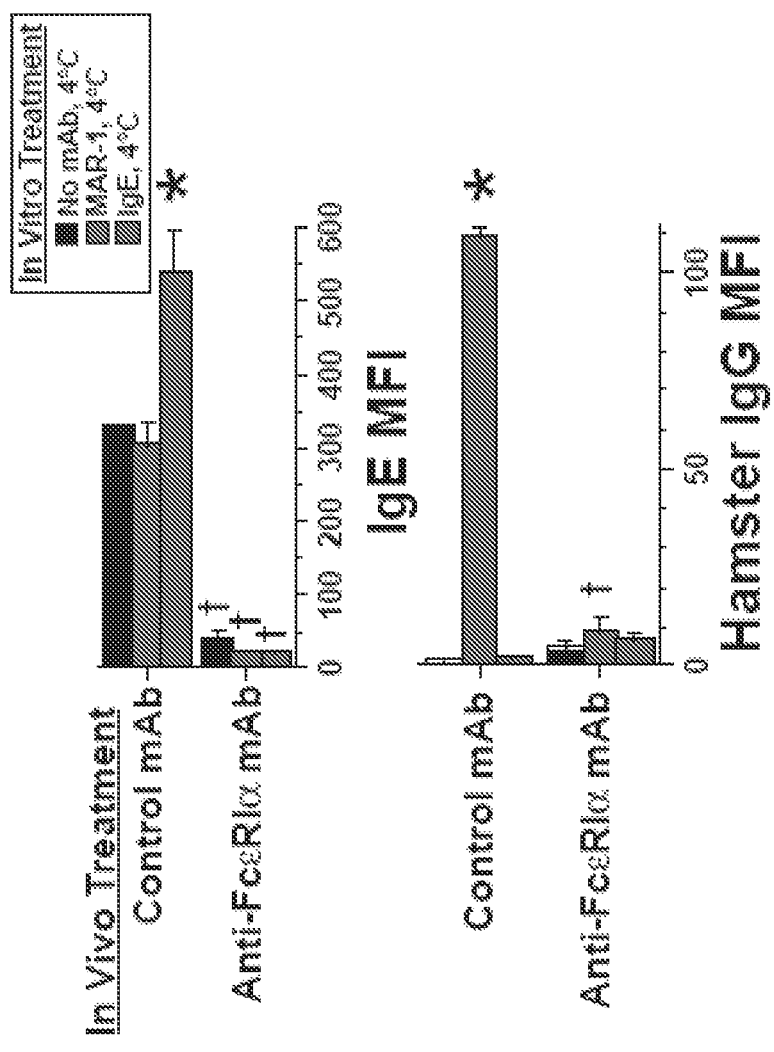
FIGS. 54 A-B show that eight days of in vivo treatment with MAR-1 anti-FcεRIα monoclonal antibody removes most mast cell IgE.
Figure 55A:
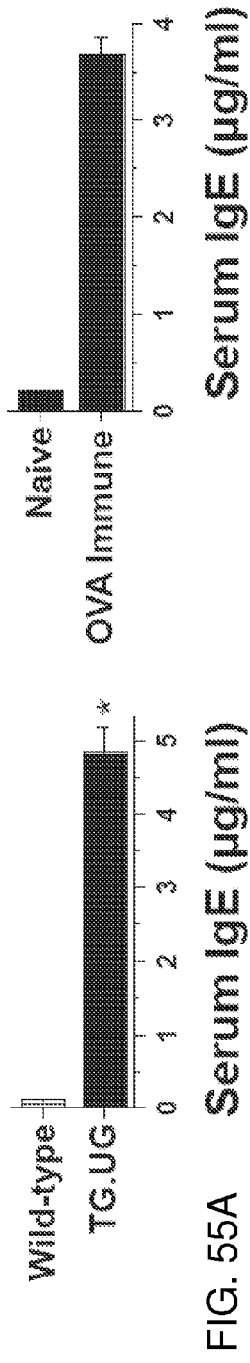
FIGS. 55A-B show that high serum levels of IgE do not prevent the ability of MAR-1 to decrease mast cell IgE expression or delete basophils in vivo.
Figure 55B:
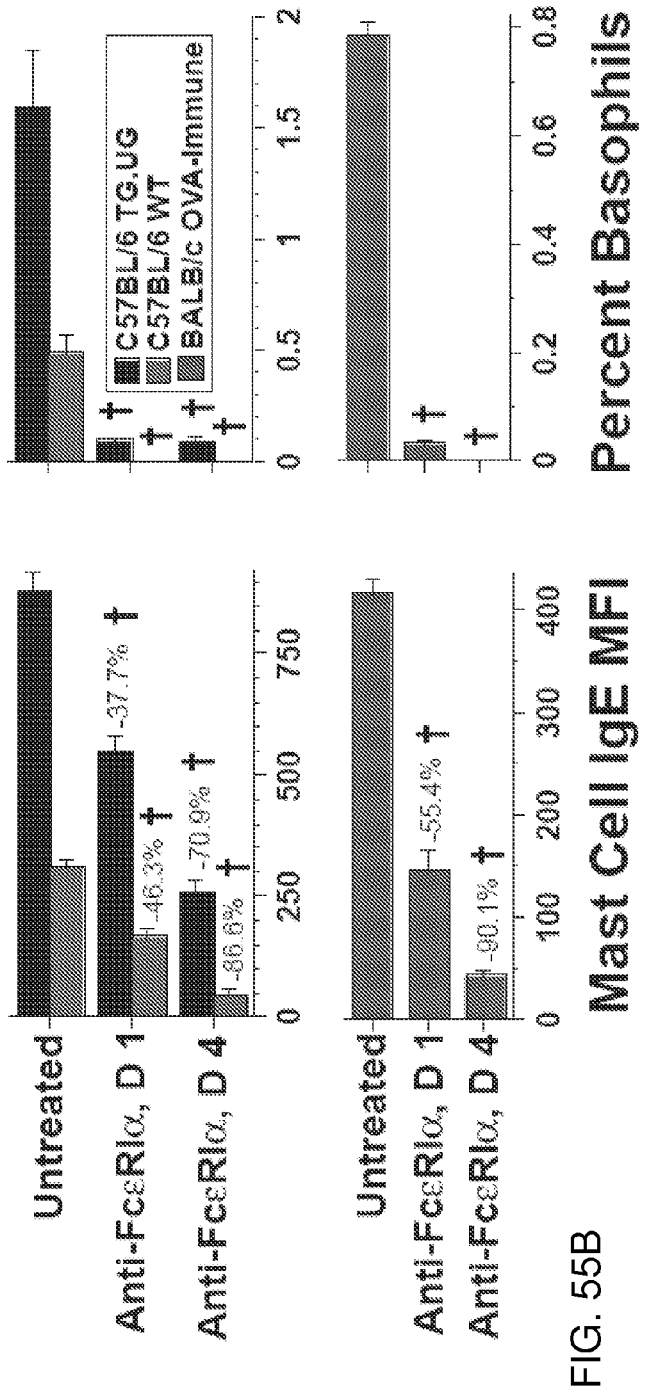
Figure 56:
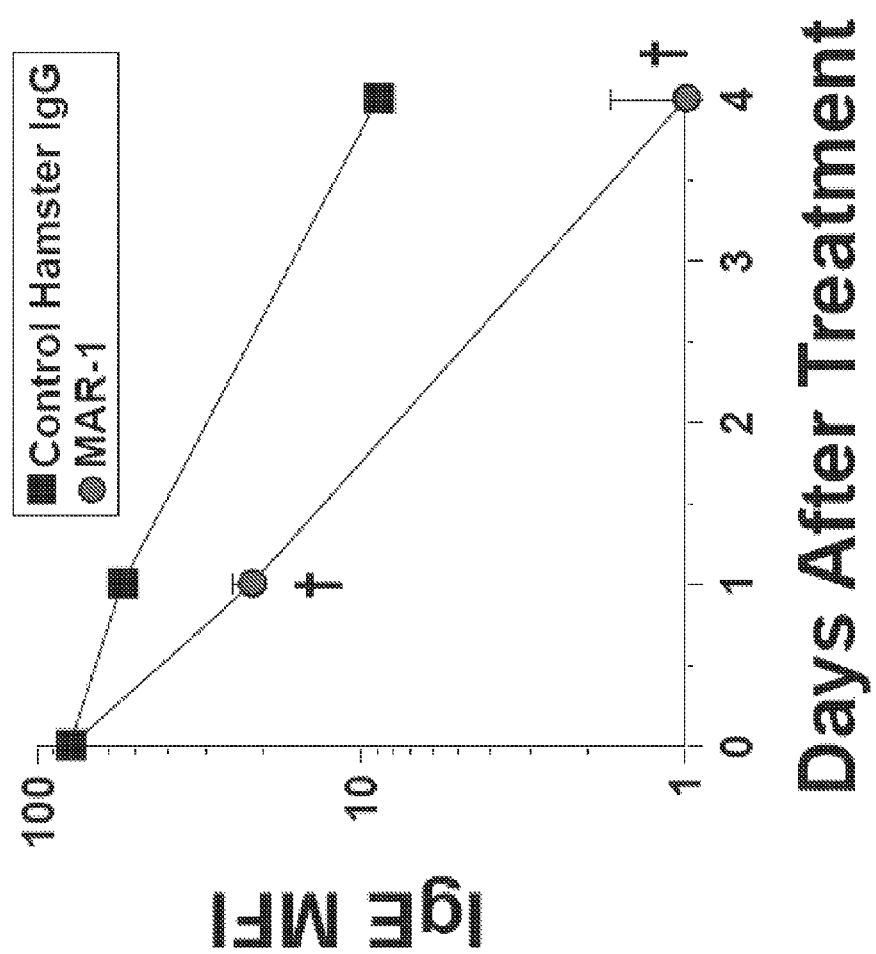
FIG. 56 is a graph showing that MAR-1 accelerates the loss of FcεRI-bound IgE from mast cells.

Although rapid desensitization with MAR-1 αFcεRIα mAb does not rapidly remove pre-existing IgE from mast cells and basophils, it does act more slowly to eliminate basophils and to substantially decrease mast cell IgE expression over time (FIG. 55B). The latter phenomenon is seen even in IL-4-overproducing transgenic C57BL/6 TG.UG mice, which have very high serum IgE levels (FIGS. 55A-B), although it occurs more slowly in these mice than in wild-type C57BL/6 mice. MAR-1 αFcεRIα mAb treatment also rapidly eliminates basophils and depletes mast cell IgE in ovalbumin-immunized BALB/c mice. The reduction in mast cell IgE appears to be a consequence of two effects of MAR-1 binding to FcεRI: 1) internalization of the Mar-1/FcεRI complex (as shown by in vivo staining with MAR-1 αFcεRIα mAb labeled with the fluorochrome pHRodo, which only exhibits detectable fluorescence after internalization and acidification which rapidly prevents newly expressed FcεRI from binding IgE; and 2) an increased rate of turnover of IgE-occupied FcεRI or dissociation of IgE from FcεRI (FIG. 56). Thus, treatment with MAR-1α FcεRIα mAb causes mast cell IgE expression to decrease as IgE bound FcεRI dissociates or turns over at an increased rate and newly expressed FcεRI is internalized before it can bind IgE. Indeed, after 8 days of MAR-1α FcεRIα mAb treatment, mast cell IgE is decreased by 89-93% and fully saturated IgE binding is decreased by 97% (FIGS. 54A-B). However, even after 22 days of MAR-1α FcεRIα mAb treatment, the greatly reduced levels of mast cell IgE are still capable of inducing mild, histamine-dependent shock (but no longer capable of inducing detectable MMCP1 secretion) when mice are treated with EM-95 αIgE mAb (FIGS. 58A-C).

Figure 59:
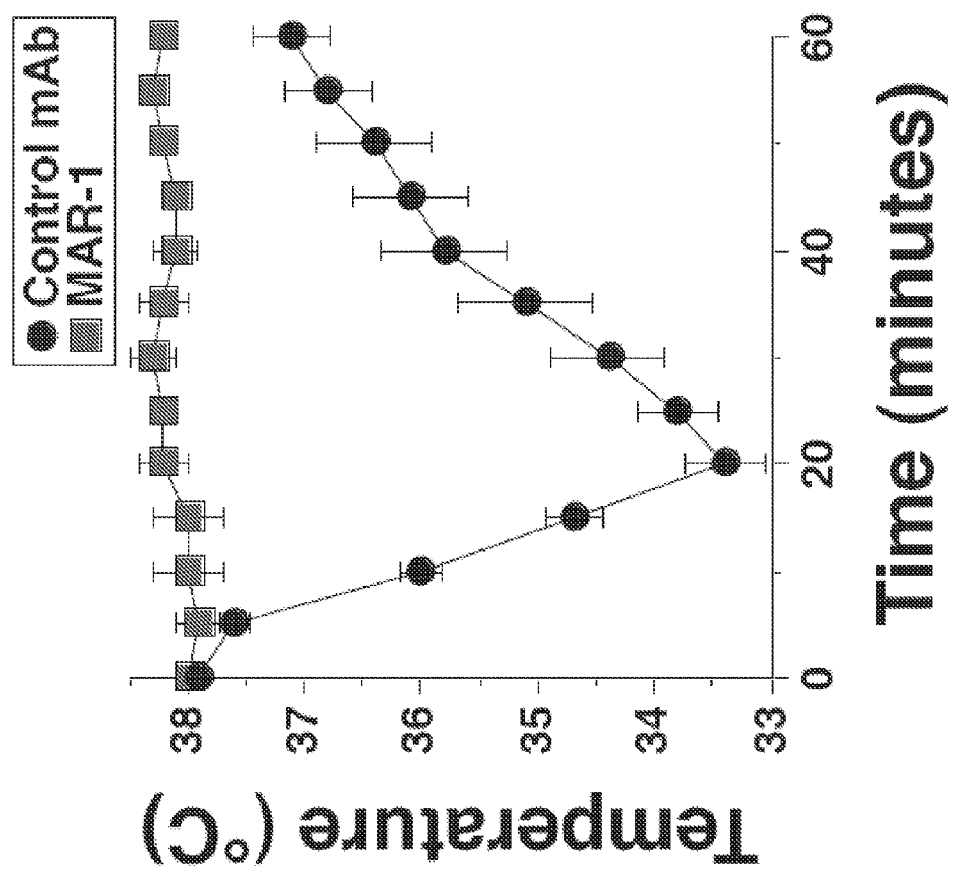
FIG. 59 shows that chronic MAR-1 anti-FcεRIα monoclonal antibody treatment completely suppresses antigen-induced IgE-mediated anaphylaxis.
Figure 60A:
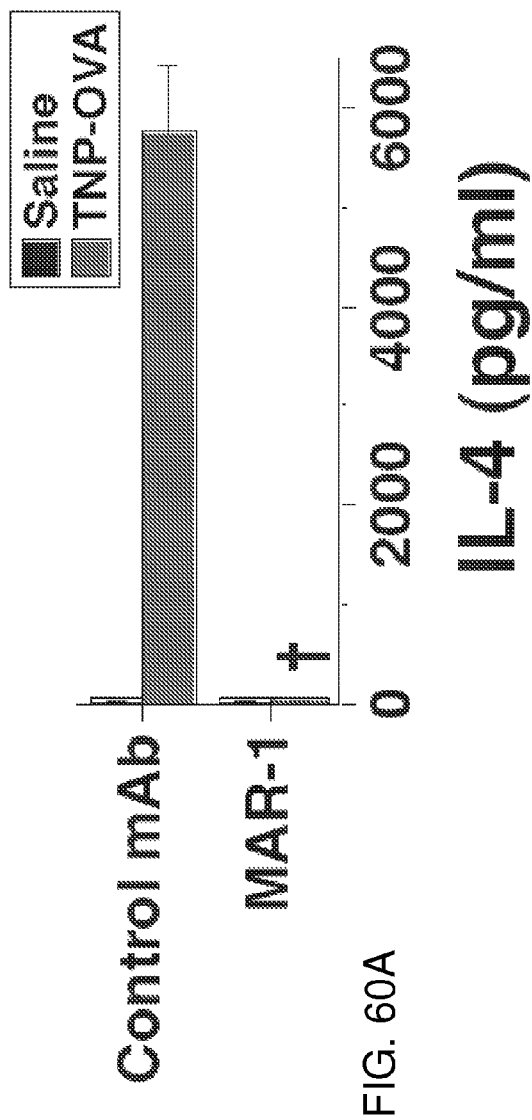
FIGS. 60A-B are graphs showing that rapid desensitization with MAR-1 anti-FcεRIα monoclonal antibody completely blocks the IL-4 and IL-13 responses to antigen-induced IgE-dependent anaphylaxis.
Figure 60B:
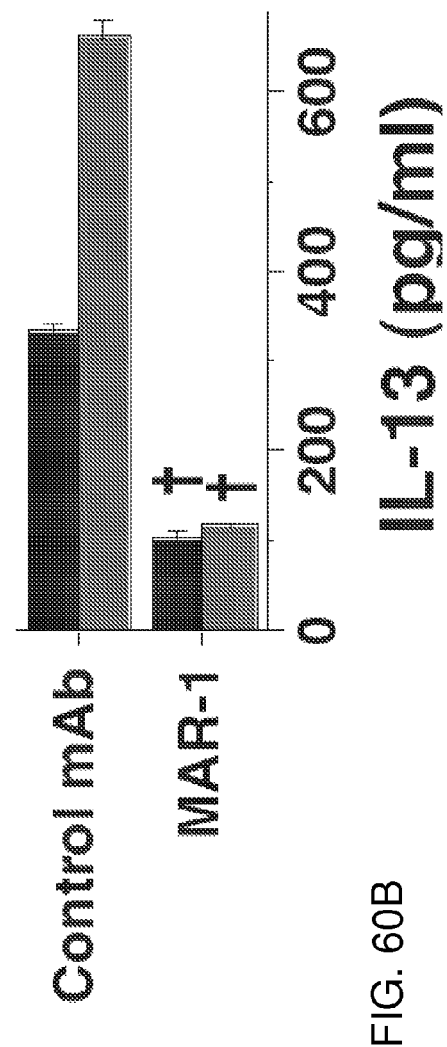

Because EM-95 αIgE mAb treatment is a much stronger stimulus of mast cell degranulation than could be induced by antigen, we evaluated the effects of pretreating mice with IgE anti-TNP mAb and continuing treatment with this mAb while we treated with MAR-1 αFcεRIα or a control mAb for a period of 22 days, then challenged these mice with TNP-OVA. Hypothermia developed in the control mAb-treated, but not in the MAR-1 αFcεRIα mAb-treated mice (FIGS. 59-60). MAR-1 αFcεRIα mAb treatment also totally prevented the basophil-dependent IL-4 response and the mast cell- and basophil dependent IL-13 response to TNP-OVA challenge (FIGS. 59-60). Furthermore, MAR-1 treatment for 7 days totally blocked hypothermia and the MMCP1 response and significantly inhibited the IL-4 and IL-13 responses in mice immunized with goat antimouse IgD antibody and challenged i.v. with goat IgG (FIGS. 61A-C) and in mice immunized with ovalbumin/alum and challenged i.v. with ovalbumin. Thus, treatment with MAR-1α FcεRIα mAb can prevent antigen-specific IgE-mediated passive and active anaphylaxis, even when exposure to antigen-specific IgE precedes MAR-1 αFcεRIα mAb treatment and is continued during the course of this treatment.

Rapid Desensitization with Anti-FcγRIIb/RIII mAb

Figure 64:
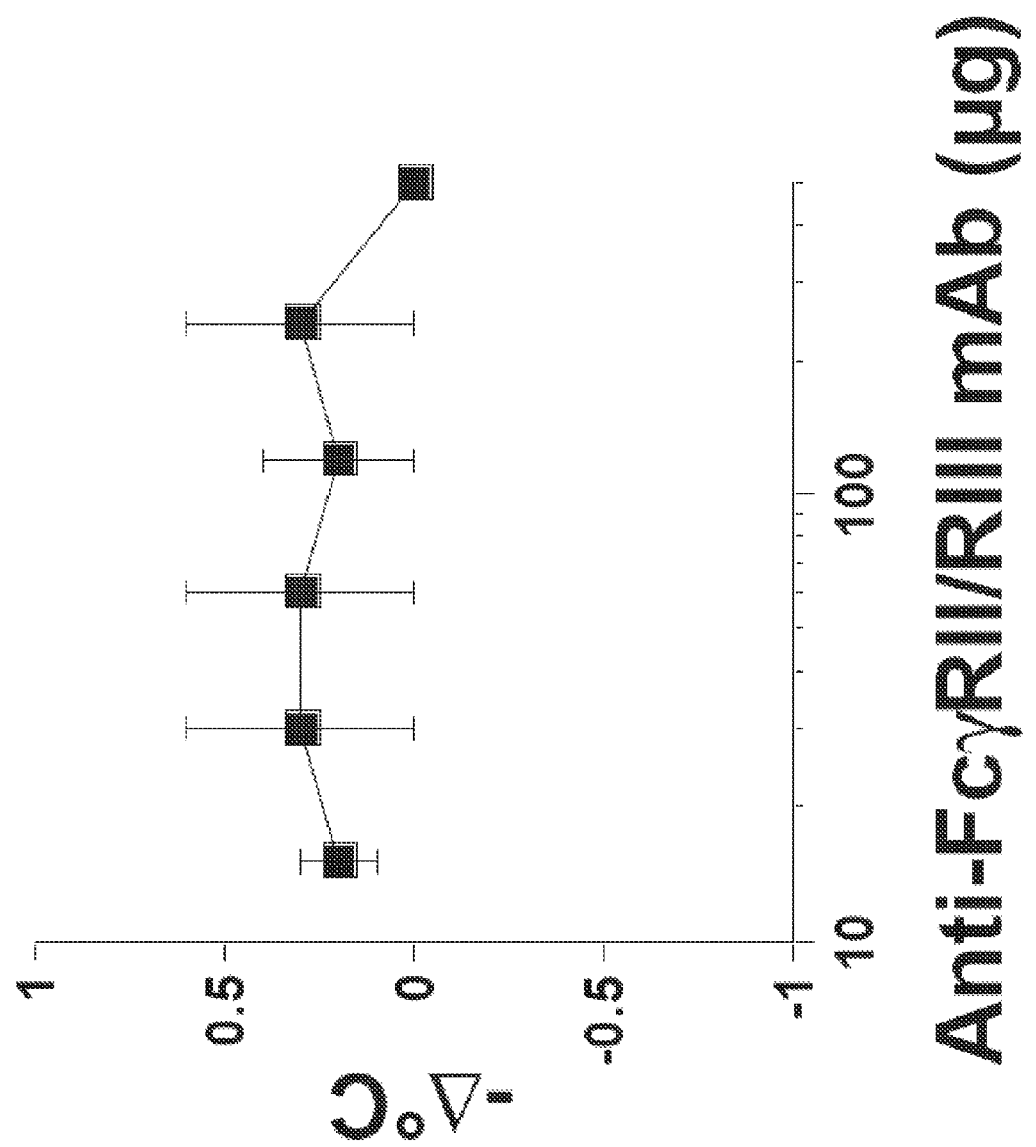
FIG. 64 shows that mice can safely be rapidly desensitized with 2.4G2 anti-FcγRII/RIII monoclonal antibody.
Figures 65A, 65B:
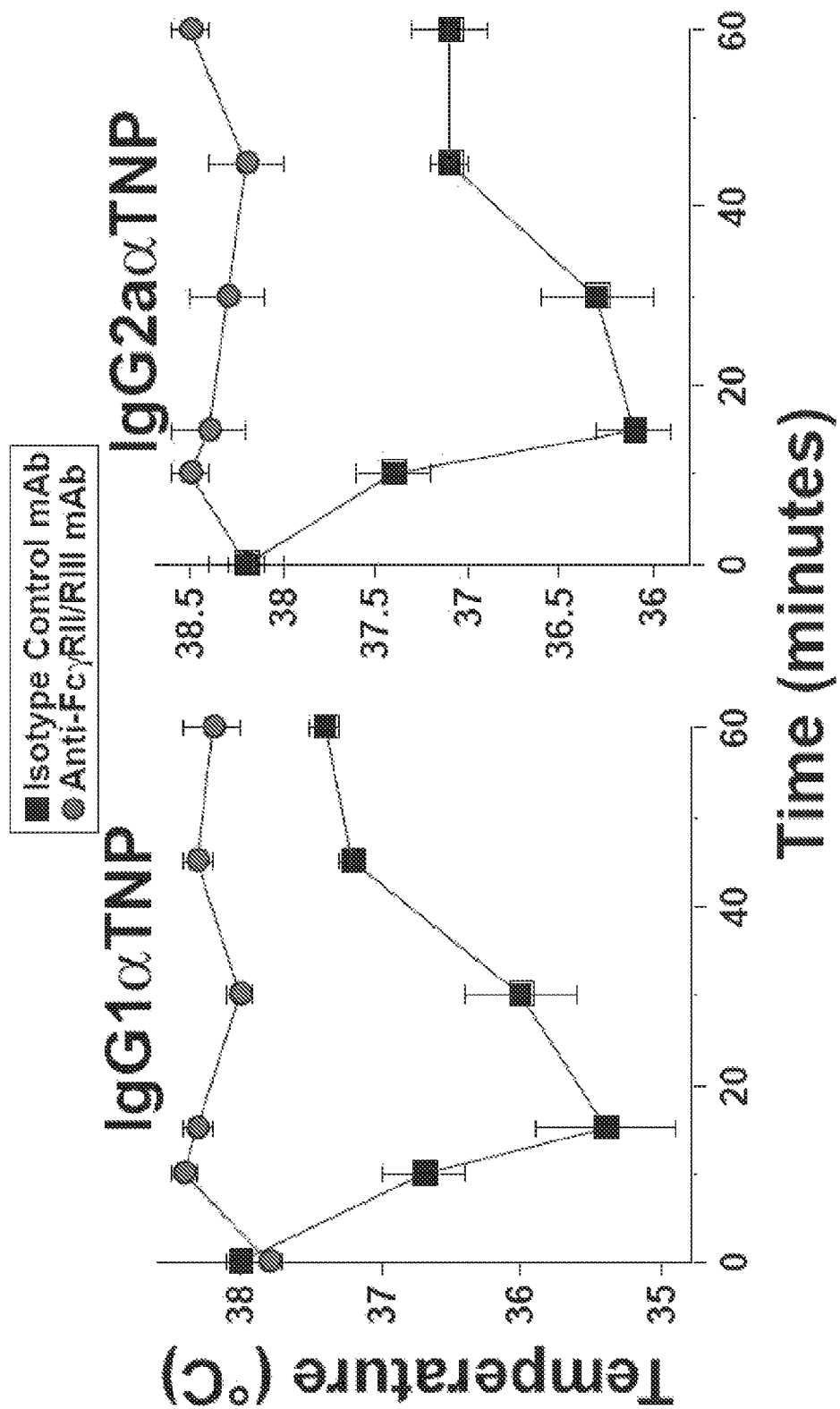
FIGS. 65A-B show that rapid desensitization with 2.4G2 anti-FcγRII/RIII monoclonal antibody suppresses antigen-induced anaphylaxis in mice passively sensitized with IgG1 or IgG2a mAB.

In order to investigate suppression of IgG-mediated anaphylaxis, mice were injected with sequentially increasing doses of 2.4G2, a rat IgG2b mAb that blocks the inhibitory receptor, FcγRIIb; the stimulatory receptor, FcγRIII, and according to some reports, the stimulatory receptor, FcγRIV. Although injection of 60 µg or more of 2.4G2 induces hypothermia (FIG. 63), serial injection of a small dose, followed by increasing doses of this mAb failed to induce hypothermia, even when mice were pretreated with a long acting formulation of IL-4 (FIG. 64). Furthermore, rapid desensitization with 2.4G2 prevented anaphylaxis in mice that were pretreated with IgG1 anti TNP or IgG2a anti-TNP mAb prior to rapid desensitization and challenged with TNP-BSA one day after the completion of rapid desensitization (FIGS. 65A-B). This suggests that 2.4G2 treatment blocks or inhibits signaling through both FcγRIII, which is responsible for IgG1-mediated anaphylaxis, and FcγRIV, which is involved in IgG2a-mediated anaphylaxis. Consistent with this, in vivo 2.4G2 treatment totally blocked staining of blood monocytes and neutrophils with specific anti-FcγRIIb and anti-FcγRIII mAbs and suppressed staining of these cells with specific anti-FcγRI and FcγRIV mAbs by a factor of 3-4 (FIGS. 66A-D). It is not known whether in vivo suppression of FcγRI and FcγRIV staining results from an interaction between the Ag binding site of 2.4G2 and one or both of these receptors or from an interaction between these receptors and the Fc moiety of 2.4G2.

Figures 68A, 68B:
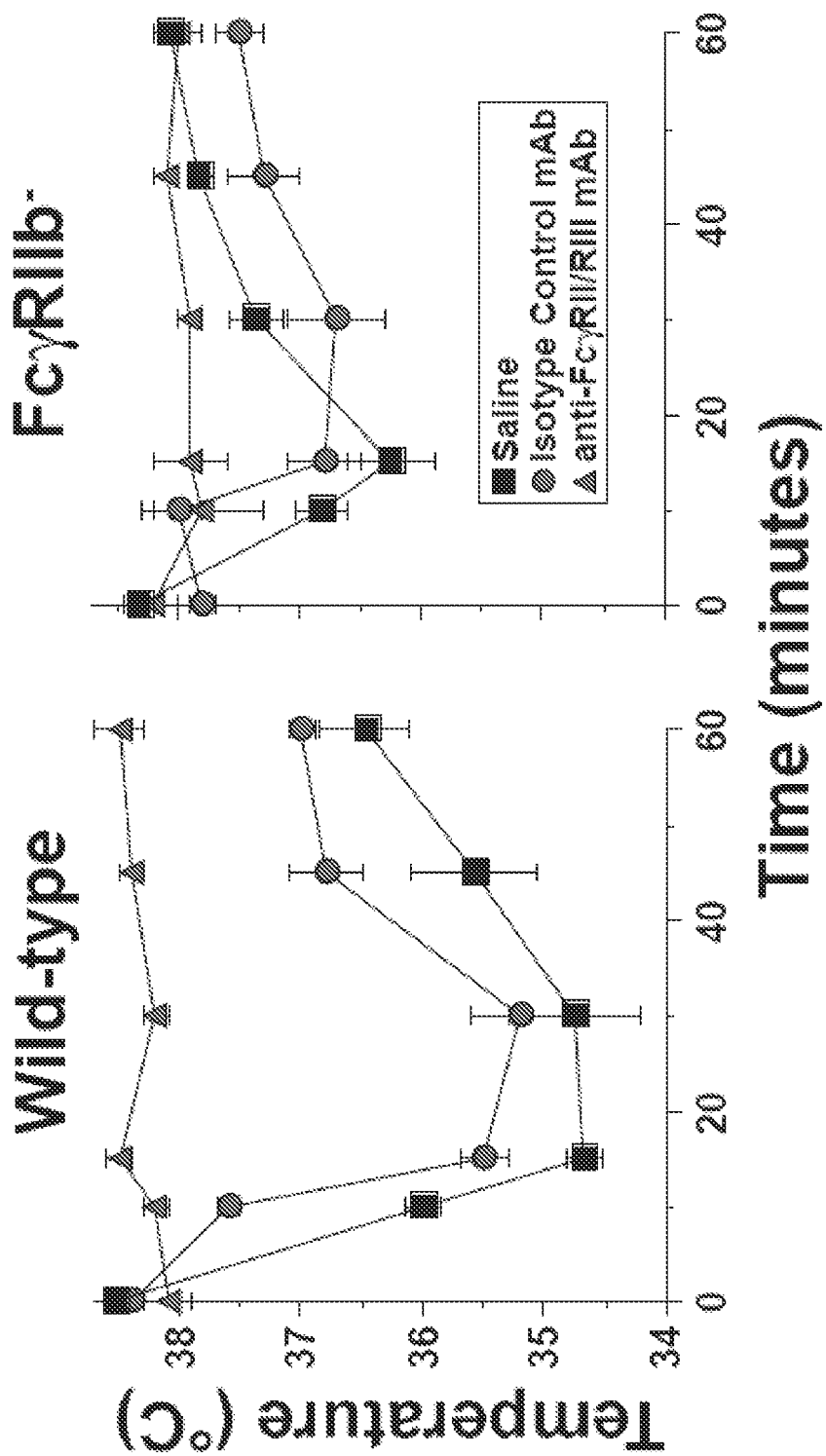
FIGS. 68A-B are graphs showing that rapid desensitization with 2.4G2 anti-FcγRII/RIII monoclonal antibody is FcγRII-independent.

Rapid desensitization with 2.4G2 could theoretically result from inhibitory signaling through FcγRIIb or from blocking binding or signaling through the stimulatory FcγRs. The former possibility is ruled out by the ability of 2.4G2 to block IgG2a mediated anaphylaxis in FcγRIIb-deficient mice (FIGS. 68A-B). Surprisingly, IgG2a-mediated anaphylaxis in these studies was repeatedly found to be less severe in FcγRIIb-deficient than in wild-type mice (FIGS. 68A-B and data not shown). This may reflect spontaneous development of autoimmunity in FcγRIIb-deficient mice, with formation of immune complexes that desensitize cells by signaling through stimulatory FcγRs. Taken together, these results indicate that IgG-mediated anaphylaxis can quickly be blocked in mice by rapid desensitization with an anti-FcγRIII mAb and suggest that the desensitization mechanism is at least partially dependent on cellular activation through FcγRIII and/or FcγRIV, which is suppressed by co-ligation of FcγRIIb.

The data demonstrate that activating mAbs specific for IgE or FcεRIα, delivered by a rapid desensitization approach, can be used to block IgE-mediated anaphylaxis, while an activating mAb specific for FcγRIII, delivered by the same approach, can be used to suppress IgG-mediated anaphylaxis. These approaches take advantage of the abilities of a mAb specific for IgE to neutralize serum IgE and remove cell membrane IgE from mast cells and the abilities of mAbs specific for FcεRIα and FcγRIIb/RIII/RIV to block antigen binding to these receptors and remove these membrane receptors from cells that express them. As a result of the latter effect, the anti-R mAbs act more like non-competitive than competitive inhibitors and allow a relatively small quantity of anti-R mAb to block the binding of a large quantity of IgE or IgG. In contrast, the non-activating anti-IgE mAb, omalizumab, which does not interact directly with FcεRI-bound IgE, but blocks the ability of serum IgE to bind to unoccupied FcεRI, acts more like a competitive inhibitor of IgE-mediated disease and consequently, lacks effectiveness in individuals who have highly elevated IgE levels.

The two techniques that we have evaluated for rapid desensitization of IgE-mediated disease, injection of an activating anti-IgE mAb and injection of an activating anti-FcεRIα mAb, both have advantages and disadvantages. The main advantage of anti-IgE mAb is the rapidity of its suppressive effects. Unlike anti-FcεRIα mAb or omalizumab, which do not directly perturb IgE/FcεRI complexes, anti-IgE mAb neutralizes cell associated IgE as well as IgE dissolved in plasma and lymph. This advantage, however, comes at a price: 1) the therapeutic effects of an activating anti-IgE mAb is likely to be limited by IgE concentration, as has been seen with omalizumab; consequently, more anti-IgE mAb would be needed to treat individuals who have high serum IgE than those with lower amounts of this isotype; 2) the process of rapid desensitization with anti-IgE mAb is less predictable, and hence, more risky, because most of the small doses of mAb that are initially injected will probably be adsorbed by serum IgE without influencing mast cells or basophils. Consequently, it is difficult to gauge how much anti-IgE mAb needs to be administered in small doses before it can safely be given in ascending doses. Our inability to avoid mild hypothermia in some mice during rapid desensitization with EM-95 is probably a consequence of this difficulty. It should be noted that antigen-based rapid desensitization, as it is currently performed by allergists, shares this second problem with an activating anti-IgE mAb, because injected Ag will most likely be neutralized by Ag-specific Ab of all isotypes before it can access IgE on mast cells or basophils. This may account for the fairly common induction of allergic responses with this technique, especially in patients with IgE-mediated food allergy.

In contrast, neither of these problems is likely with anti-FcεRIα mAb, which has a much smaller and more predictable target than anti-IgE mAb and which is entirely directed against cell-associated FcεRI. Administration of sequentially increasing doses of this mAb did not induce hypothermia, even when mice were made particularly sensitive to vasoactive mediators by pretreating them with IL-4. However, while rapid desensitization with anti-FcεRIα mAb can quickly suppress the ability of this mAb to induce anaphylaxis, its inability to rapidly remove FcεRI-bound IgE from mast cells makes it unable to rapidly prevent disease mediated by IgE that was already bound by FcεRI prior to the initiation of rapid desensitization. Consequently, desensitization with an anti-FcεRIα mAb similar to MAR-1 would not be useful in situations in which it is necessary to rapidly suppress an established IgE-mediated allergic response. In contrast, treatment with increasing doses of anti-FcεRIα mAb over a one day period, followed by additional treatment with this mAb for 1-3 weeks, appears to be a safe and effective way to suppress antigen-specific IgE-mediated allergic reactions, as shown by our studies in both passive and active anaphylaxis models.

In contrast to the limitations of IgE-directed therapies, treatment with the anti-FcγR mAb, 2.4G2, appears to be both safe and rapid. Like treatment with MAR-1α FcεRIα mAb, it is directed solely against a cell surface molecule; however, its ability to target that molecule is not inhibited by Ig binding, most likely because FcγRIII and FcγRIV bind Ig with much lower avidity than FcεRI. However, while IgG-mediated anaphylaxis is well established in rodents, its importance in humans is not yet clear, although there are theoretical reasons and some experimental data that suggest that it may be important in situations in which large quantities of immunogenic drugs are administered to individuals who have relatively high titers of IgG antibodies specific for those drugs.

Although our studies with approaches to rapid polyclonal desensitization were primarily carried out to test the feasibility, rather than the mechanism of this approach, they provide insights into the mechanisms involved in antigen-based rapid desensitization. The ability of rapid desensitization with anti-FcεRIα mAb to initially partially suppress IgE-mediated anaphylaxis before decreasing mast cell-associated IgE suggests that the slow, persistent mast cell activation decreases mast cell responsiveness. This state of partial anergy is short-lived, however, inasmuch as the decrease in the severity of IgE-mediated anaphylaxis is lost after 2 days, despite the continued presence of anti-FcεRIα mAb (which has very limited ability to activate mast cells at this point because it now can bind only to FcεRIα that is newly inserted into the mast cell membrane). Full suppression of IgE-mediated anaphylaxis by anti-FcεRIα mAb occurs only after several days, when FcεRI turnover, coupled with anti-FcεRIα mAb modulation of its target, has reduced mast cell membrane IgE to a level incapable of mediating the massive mast cell degranulation that is required to induce anaphylaxis. It seems likely that antigen-induced rapid desensitization works in the same ways: limited induction of partial anergy, but more importantly, depletion of antigen-specific IgE. In vitro studies that demonstrate that mast cells can be desensitized by Ag removal of their membrane IgE without making them unresponsive to repeated IgE priming and Ag challenge, as well as in vivo studies that demonstrate that rapid desensitization with antigen is usually short-lived in the absence of continuing antigen administration are consistent with this conclusion.

Studies with 2.4G2 desensitization of IgG-mediated anaphylaxis also provide a mechanistic insight. Although desensitization might have resulted from signaling through the inhibitory receptor, FcγRIIb, which is bound by 2.4G2, 2.4G2 effectively desensitized FcγRIIb deficient mice. In fact, the decreased responsiveness of these mice to IgG2a-mediated anaphylaxis, as compared to FcγRIIb-sufficient mice, is compatible with the possibility that FcγRIIb is actually a brake on desensitization, which could result from persistent limited activation of basophils, which express FcγRIII, and macrophages and neutrophils, which express both FcγRIII and FcγRIV, by circulating immune complexes.

In sum, the data provide evidence that polyclonal rapid desensitization with antibodies to IgFcRs is a feasible way to suppress immediate hypersensitivity reactions, whether mediated by IgE or IgG. Although the antibodies used can induce anaphylaxis if administered initially in full doses, this is also true for rapid desensitization protocols that administer an allergen rather than an antibody. In addition, rapid desensitization with anti-IgR mAbs may be safer than rapid desensitization with an allergen, because allergen will bind to both soluble and cell associated Ig, while antibodies to IgRs bind only to these cell-associated molecules. An additional layer of protection for anti-IgR-mediated rapid desensitization can be provided by pretreatment with an antihistamine or antihistamine plus corticosteroid. Furthermore, while rapid desensitization with an allergen may last only a short time, because most allergens have a short in vivo half-life and allergen-specific IgE is likely to reaccumulate once the allergen is no longer present, the long in vivo half-life of IgG antibodies should prolong protection provided by these mAbs. Compared to treatment with a non-activating anti-IgE mAb, such as omalizumab, rapid desensitization with anti-IgFcR mAbs would be expected to be more effective, particularly in patients who have high levels of serum IgE, but also more risky. Even this disadvantage is not totally clear, because omalizumab has also induced anaphylactic reactions, although the mechanisms involved are not fully understood. All in all, rapid desensitization with anti-FcR mAbs appears to provide a safe and effective way to suppress both IgE- and IgG-mediated immediate hypersensitivity reactions in mice, regardless of the allergen involved. These observations suggest that it would be reasonable to generate anti-IgFcR mAbs appropriate for human use and evaluate whether they have the same advantages and safety in humans that we have found in mice. Anti-human FcεRIα mAb may be useful for treating food allergy, atopic dermatitis, asthma and other disorders that are primarily IgE-mediated or have an important IgE-dependent component. Rapid desensitization with a mAb specific for human FcγRIII might similarly be expected to be useful for preventing immediate hypersensitivity reactions in patients who are repeatedly infused with therapeutic mAbs and, possibly, for treating diseases that have an FcγR-mediated component, such as systemic lupus erythematosus, some hemolytic anemias, and myasthenia gravis.

III. Detailed Explanations of Selected Figures

Figures 6A, 6B, 6C:
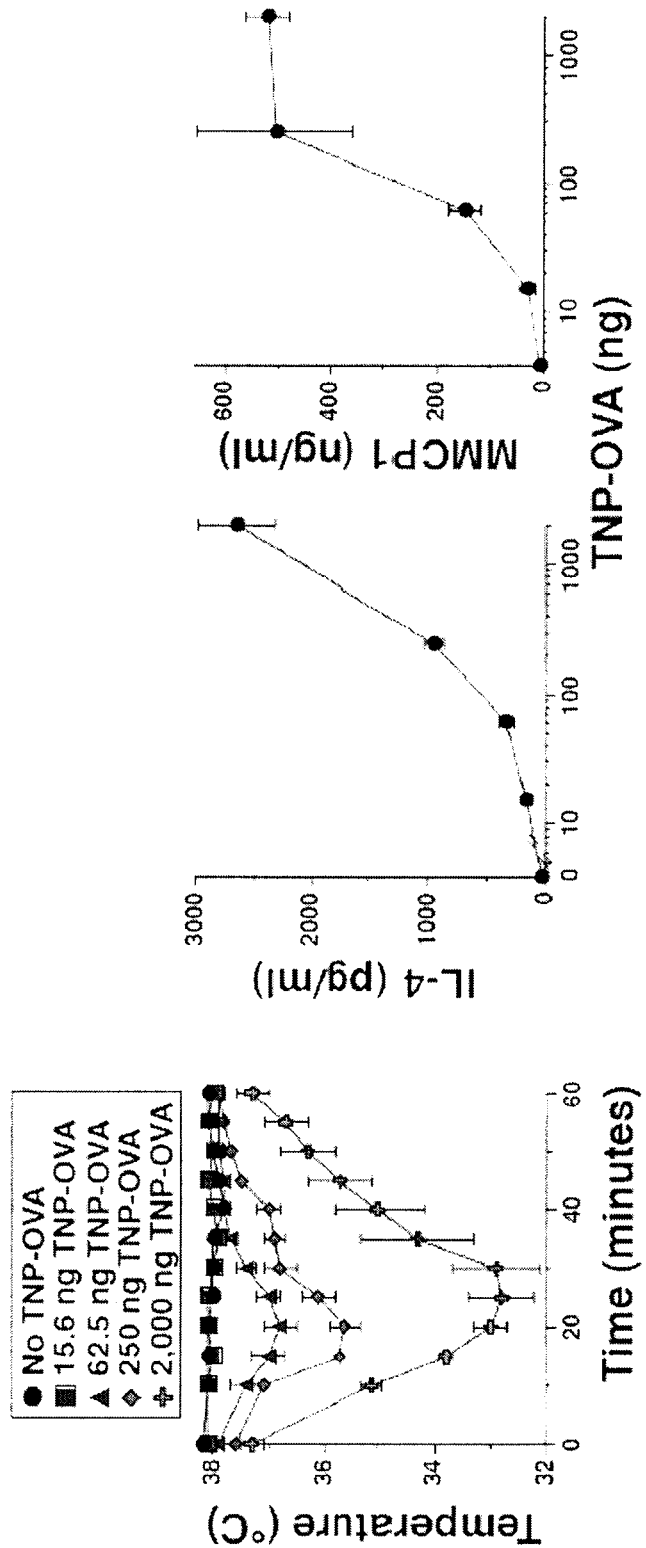
FIGS. 6A-C show mice primed with IgE Anti-TNP mAB develop dose-dependent IL-4, MMCP1 and anaphylactic responses to TNP-OVA.
Figure 7:
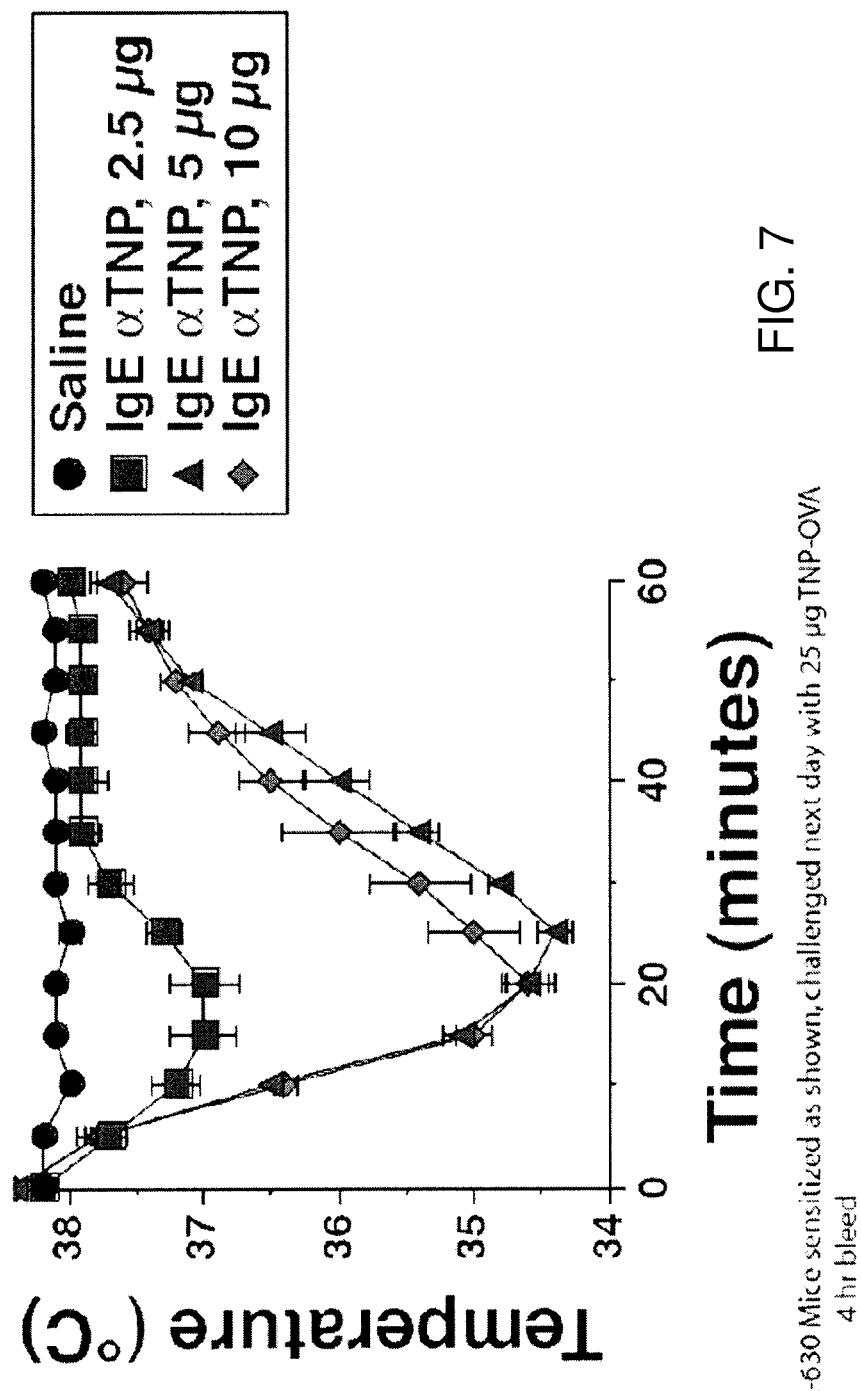
FIG. 7 shows the anaphylactic response to TNP-OVA requires dose-dependent sensitization with IgE anti-TNP Mab.
Figure 8:
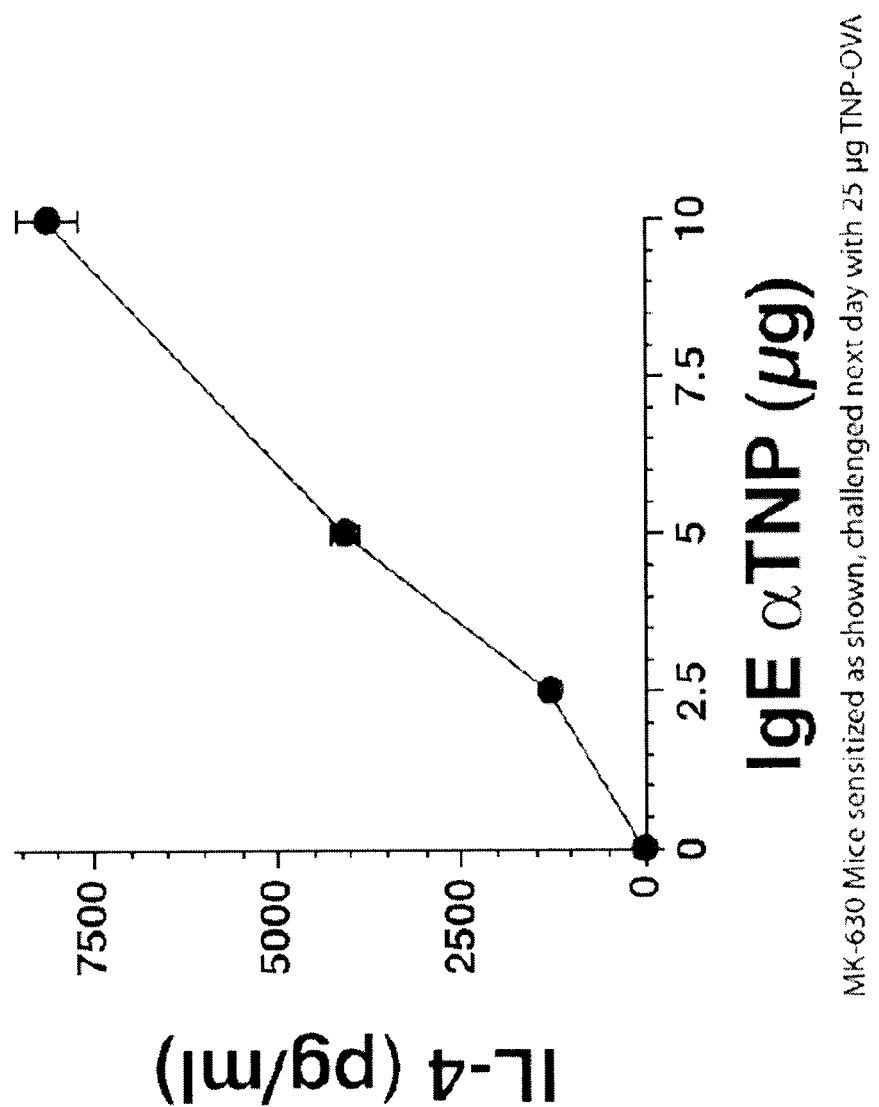
FIG. 8 shows the IL-4 response to TNP-OVA requires dose-dependent sensitization with IgE ANTI-tnp Mab.
Figure 9:
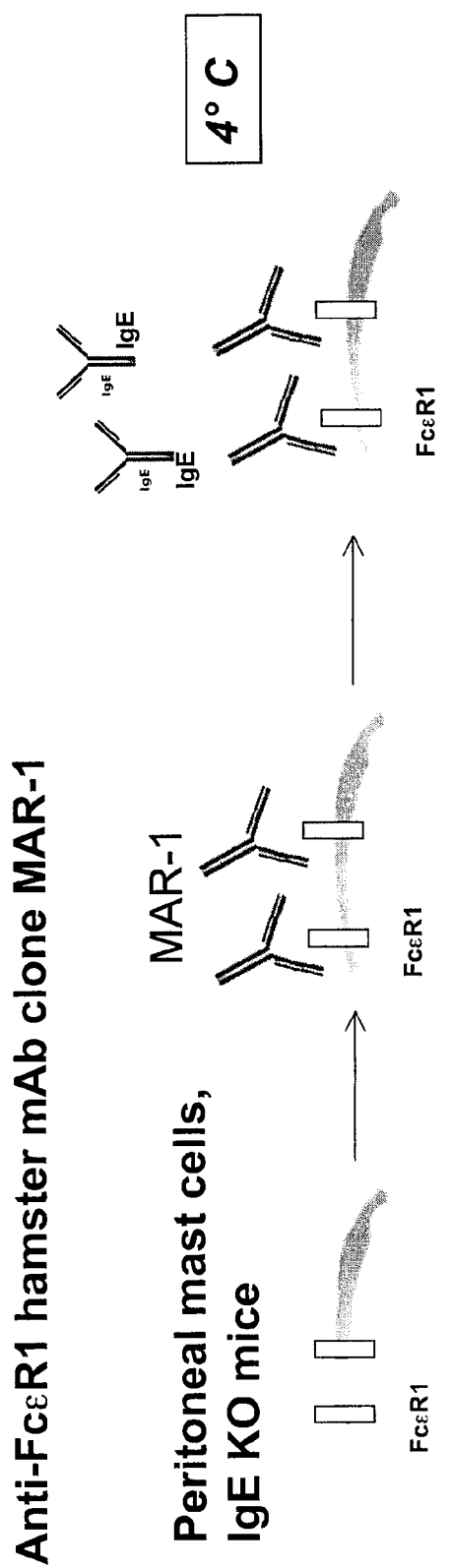
FIG. 9 shows the experimental setup to determine whether MAR-1 can prevent IgE from binding to mast cells.
Figure 10:
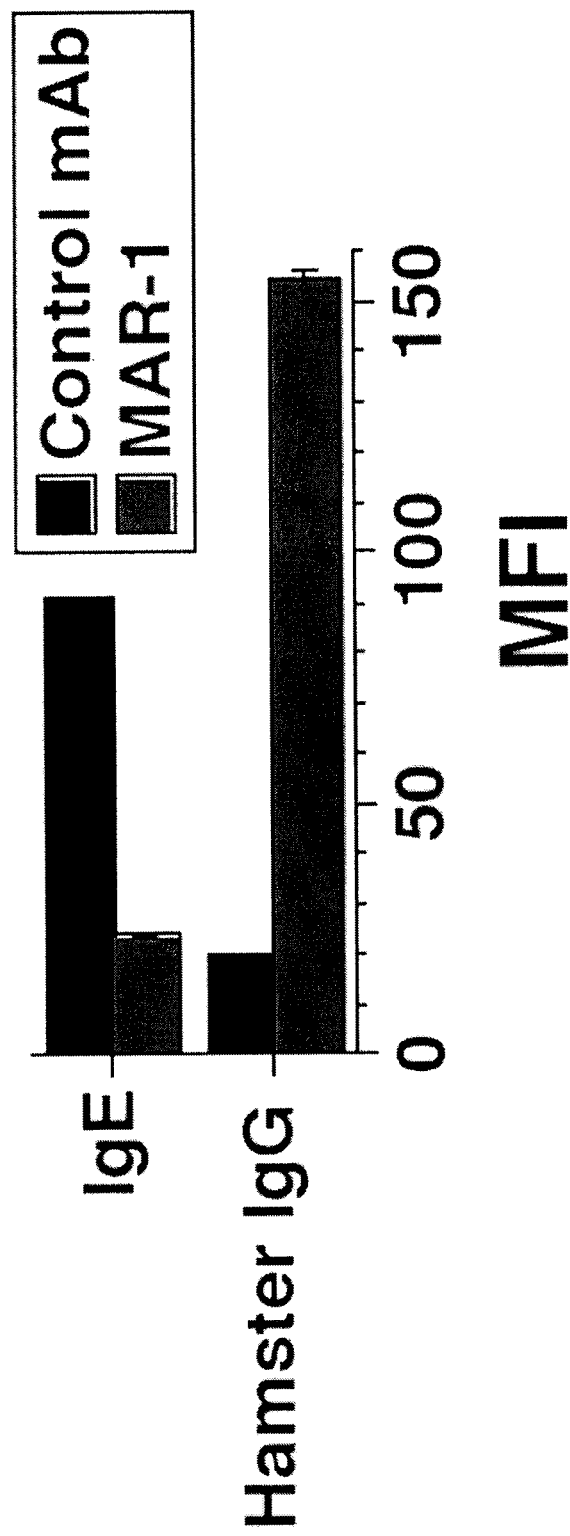
FIG. 10 shows that anti-FcεRI mAB (MAR-1) blocks mast cell binding of IgE.
Figure 11:
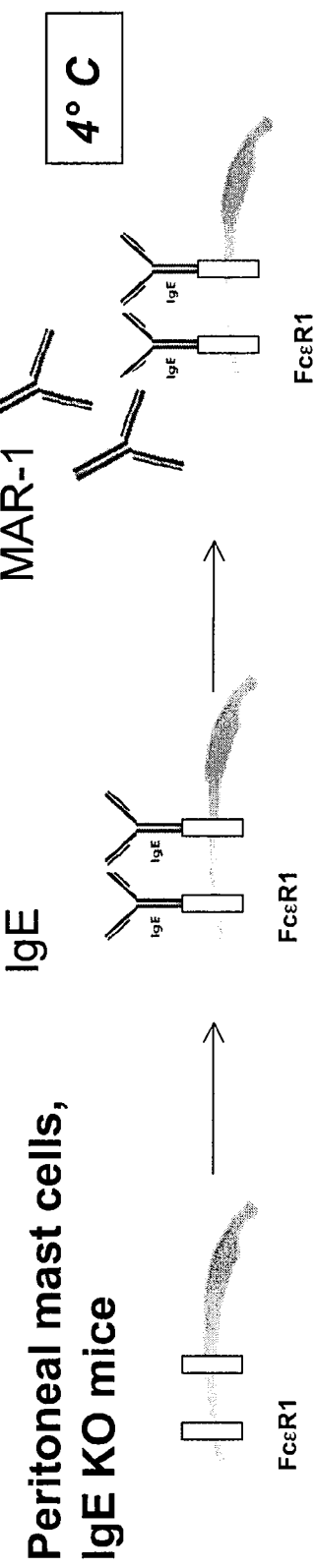
FIG. 11 shows the experimental setup to determine whether IgE can block binding of MAR-1 to mast cells.
Figure 12:
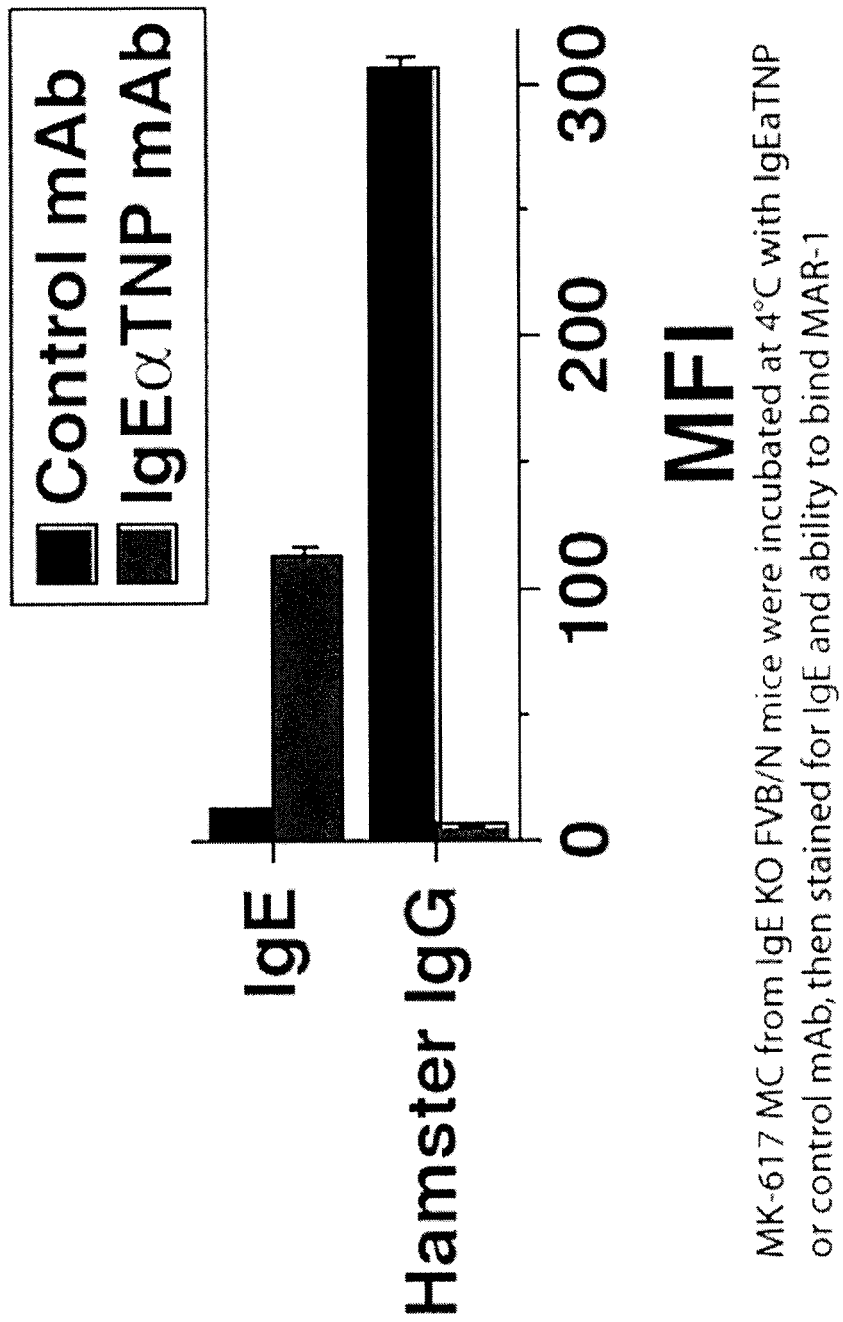
FIG. 12 shows that mast-cell bound IgE blocks MAR-1 binding.
Figure 13:
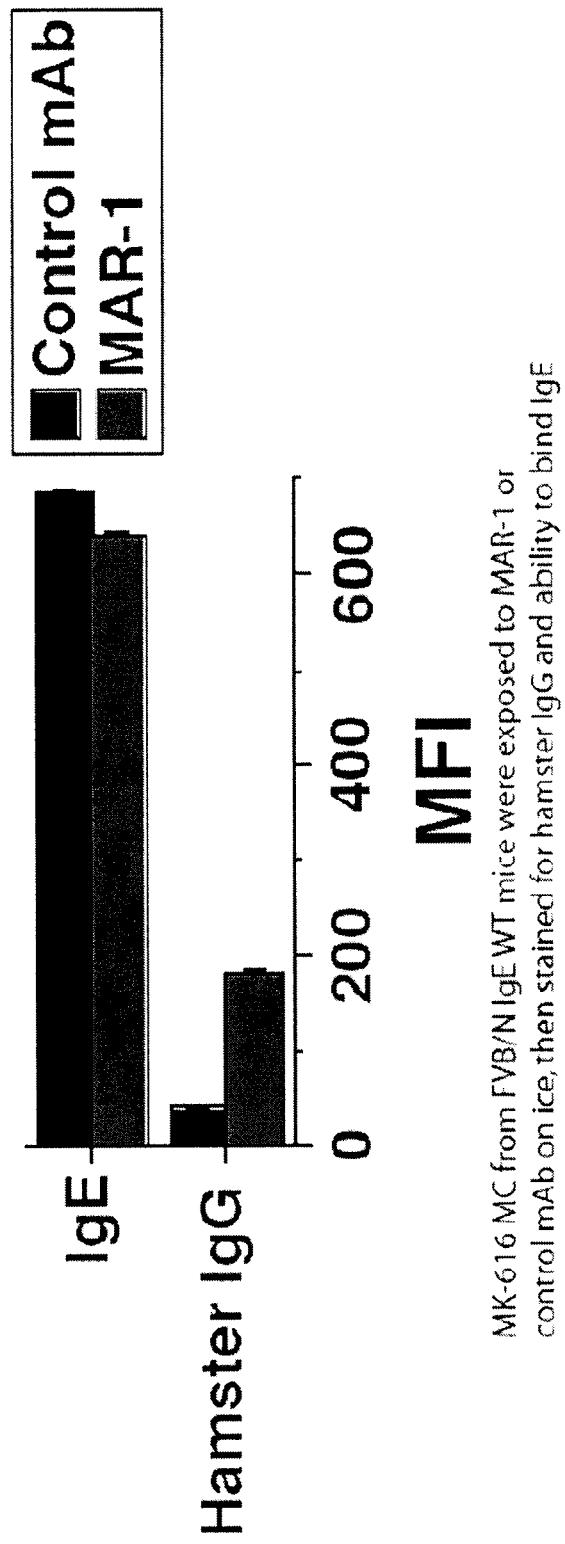
FIG. 13 shows MAR-1 has limited ability to displace mast cell-bound IgE.
Figure 14:
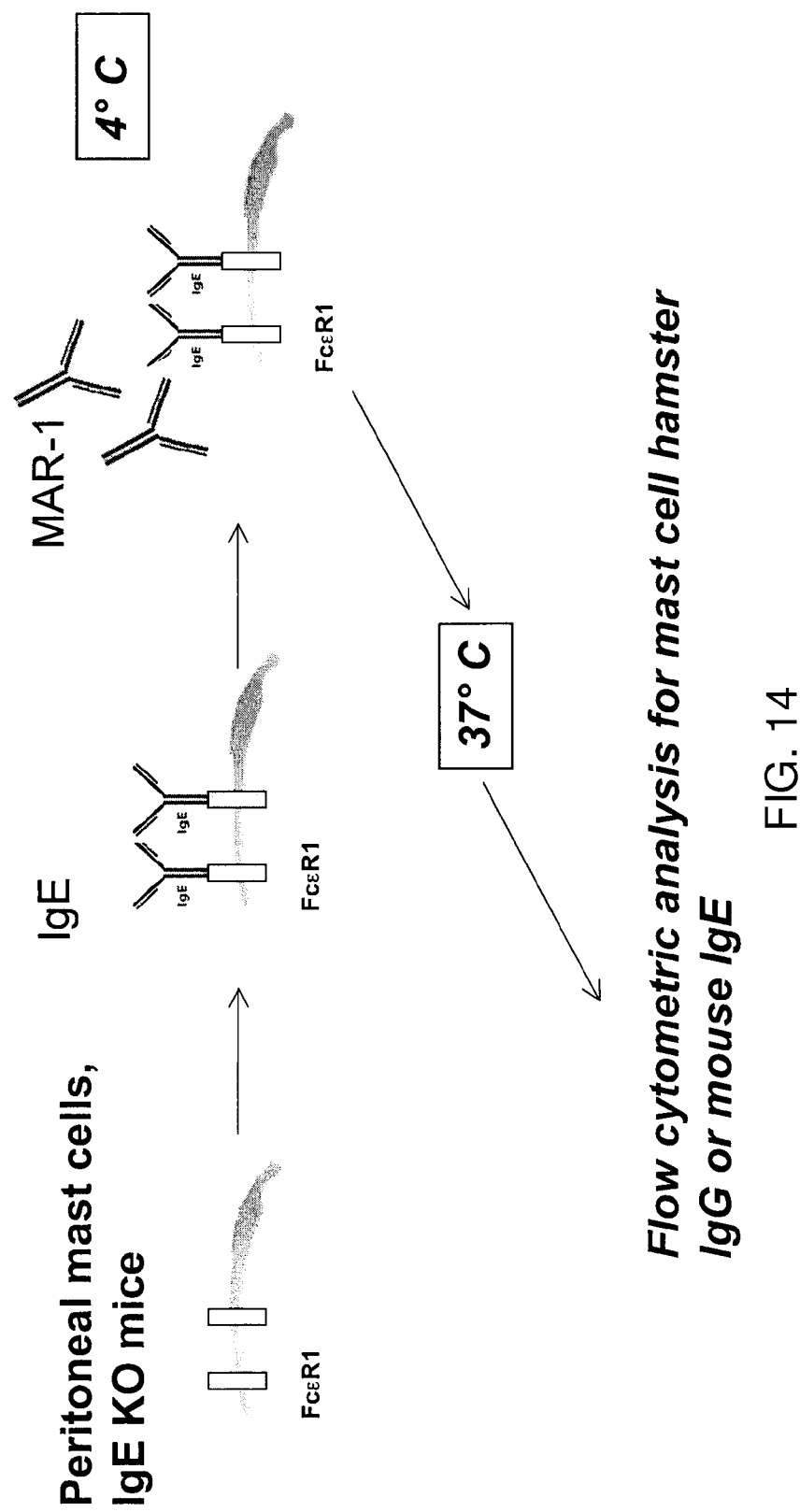
FIG. 14 shows the experimental setup to determine whether anti-FcεRI mAB can modulate FcεRI.
Figure 15:
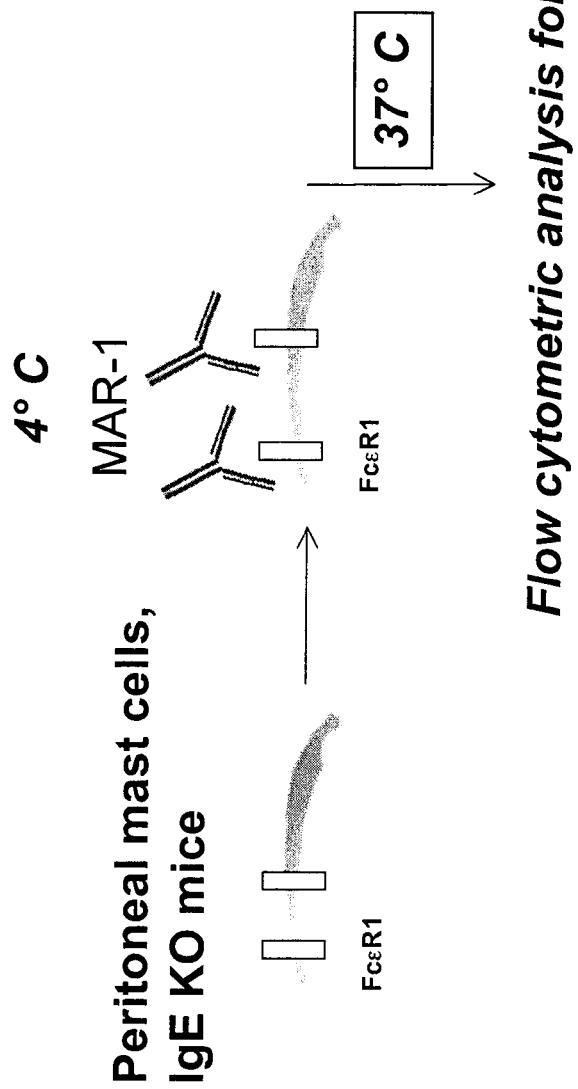
FIG. 15 shows the experimental setup to determine whether anti-FcεRI mAB can modulate Fcε receptor 1.
Figure 16:
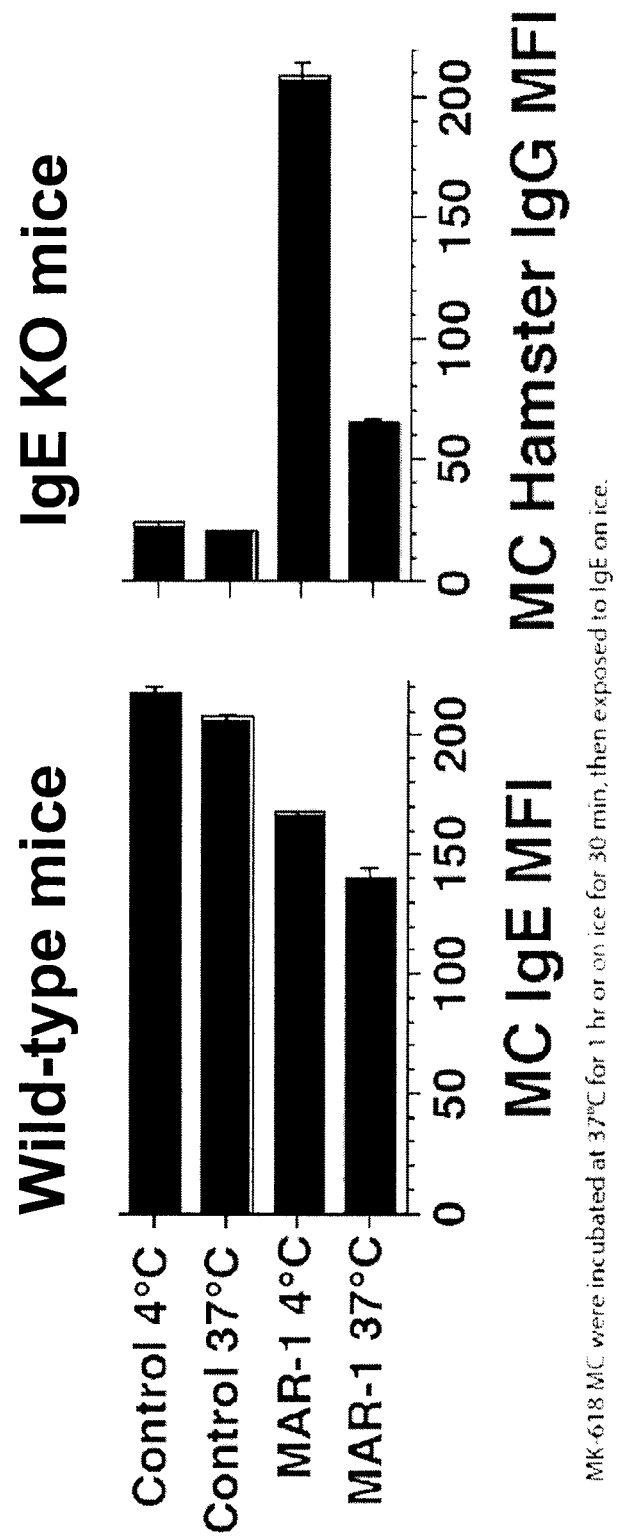
FIG. 16 shows that MAR-1 modulates FcεRI, but has limited ability to modulate FcεRI-bound IgE at 37° C.
Figure 17:
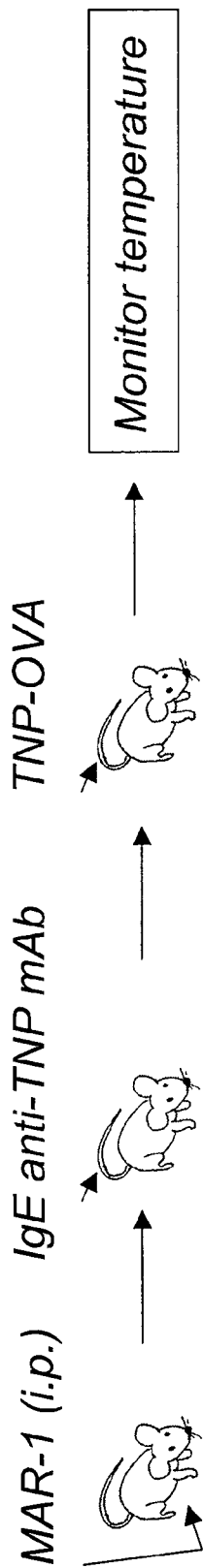
FIG. 17 shows intraperitoneal injection of MAR-1 followed by IgE anti-TNP mAB and TNP-OVA and monitoring of the mouse temperature.
Figures 18A, 18B:
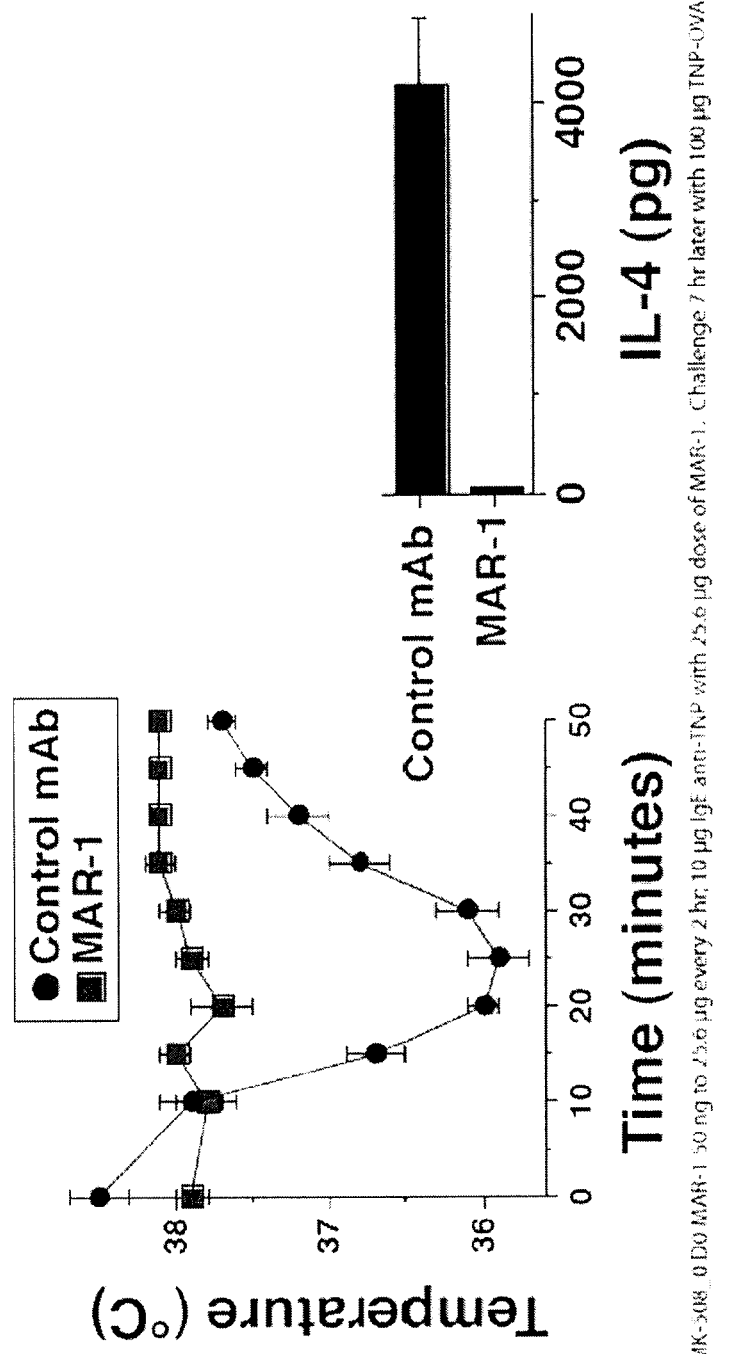
FIGS. 18A-B shows that pretreatment of MAR-1 blocks the ability of subsequent treatment with IgE anti-TNP mAB to prime for TNP-OVA-induced anaphylaxis and IL-4 production.
Figures 19A, 19B:
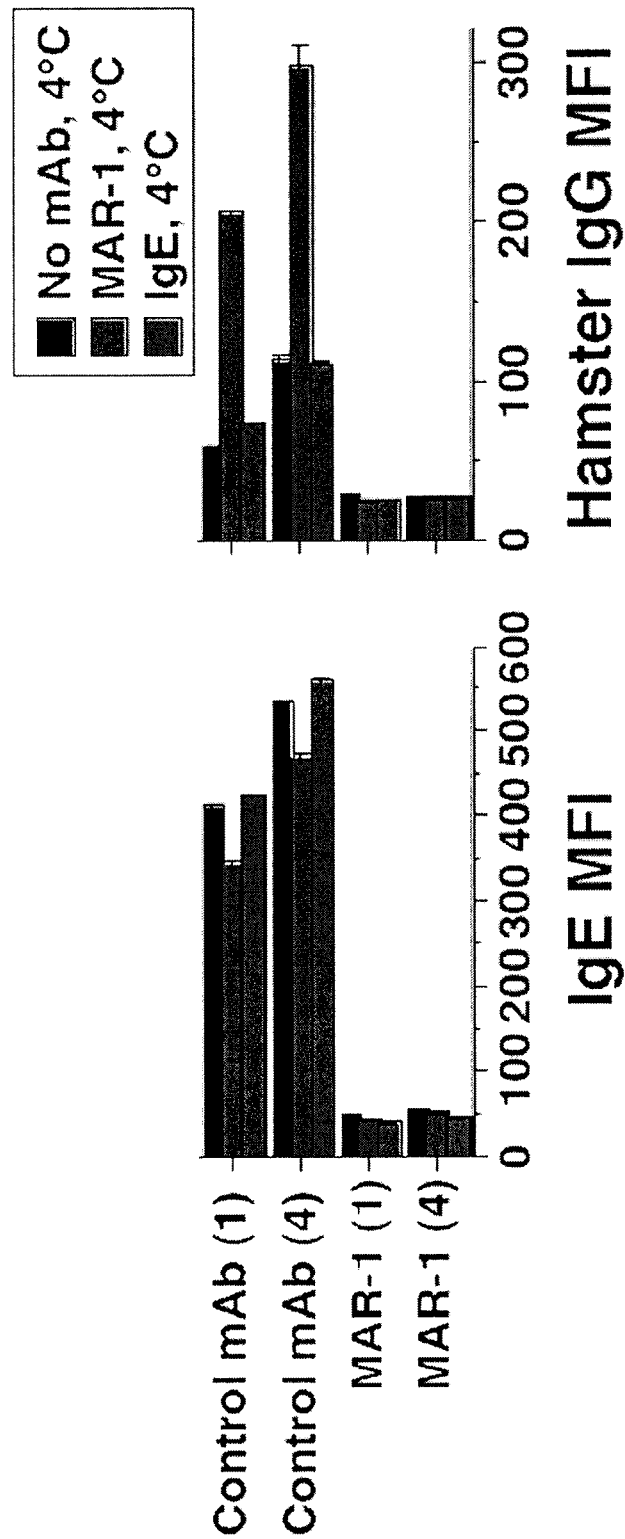
FIGS. 19A-B shows that in vivo treatment with MAR-1 for eight days eliminates most mast cell IgE and FcεRI.

FIGS. 6-8 show results of studies related to responses to TNP-OVA. FIGS. 9-13 show Mar-1-mediated blocking and displacement of IgE; Experimental setups and data. FIGS. 14-16 show anti-FcεRI mAB to modulate FcεRI and the Fcε receptor 1. FIGS. 17-19 show data related to analysis of whether Anti-FcεRI mAB (MAR-1) treatment can Prevent Anaphylaxis. Specific conclusions drawn include: Anti-FcεRI mAB (MAR-1) blocks binding of IgE to mast cells. Receptor bound IgE blocks MAR-1 binding to mast cells; MAR-1 has limited ability to displace mast cell-bound IgE; Mar-1 modulates FcεRI, but has limited ability to modulate FcεRI-bound IgE at 37° C.; Pretreatment with MAR-1 blocks the ability of subsequent treatment with IgE anti-TNP mAB to prime for TNP-OVA-induced anaphylaxis and IL-4 production.

Figure 20:
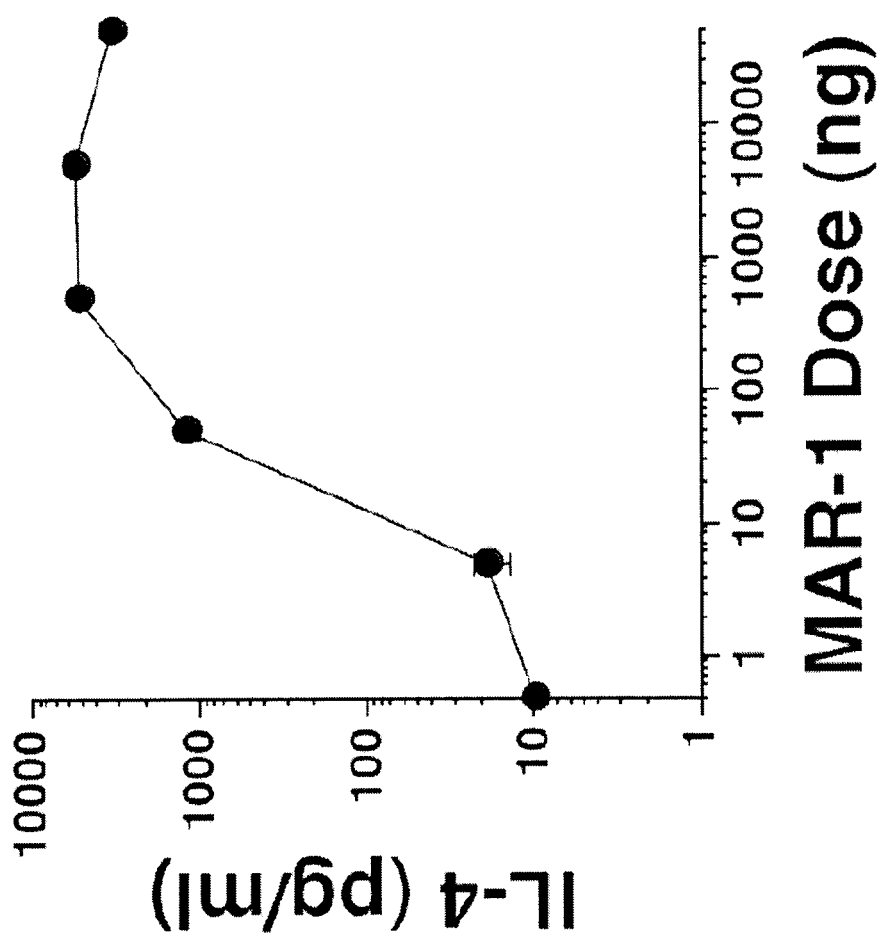
FIG. 20 shows anti-FcεRI mAB (MAR-1) induces a dose-dependent IL-4 response.
Figure 21:
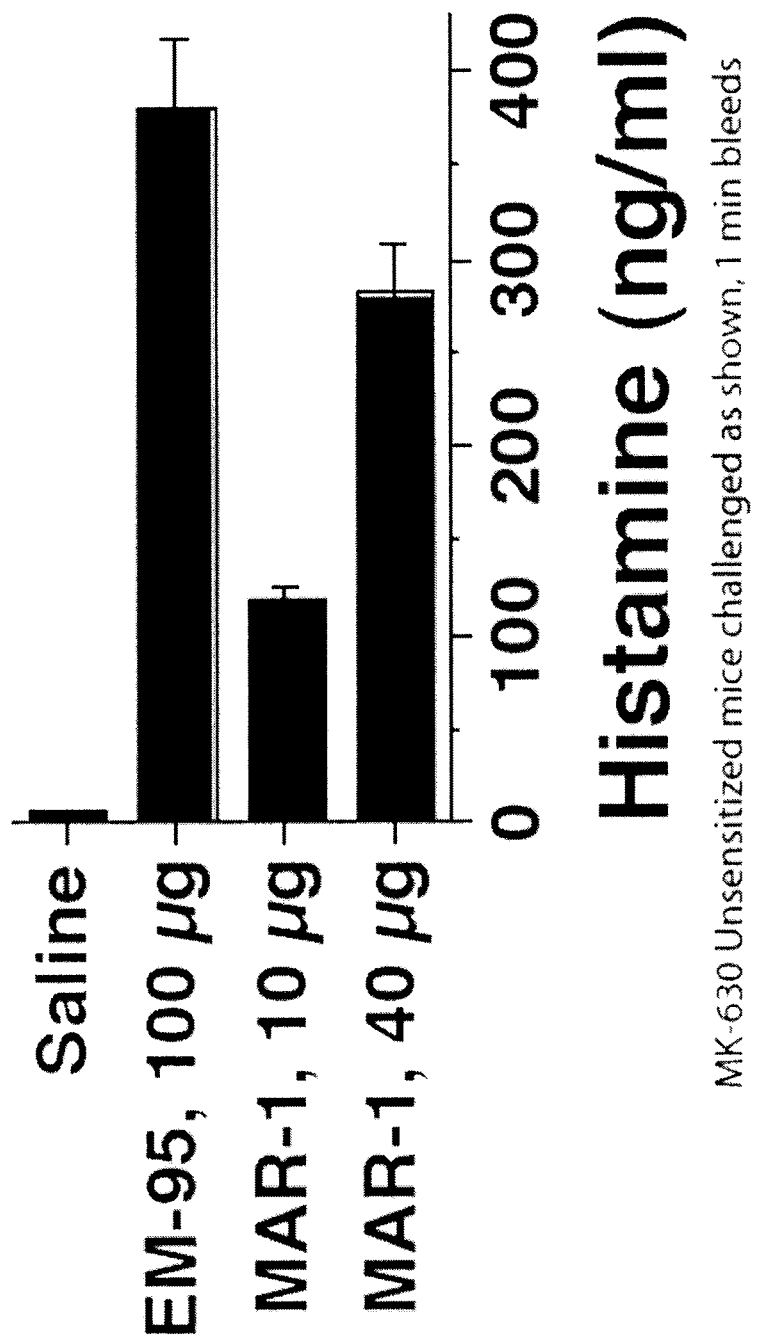
FIG. 21 shows that MAR-1 induces a dose-dependent histamine response.
Figure 22:
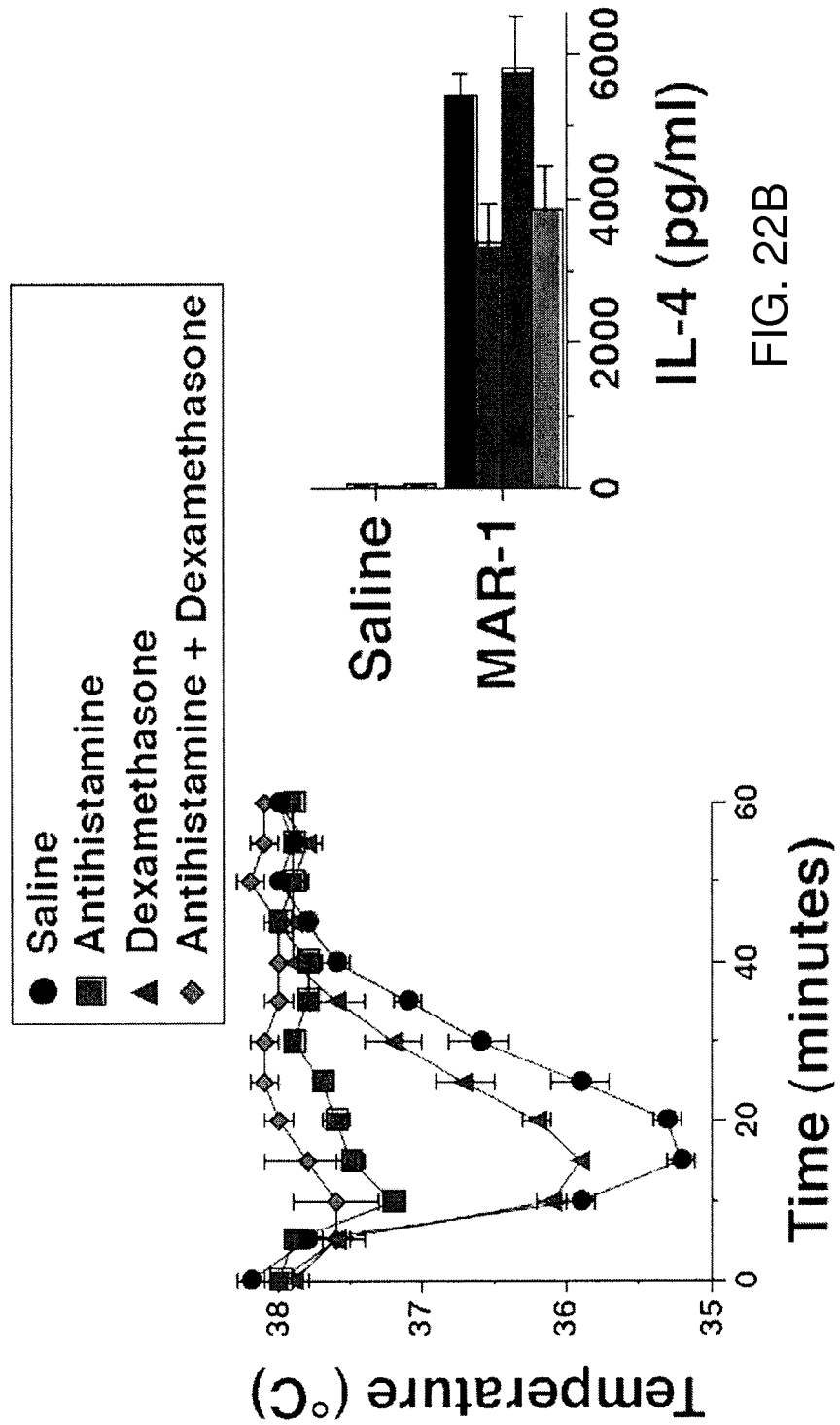
FIGS. 22A-B show that MAR-1 induces IL-4 and anaphylactic responses that are suppressed by antihistamine and corticosteroid pretreatment.
Figure 23:
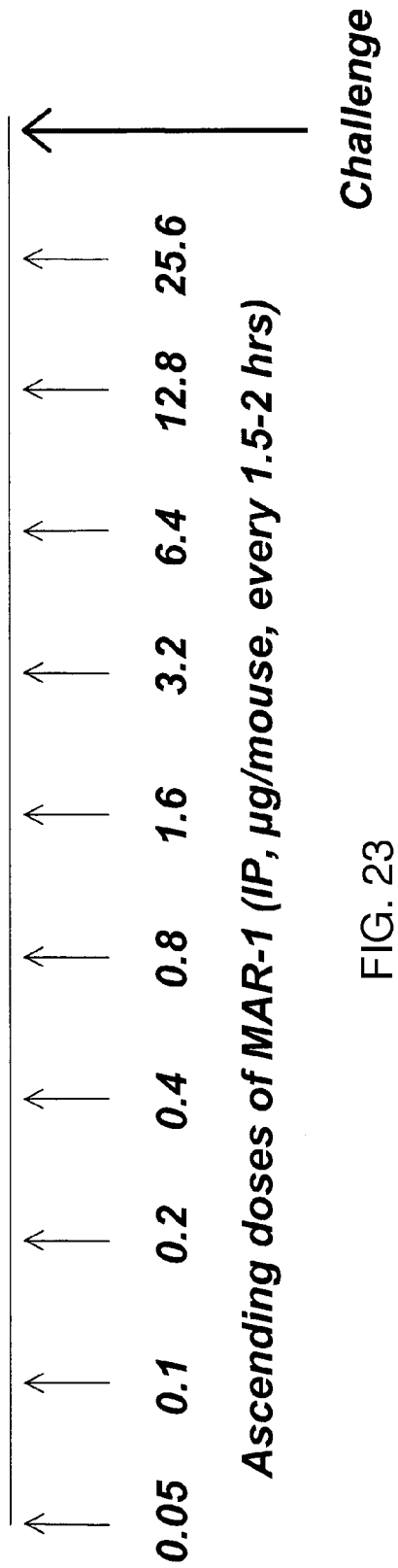
FIG. 23 shows an experimental setup to determine whether rapid desensitization with ascending doses of anti-FcεRI mAB can prevent anaphylaxis.
Figure 24:
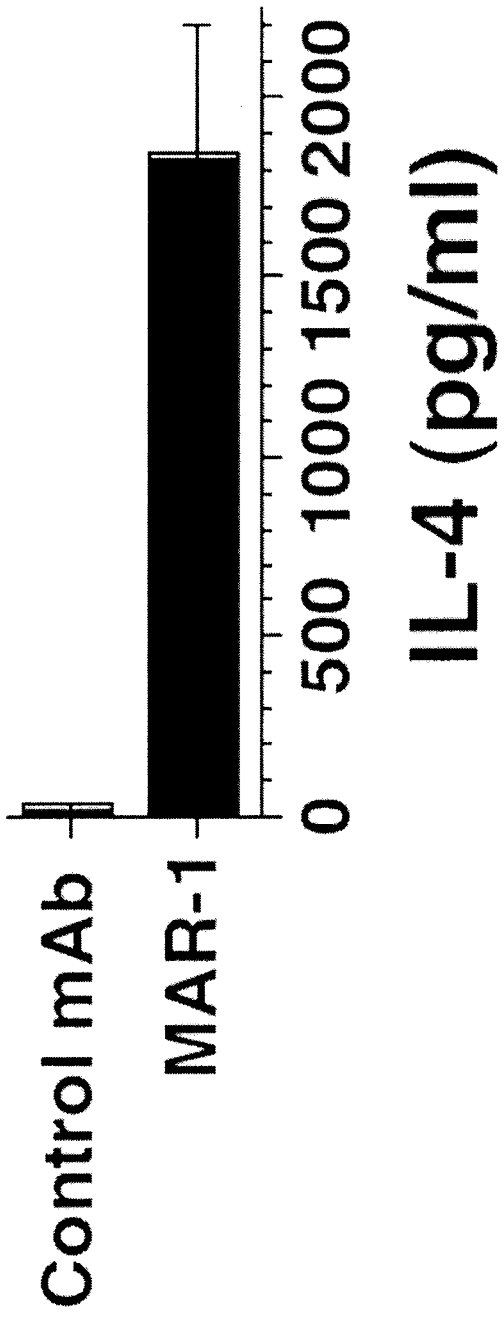
FIG. 24 shows that rapid desensitization with MAR-1 stimulates an IL-4 response.
Figures 25A, 25B:
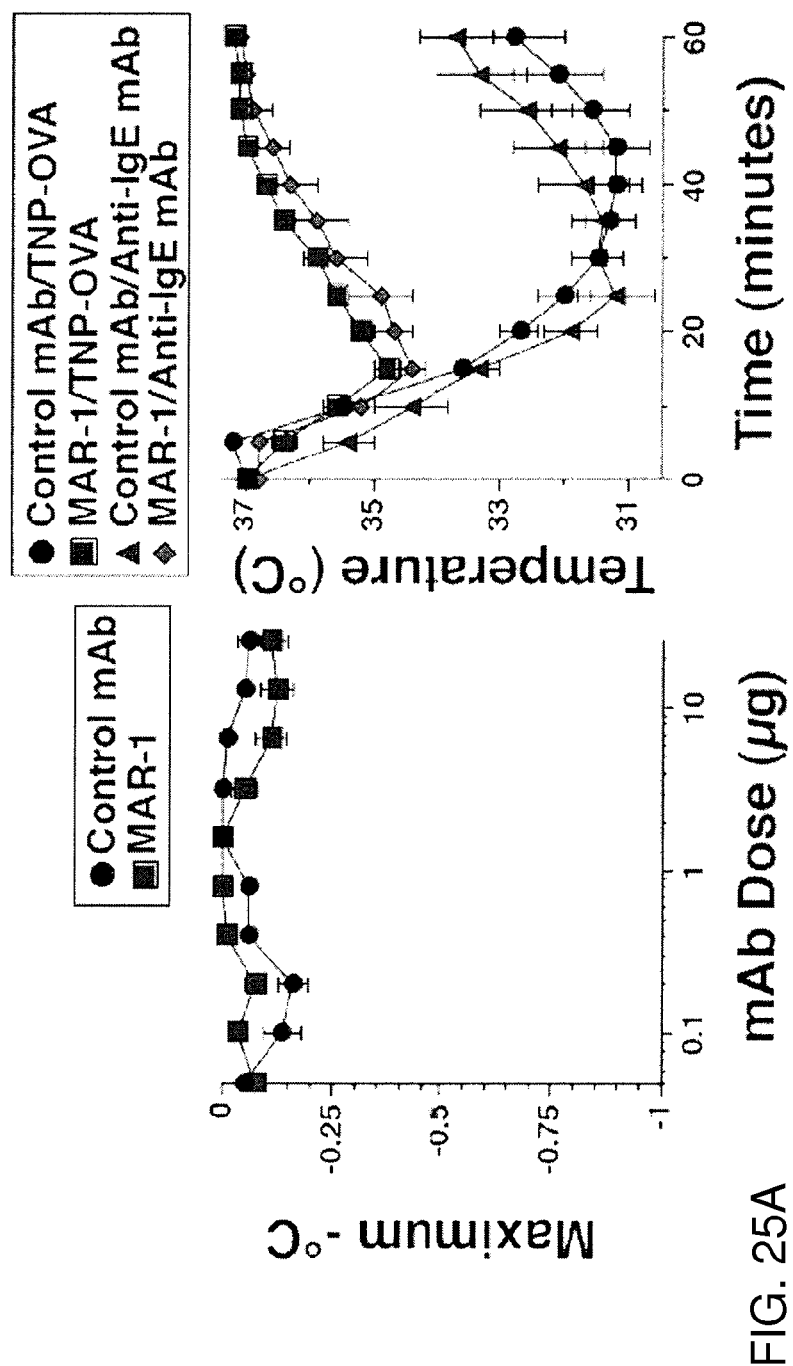
FIG. 25 A-B shows that rapid desensitization with escalating doses of MAR-1 prevents MAR-1-induced anaphylaxis and ameliorates IgE-mediated anaphylaxis induced by challenge two hours after completion of the desensitization protocol.

FIGS. 20-21 show data for analyzing whether Anti-FcεRI mAB treatment can induce anaphylaxis. FIG. 22 shows data for analyzing whether treatments with antihistamines and/or corticosteroids can prevent anti-FcεRI mAB-induced shock.

FIGS. 23-27 show data for analysis of rapid desensitization studies with anti-FcεRI mAB regarding anaphylaxis and IL-4. FIGS. 28-34 show data for studies of longer-term treatments with MAR-1 and anaphylaxis. Conclusions include: Anti-FcεRI (MAR-1) mAB is an activating antibody that induces IL-4, and MMCP1 production, as well as shock; Antihistamine and corticosteroid treatment can abrogate shock and diminish release of IL-4 induced by anti-FcεRI mAB; Rapid desensitization with ascending doses of MAR-1 prevents MAR-1-induced anaphylaxis, ameliorates IgE-mediated anaphylaxis induced by challenge 2 hrs later, as well as inhibits the IL-4 and MMCP1 responses to anti-IgE mAB; Rapid desensitization with MAR-1 fails to suppress the anaphylactic response to anti-IgE Mab 70 hours later; thus desensitization reflects recent activation; Treatment with MAR-1 for 2-8 days inhibits anti-IgE mAB-induced IL-4, IL-13, and MMCP1 responses, but not shock; Treatment with MAR-1 for 22 days blocks IL-4, IL-13, MMCP1, and shock induced by TNP-OVA challenge of IgE anti-TNP mAB-primed mice and inhibits shock induced by anti-IgE mAB; Treatment with MAR-1 for 22 days synergizes with antihistamine treatment and completely blocks the anaphylactic response to anti-IgE mAB.

FIG. 35 show data for studies analyzing whether treatment with mAB against human FcεRI can prevent allergy and anaphylaxis. More specifically FIG. 35 shows graphs of studies with a model planned to determine whether anti-human FcεRI mABs can be used for desensitization, and more specifically show that anti-human FcεRI mAB induces IL-4 and MMCP1 responses and anaphylaxis in human IgE-primed huFcεRI transgenic mice. Regarding anti-FcεRI as a prophylactic against anaphylaxis: Anti-FcεRI mAB can induce anaphylaxis but also can prevent IgE-mediated anaphylaxis through two mechanisms: 1) desensitization (rapid onset, short-lived); 2) modulating FcεRI and preventing IgE binding (slow onset, probably lasts as long as anti-FcεRI mAB is present). Proven methods for preventing anaphylaxis induction by initial treatment with anti-FcεRI mAB: 1) rapid desensitization; 2) anti-histamine plus dexamethasone. Potential methods for preventing anaphylaxis induction by initial treatment with anti-FcεRI mAB: 1) treat with Fab or Fv (univalent) fragment of anti-FcεRI mAB prior to injection of intact anti-FcεRI mAB; 2) treat with high dose of IgE prior to injection of intact anti-FcεRI mAB; 2) treat with high dose of IgE prior to injection of intact anti-FcεRI mAB.

FIG. 36 Mice can be desensitized to IgE-mediated anaphylaxis by rapid desensitization with an activating anti-IgE mAb. A. In 3 separate experiments, BALB/c mice (4/group in this and other figures unless otherwise noted) that had been injected with 10 μg of IgE anti-TNP mAb were treated every 90 min with doubling or tripling doses of anti-IgE mAb (EM-95), starting with 50 ng, then challenged the next day i.v. with 10 μg of TNP-BSA or TNP-OVA. Rectal temperatures were determined during the 60 min after the 10 μg challenge. Means of maximum decreases in temperature±SEs are shown. B. In the same 3 experiments, BALB/c mice were serially injected i.v. every 90 min with doses of EM-95 that were 2-3-fold higher than the preceding dose, starting at a dose of 50 ng. The lowest temperature after each dose is shown. These observations demonstrate that while mice can be rapidly desensitized with anti-IgE mAb, this process carries the risk of inducing mild anaphylaxis.

Figure 37:
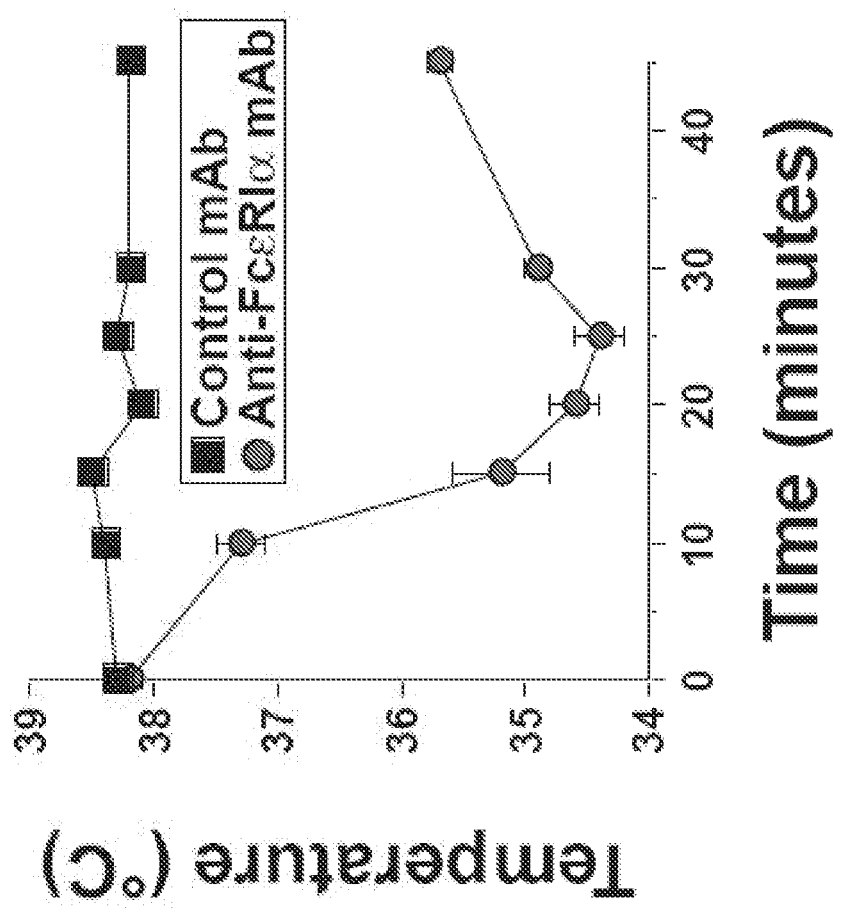
FIG. 37 shows a graph indicating that injection of mice with anti-FcεRIα monoclonal antibody induces anaphylaxis.
Figure 38A:
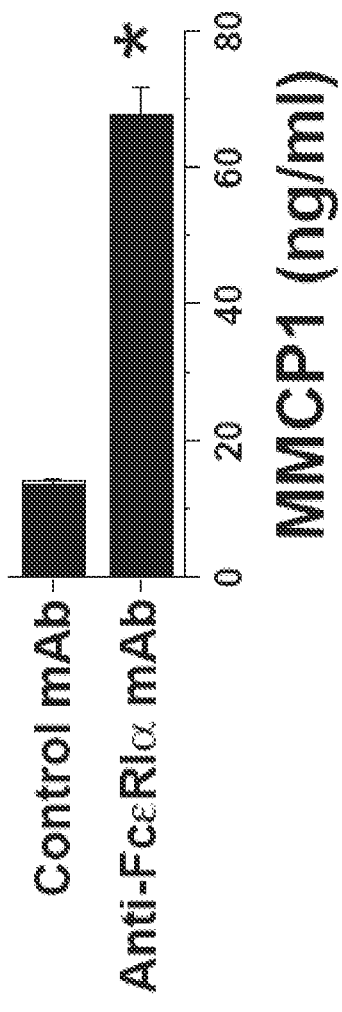
FIGS. 38A-B show graphs indicating that anti-FcεRIα monoclonal antibody induces mast cell degranulation, with increases in serum levels of mouse mast cell protease 1 (MMCP1).
Figure 38B:
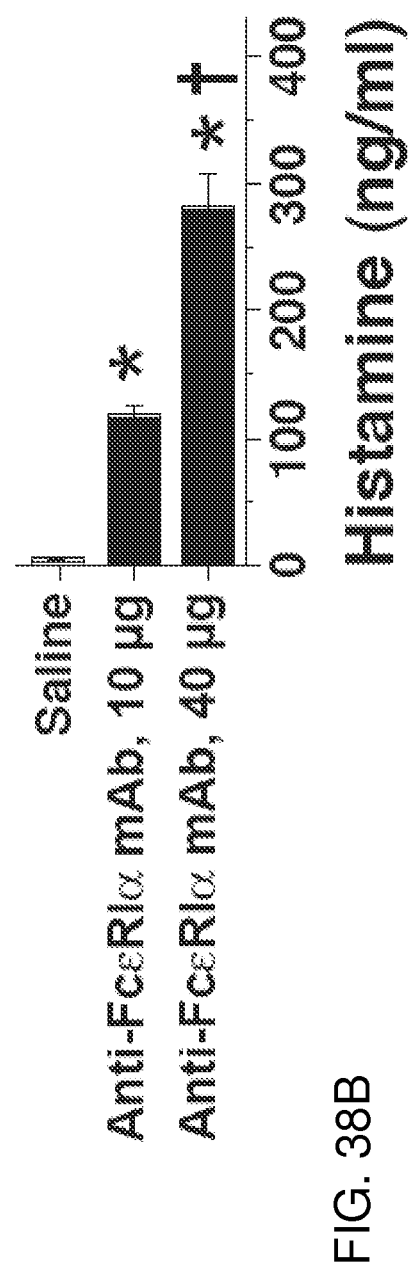
Figures 39A, 39B:
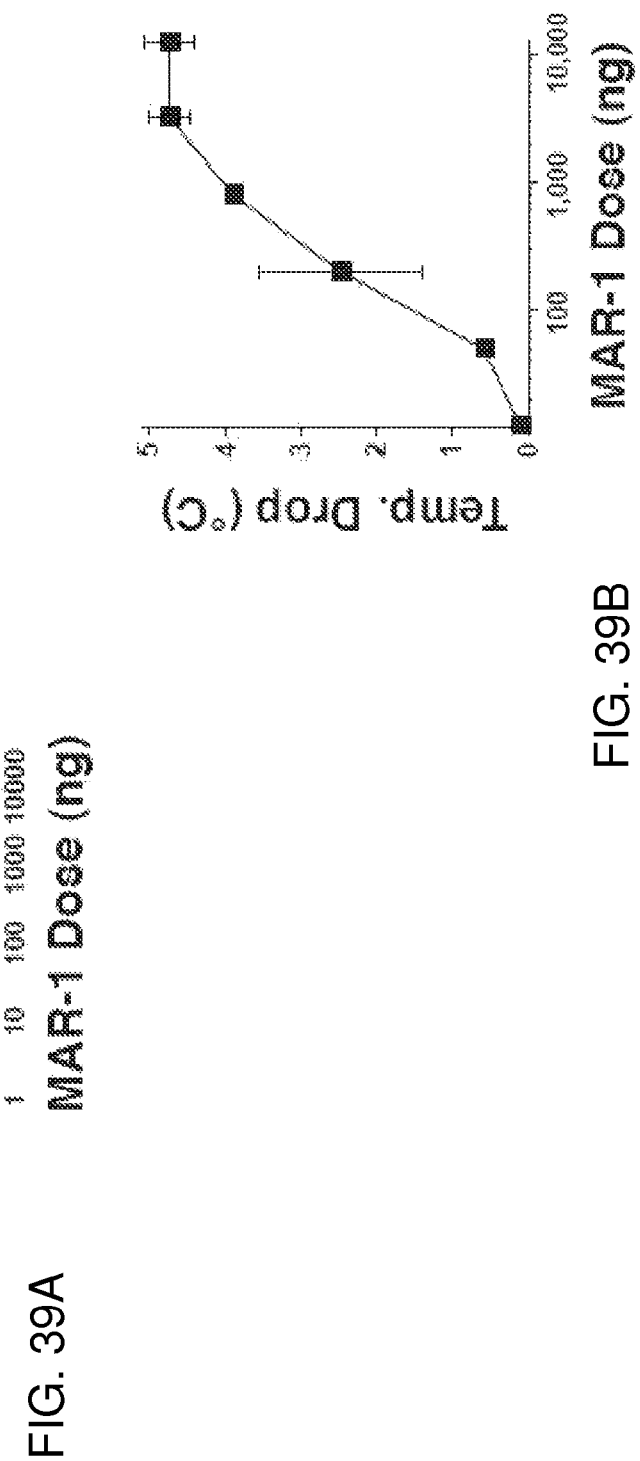
FIGS. 39A-B show that injection of mice with anti-FcεRIα monoclonal antibody (MAR-1) induces dose-dependent increases in IL-4 production and hypothermia.

FIG. 37 Injection of mice with anti-FcεRIα monoclonal antibody induces anaphylaxis. BALB/c mice were injected i.v. with 50 μg of hamster anti-mouse FcRI-mAb (MAR-1) or a hamster IgG control mAb. Rectal temperature was followed for 45 min. The data demonstrates that a monoclonal antibody to FcεRIα can induce anaphylaxis. While not desiring to be bound by theory, it is believed this is accomplished by crosslinking this receptor on mast cells.

FIG. 38 Anti-FcεRIα mAb induces mast cell degranulation, with increases in serum levels of mouse mast cell protease 1 (MMCP1) and histamine. A. MMCP1 in serum 4 hr after mAb injection. B. Histamine in serum 5 min after mAb injection. Concentrations were determined by ELISA. These observations demonstrate that anaphylaxis induced by injecting mice with anti-FcεRIα mAb is accompanied by (and likely caused by) mast cell degranulation. The asterisk and dagger denote statistical significance and compared to control mAb or saline.

FIG. 39 Injection of mice with anti-FcεRIα mAb (MAR-1) induces dose-dependent increases in IL-4 production and hypothermia. BALB/c mice were injected with a single dose of MAR-1 at the doses shown. IL-4 secretion during the 4 hr after mAb injection (A) was determined by the in vivo cytokine capture assay (IVCCA). Shock, as identified by hypothermia, was determined by repeated rectal temperatures over a period of 1 hr, with the average maximum decrease for each mouse shown (B). Results demonstrate that a lower dose of MAR-1 is required to activate basophils to secrete IL-4 than to induce sufficient mast cell degranulation to cause shock.

Figure 40B:
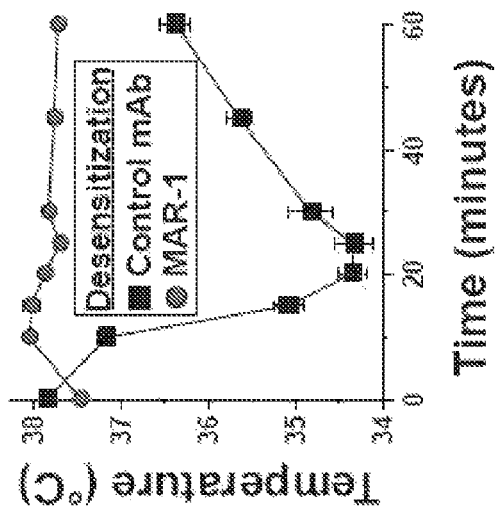

FIG. 40 Repeated injection of serially increasing doses of MAR-1 prevents the development of an anaphylactic response to this mAb. A. BALB/c mice were serially injected i.p. every 60-90 min with the doses of MAR-1 or control mAb shown, starting with 100 ng. The mean maximum decrease in temperature±SE during the 60 min after each injection is shown. B. Mice treated as in panel A were challenged i.v. with 50 μg of MAR-1. Rectal temperatures were followed for the next 60 minutes. Results show that mice can be safely and rapidly desensitized to MAR-1 by the same procedure that has been classically used for desensitizing mice to an allergen.

Figure 41:
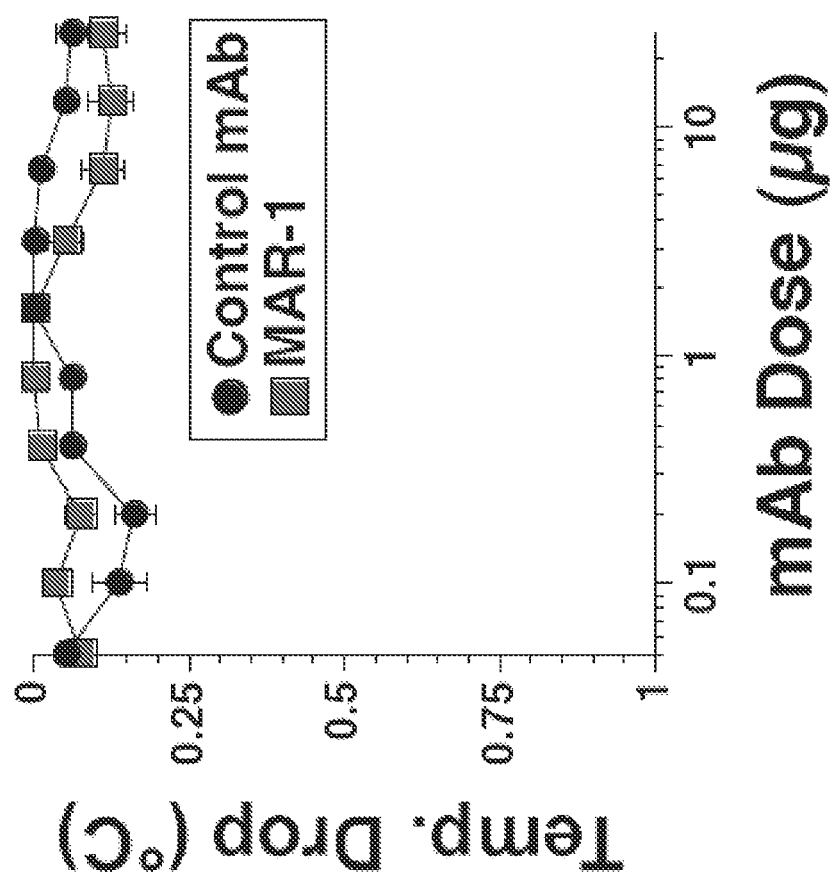
FIG. 41 shows that rapid desensitization with MAR-1 fails to induce shock (hypothermia) even when mice have been made more sensitive to vasoactive mediators by pretreatment with a long-acting formulation of IL-4 (IL-4C).

FIG. 41 Rapid desensitization with MAR-1 fails to induce shock (hypothermia) even when mice have been made more sensitive to vasoactive mediators by pre-treatment with a long-acting formulation of IL-4 (IL-4C). Mice were injected i.p. with IL-4C containing 2 μg of IL-4. The next day, these mice were serially injected i.p. every 60-90 min with the doses of MAR-1 or control mAb shown, starting with 100 ng. The mean maximum decrease in temperature±SE during the 60 min after each injection is shown. The data demonstrates that rapid desensitization of mice with MAR-1 is safe even when mice have had their sensitivity to mast cell-generated mediators increased several fold by injection of IL-4C.

FIG. 42 The anaphylactic response to MAR-1 (anti-FcεRIα mAb) can be inhibited by pretreatment with an antihistamine or a corticosteroid. Mice were injected i.v. with a single 50 μg dose of MAR-1 45 minutes after pretreatment with saline, antihistamine (triprolidine), dexamethasone, or antihistamine plus dexamethasone. Rectal temperatures were determined during the subsequent 60 min. Results demonstrate that mice can be protected by antihistamine and corticosteroids against anaphylaxis induced by MAR-1 crosslinking of FcεRI.

FIG. 43 MAR-1 anti-FcεRIα mAb and mouse IgE each blocks the others binding to FcεRI. Peritoneal mast cells from IgE-deficient mice were incubated on ice with IgE-TNP mAb or control mAb, then stained for IgE (upper bars) or incubated on ice with MAR-1 and stained for hamster IgG (lower bars). Cells were analyzed for surface fluorescence.

These observations demonstrate that IgE and MAR-1 each blocks the binding of the other to FcεRI. Consequently, MAR-1 has no ability to directly affect mast cell or basophil FcεRI that has bound IgE. The asterisk and dagger denote statistical significance of the difference between the control mAb and IgE αTNP mAb groups.

Figure 44:
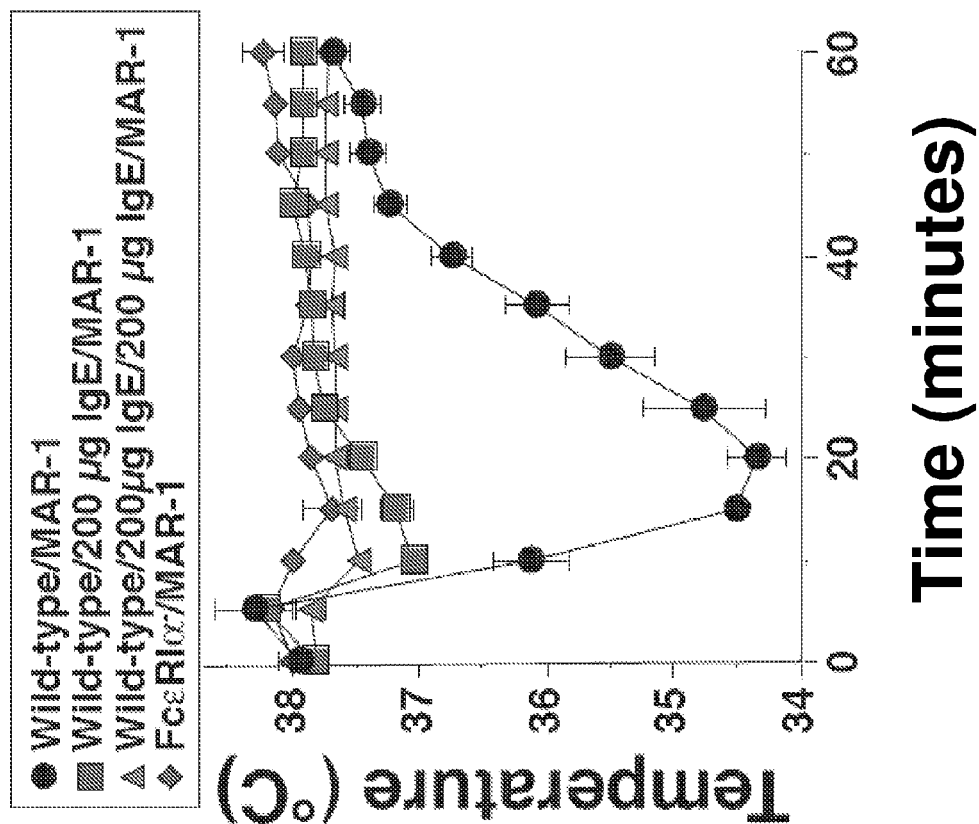
FIG. 44 shows that in vivo treatment with IgE blocks the ability of MAR-1 anti-FcεRIα monoclonal antibody to induce anaphylaxis.

FIG. 44 In vivo treatment with IgE blocks the ability of MAR-1 anti-FcεRIα mAb to induce anaphylaxis. WT and FcRIα-deficient (FcεRIα-) mice were injected i.v. with saline, once with mouse IgE (reg squares), or twice with IgE (blue triangles) then challenged i.v. with MAR-1. Rectal temperatures were determined. The data show that IgE pre-treatment blocks the ability of MAR-1 to induce anaphylaxis, presumably by occupying all mast cell FcRIα molecules so that MAR-1 cannot bind to these molecules.

FIG. 45 Treatment of mice with IgE inhibits the ability of MAR-1 anti-FcεRIα mAb to induce an IL-4 response. In the same experiment shown in FIG. 9, IL-4 secretion was determined by IVCCA for 4 hr following challenge with 40 μg of MAR-1. The data show that pretreatment with IgE inhibits the ability of MAR-1 to induce a basophil-derived IgE response, although not as completely as this pretreatment was able to suppress anaphylaxis (see FIG. 9).

FIG. 46 Treatment of mast cells with MAR-1 anti-FcεRIα mAb only slowly decreases IgE expression in vitro. Peritoneal mast cells from wild-type BALB/c mice were cultured for 1 hr at 4° C. or 37° C. with 50 μg of concentration of MAR-1 or control mAb, then stained for IgE and analyzed by flow cytometry.

Figure 47:
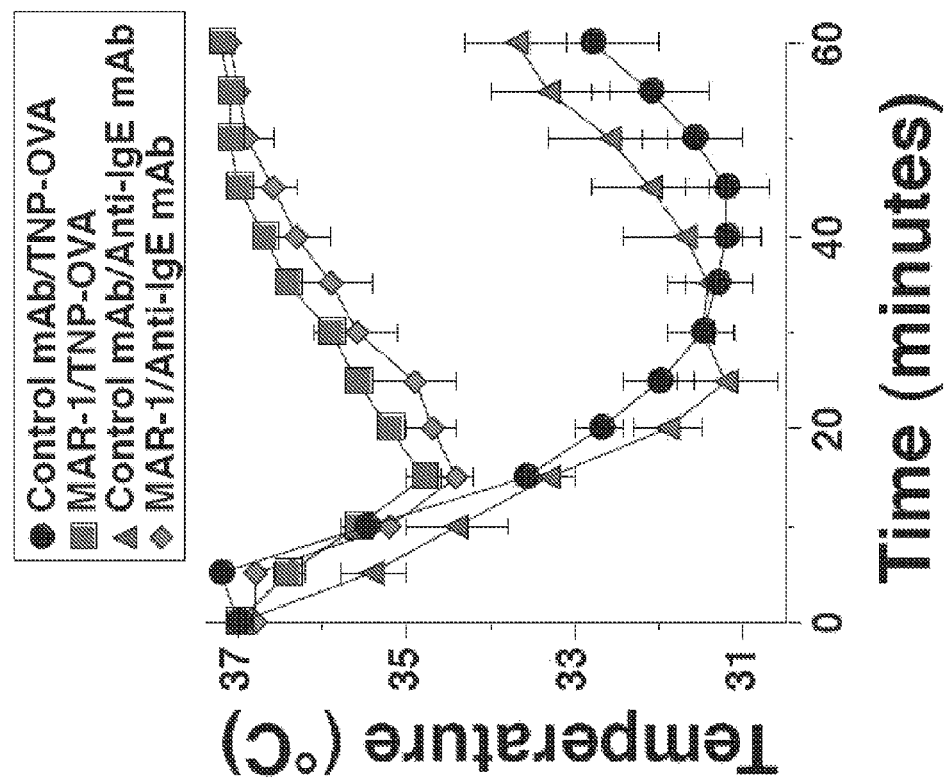
FIG. 47 is a graph showing that rapid desensitization with MAR-1 reduces responsiveness to cross-linking of mast cell FcεRI by antigen and anti-IgE monoclonal antibody.

FIG. 47 Rapid desensitization with MAR-1 reduces responsiveness to crosslinking of mast cell FcεRI by antigen and anti-IgE mAb. BALB/c mice were injected i.v. with 10 μg of IgE anti-TNP mAb, then rapidly desensitized with MAR-1 or control mAb. Mice were injected i.v. with TNP OVA or EM-95 2 hr after the last MAR-1 or control mAb dose. Rectal temperatures were determined. Because rapid desensitization with MAR-1 fails to remove most mast cell IgE within this time frame, these observations indicate that MAR-1 rapid desensitization decreases mast cell responsiveness to FcεRI crosslinking.

FIG. 48 Rapid desensitization with MAR-1 decreases mast cell MMCP1 secretion and basophil IL-4 secretion. Serum MMCP1 and IL-4 production in response to anti-IgE mAb challenge following MAR-1 desensitization were evaluated in the same experiment shown in FIG. 12. Results demonstrate that rapid desensitization decreases the responsiveness of both mast cells and basophils. Daggers denote statistically significant difference between the groups that were or were not pre-treated with MAR-1.

FIG. 49 Reduced responsiveness induced by desensitization of mast cells with MAR-1 anti FcεRIα mAb is lost within 48 hours despite the continued presence of MAR-1. BALB/c mice were rapidly desensitized with MAR-1 or control mAb and injected daily i.p. with MAR-1 or control mAb for 2 days, then injected i.v. with anti-IgE mAb. Rectal temperatures were determined. Taken together with the data shown in FIG. 12, this observation suggests that the initial decrease in mast cell responsiveness caused by MAR-1 rapid desensitization results from subclinical mast cell activation rather than from removal of mast cell IgE. This decreased responsiveness is lost when the MAR-1-induced decrease in mast cell FcεRI that is not bound by IgE prevents further mast cell activation by MAR-1.

Figure 50A:
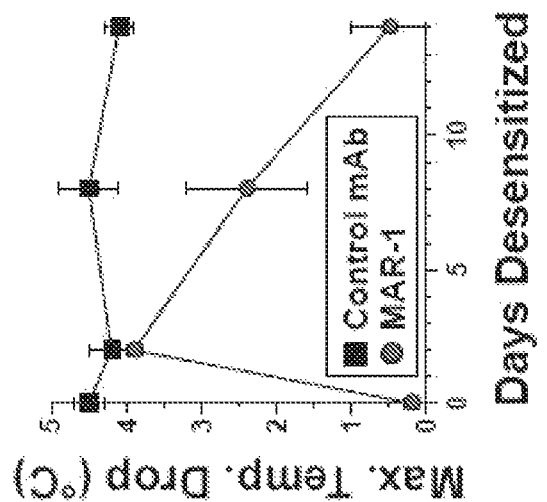
FIGS. 50A-B show that chronic treatment with MAR-1 anti-FcεRIα monoclonal antibody blocks the ability of antigen to induce IgE-mediated anaphylaxis.
Figure 50B:
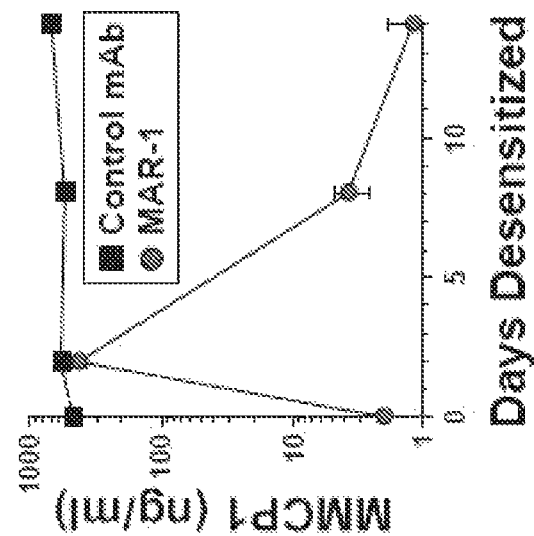

FIG. 50 Chronic treatment with MAR-1 anti-FcεRIα mAb blocks the ability of antigen to induce IgE-mediated anaphylaxis. BALB/c mice were injected i.p. with 10 μg of IgE anti-TNP mAb on day −1. Mice were rapidly desensitized with MAR-1 or treated with equal doses of normal hamster IgG on day 0, 18 hours after the initial dose of IgE anti-TNP mAb. Mice were re-injected with 10 μg of IgE anti-TNP mAb on days 2, 5, 8 and 11 and with 50 μg of MAR-1 or control mAb on days 3, 6, 9 and 12. The maximum decrease in rectal temperature (A) and the serum MMCP1 level 4 hr following challenge i.v. with 50 μg of TNP-OVA (B) are shown for mice challenged 2 hr or 2, 4, 8, or 14 d after desensitization. Data indicates that MAR-1 desensitizes mast cells through 2 distinct mechanisms: a rapid, short-lived decrease in responsiveness to FcεRI crosslinking that results from activation-induced desensitization and a slow, long-lived decrease in responsiveness that results from the loss of mast cell FcεRI-associated IgE.

FIG. 51 Rapid desensitization with MAR-1 does not induce decreased responsiveness to mast cell-produced vasoactive mediators. BALB/c mice were left untreated or were rapidly desensitized with MAR-1. Two hours later, both sets of mice were injected i.v. with 3.5 mg of histamine or 500 ng of PAF. Rectal temperatures were determined. Results demonstrate that the decreased responsiveness to anti-IgE or antigen that is induced by rapid desensitization results from decreased mast cell mediator production rather than from decreased responsiveness to mast cell-produced mediators.

Figure 52A:
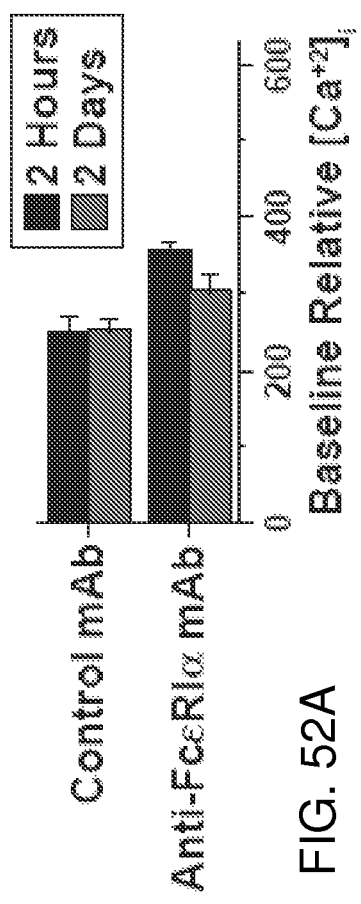
FIGS. 52A-B show that rapid desensitization with MAR-1 anti-FcεRIα monoclonal antibody temporarily reduces the mast cell calcium response to FcεRIα crosslinking.
Figure 52B:
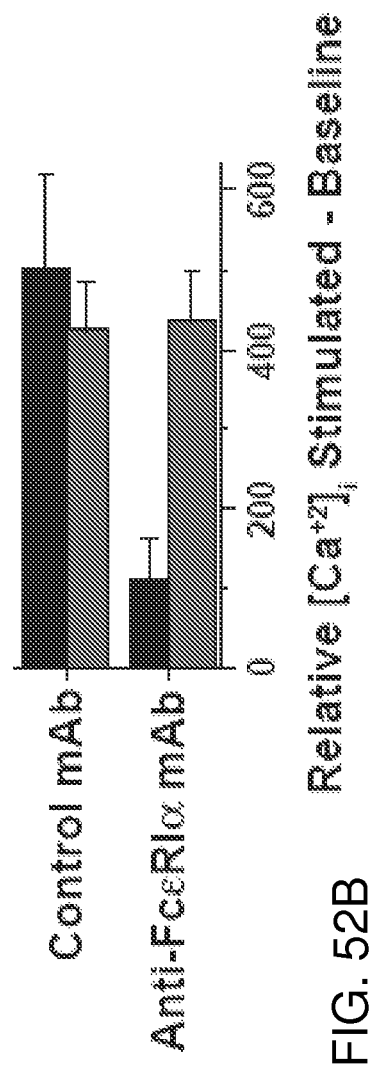

FIG. 52 Rapid desensitization with MAR-1 anti-FcεRIα mAb temporarily reduces the mast cell calcium response to FcεRIα crosslinking. Peritoneal wash cells from mice rapidly desensitized with MAR-1 or control mAb 2 hr or 2 d prior to cell collection were loaded with Fluo-4 (Invitrogen). Relative levels of intracellular Ca++ ([Ca+2]i) were determine at baseline and immediately after in vitro challenge with anti-IgE mAb. These observations directly demonstrate that rapid desensitization with MAR-1 decreases the signaling response to FcεRI crosslinking for a limited period of time.

Figure 53A:
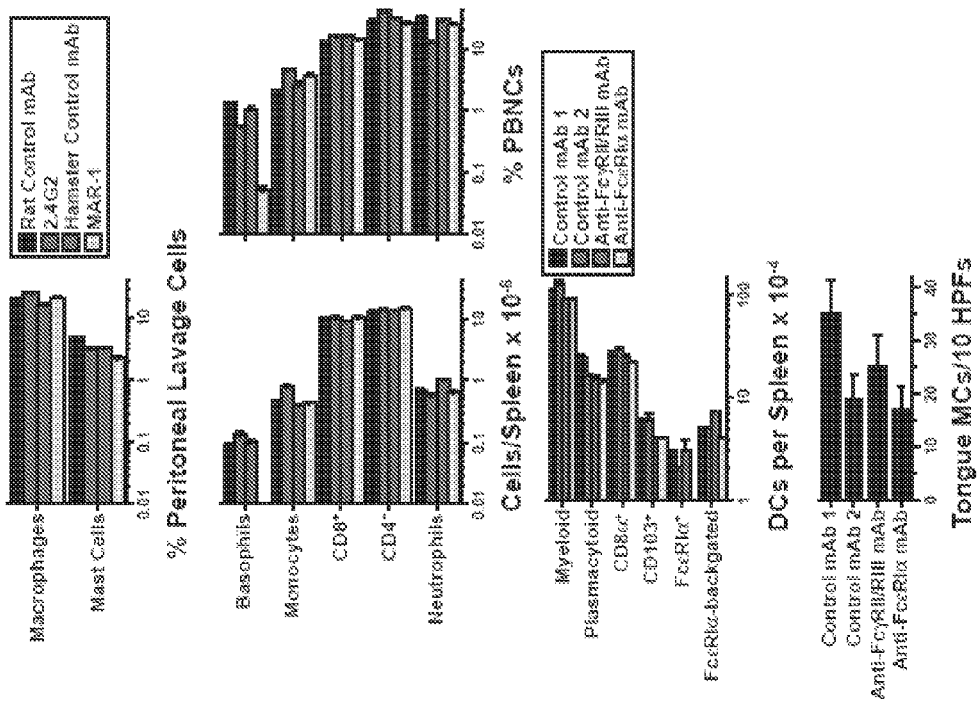

FIG. 53 Rapid desensitization with MAR-1 anti-FcεRIα mAb causes loss of basophils, but not other cell types. A and B. BALB/c mice were rapidly desensitized i.p. with MAR-1 anti-FcεRIα mAb or 2.4G2 anti-FcγRIIb/RIII mAb or injected i.p. with equal doses of isotype matched control mAbs. Mice were re-injected with full doses of the same mAbs 3 times a week. Flow cytometry was used to determine numbers of different cell types in peritoneal lavage, spleen and peripheral blood (PBNCs) 3 and 17 days after the initial injection. Numbers of tongue mast cells were determined by staining tongue sections with Leder stain (Naphtol AS-D Chloroacetate) and counting positive cells by microscopic examination. C. The effect of anti-IgE mAb treatment on numbers of blood basophils and peritoneal lavage mast cells was determined 3 days after rapid desensitization with anti-IgE mAb EM-95). The results of these studies demonstrate that: 1) MAR-1 depletes basophils, but not other cell types; and 2) anti-IgE mAb does not deplete basophils. The difference in the MAR-1 anti-FcεRIα mAb and EM-95 anti-IgE mAb effects on basophils may reflect a requirement for continuing FcεRI signaling to deplete basophils: MAR-1 can continue to signal to some extent as basophils re-express FcεRI on their membranes, while IgE will not be re-expressed on basophil membranes after its initial modulation because EM-95 will bind to serum IgE before serum IgE can bind to basophil FcεRI.

FIG. 54 Eight days of in vivo treatment with MAR-1 anti-FcεRIα mAb removes most mast cell IgE. WT BALB/c mice were treated every 2 days for 8 days with 40 μg of MAR-1 or control mAb. Peritoneal mast cells were then incubated for 30 min on ice with no mAb, MAR-1 (12.5

µg/ml) or IgE anti-TNP mAb (12.5 µg/ml), then stained for IgE or hamster IgG. Average mean fluorescence is shown. The ability of MAR-1 (hamster IgG anti-mouse FcεRIα mAb) treatment to block staining for IgE and for hamster IgG demonstrates that MAR-1 eventually removes nearly all IgE and FcεRI from mast cells and does not merely bind to FcεRI and prevent its binding of IgE. Asterisks denote a significant increase as compared to the other control mAb treated groups. A dagger denotes a significant decrease as compared to the corresponding control mAb-treated group.

FIG. 55 High serum levels of IgE do not prevent the ability of MAR-1 to decrease mast cell IgE expression or deplete basophils in vivo. A. IL-4 transgenic (TG.UG) mice and ovalbumin (OVA)-immunized wild-type (WT) mice both have considerably increased serum IgE levels. B. WT, TG.UG and OVA-immune mice were left untreated or injected i.v. with 40 µg of MAR-1 anti-FcRIα mAb. Peritoneal mast cells obtained prior to or 1 or 4 days after MAR-1 injection were stained for IgE and analyzed by flow cytometry. Peripheral blood was analyzed for percent basophils. Results indicate that high serum levels of IgE do not prevent MAR-1 killing of basophils and delay, but do not prevent MAR-1 depletion of mast cell-associated IgE. Asterisks denote a significant increase as compared to wild-type mice. Daggers denote a significant decrease as compared to the untreated groups.

FIG. 56 MAR-1 accelerates the loss of FcεRI-bound IgE from mast cells. IgE-deficient mice were injected i.v. with 500 µg of anti-CD23 mAb (which prevents the binding of IgE to the B cell IgE receptor), then with 5 µg of IgE anti-TNP mAb. The next day, mice were injected with 50 µg of MAR-1 or control mAb. Peritoneal mast cells obtained prior to or 1 or 4 days after MAR-1 or control mAb injection were analyzed for membrane IgE. Results demonstrate that even though MAR-1 cannot bind to FcεRI that is IgE-bound, it increases the rate of loss of mast cell IgE/FcεRI complexes, possibly by increasing the rate of turnover of FcεRI. Daggers denote a significant decrease as compared to the control group.

Figure 57:
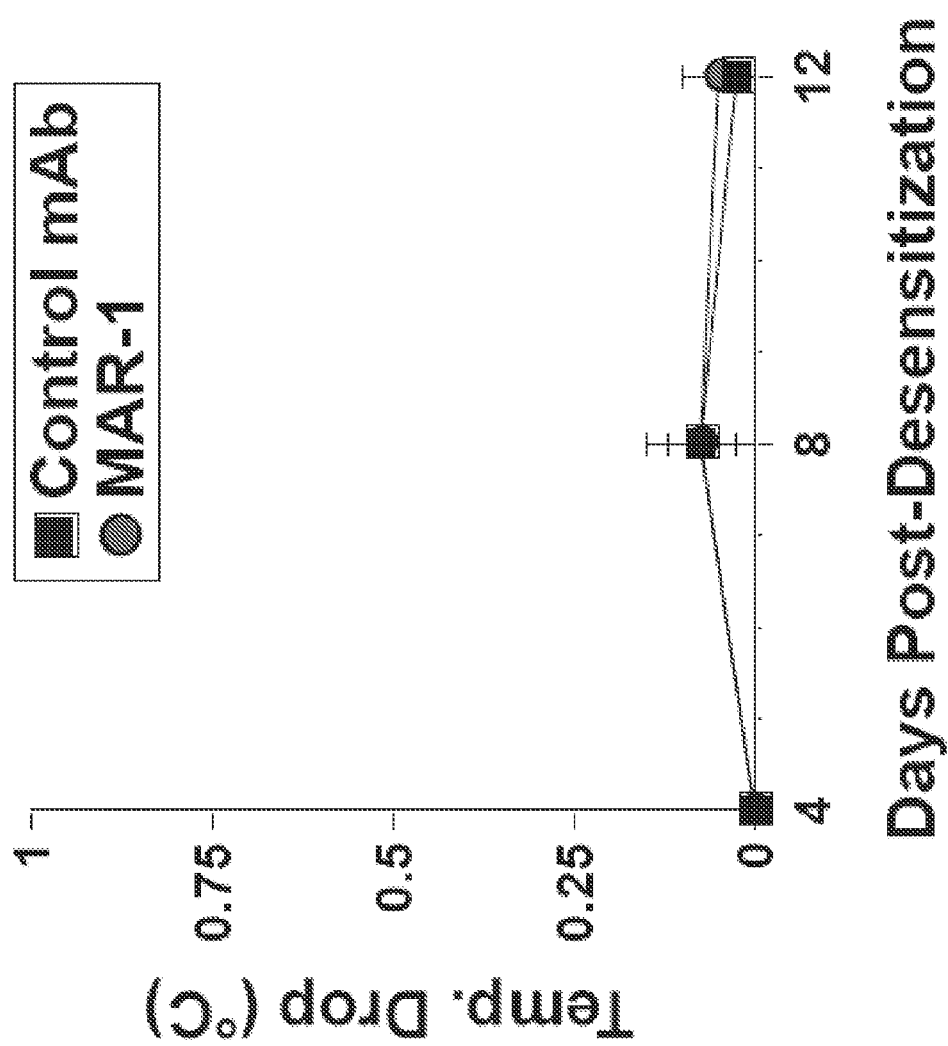
FIG. 57 is a graph showing that repeated injections of MAR-1 do not induce anaphylaxis in MAR-1-desensitized mice.

FIG. 57 Repeated injections of MAR-1 do not induce anaphylaxis in MAR-1 desensitized mice. WT BALB/c mice were rapidly desensitized with MAR-1 or control mAb, then injected i.p. with 50 µg of the same mAb on days 3, 6 and 9. Rectal temperatures were obtained for 1 hr after each repeated mAb dose. Means and SEs of temperatures after each dose are shown. These results demonstrate the safety of repeated MAR-1 injections of mice that have been rapidly desensitized with this mAb. The failure of repeated MAR-1 injections to induce anaphylaxis probably is due to the long in vivo half-life of this mAb. That is, MAR-1 is still present from a previous injection when a later injection is given. As a result, there is no unbound FcεRI for the newly injected MAR-1 to bind and crosslink and hence, no possibility for the newly injected MAR-1 to cause anaphylaxis.

FIG. 58 Anaphylaxis induced by anti-IgE mAb after long-term treatment with MAR-1 anti-FcεRIα mAb is still histamine-mediated. BALB/c mice were treated with 40 µg of MAR-1 or control mAb on days 0, 5, 12, and 18, then injected on day 22 with antihistamine or saline and challenged with anti-IgE mAb. Rectal temperature was determined. Sera obtained 5 min and 4 hr later were assayed for histamine and MMCP1, respectively. Results show that this chronic treatment with MAR-1 considerably, but incompletely suppresses mast cell degranulation and anti-IgE mAb-induced anaphylaxis and that the residual anaphylaxis remains histamine-dependent.

FIG. 59 Chronic MAR-1 anti-FcεRIα mAb treatment completely suppresses antigen-induced IgE-mediated anaphylaxis. BALB/c mice were initially injected with IgE anti-TNP mAb, followed by four 40 µg doses of MAR-1 or control mAb over 21 days. All mice received a second dose of IgE anti-TNP mAb on day 23 and were challenged on day 24 with TNP-OVA. Rectal temperatures were determined. These results indicate that chronic MAR-1 treatment more potently suppresses anti-induced than anti-IgE mAb induced IgE-dependent anaphylaxis. While not desiring to be bound by theory, this may be because MAR-1 greatly decreases the quantity of mast cell associated IgE. This may induce a more limiting situation for antigen-induced anaphylaxis than for anti-IgE mAb-induced anaphylaxis, because antigen can interact only with a small subset of the residual IgE molecules on the mast cell surface, while anti-IgE mAb can interact with all of the residual IgE molecules.

FIG. 60 Rapid desensitization with MAR-1 anti-FcεRIα mAb completely blocks the IL-4 and IL-13 responses to antigen-induced, IgE-dependent anaphylaxis. In the same experiment shown in FIG. 26, IL-4 and IL-13 production were determined by IVCCA for the 4 hr after TNP-OVA challenge. These results are consistent with depletion of basophils (the source of IgE-mediated IL-4 production) and the inability of antigen to trigger IgE-mediated activation of mast cells (the source of IgE-mediated IL-13 production) in these mice. Daggers denote a significant decrease as compared to the control mAb groups.

Figure 26:
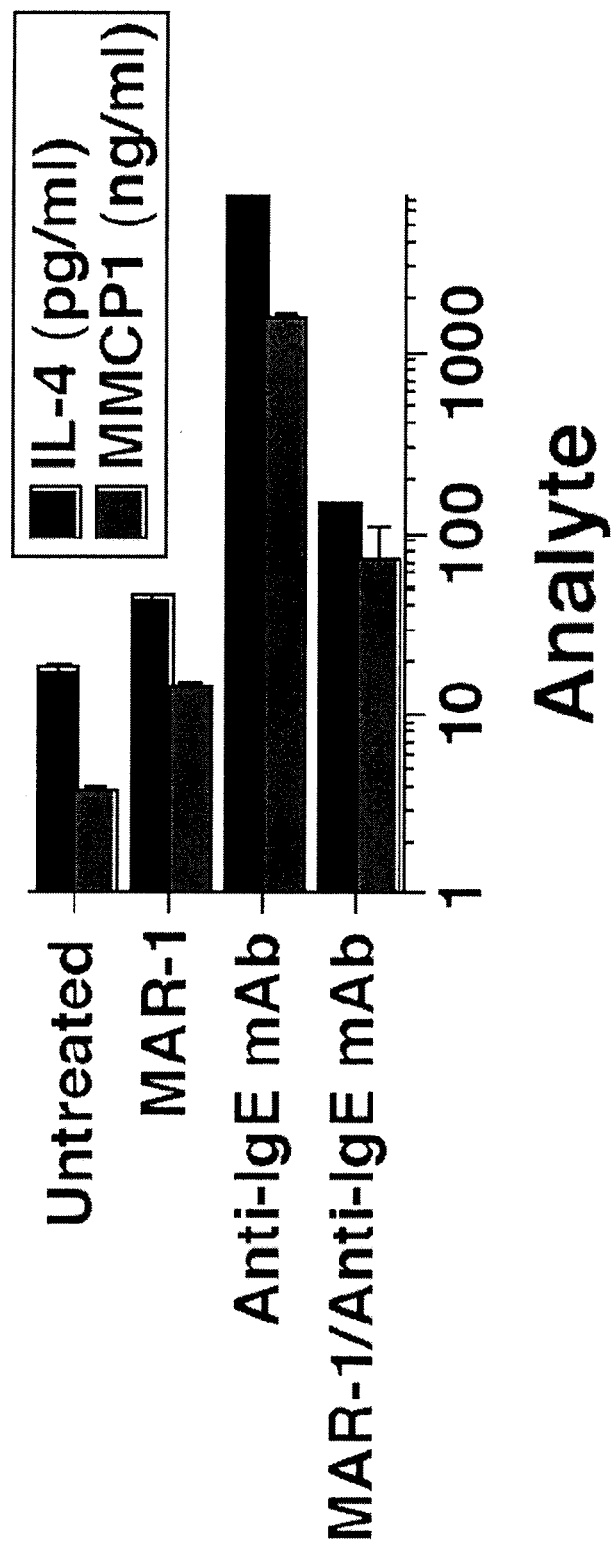
FIG. 26 shows that rapid desensitization with ascending doses of MAR-1 inhibits the IL-4 and MMCP1 responses to anti-IgE mAB two hours later.
Figures 27A, 27B:
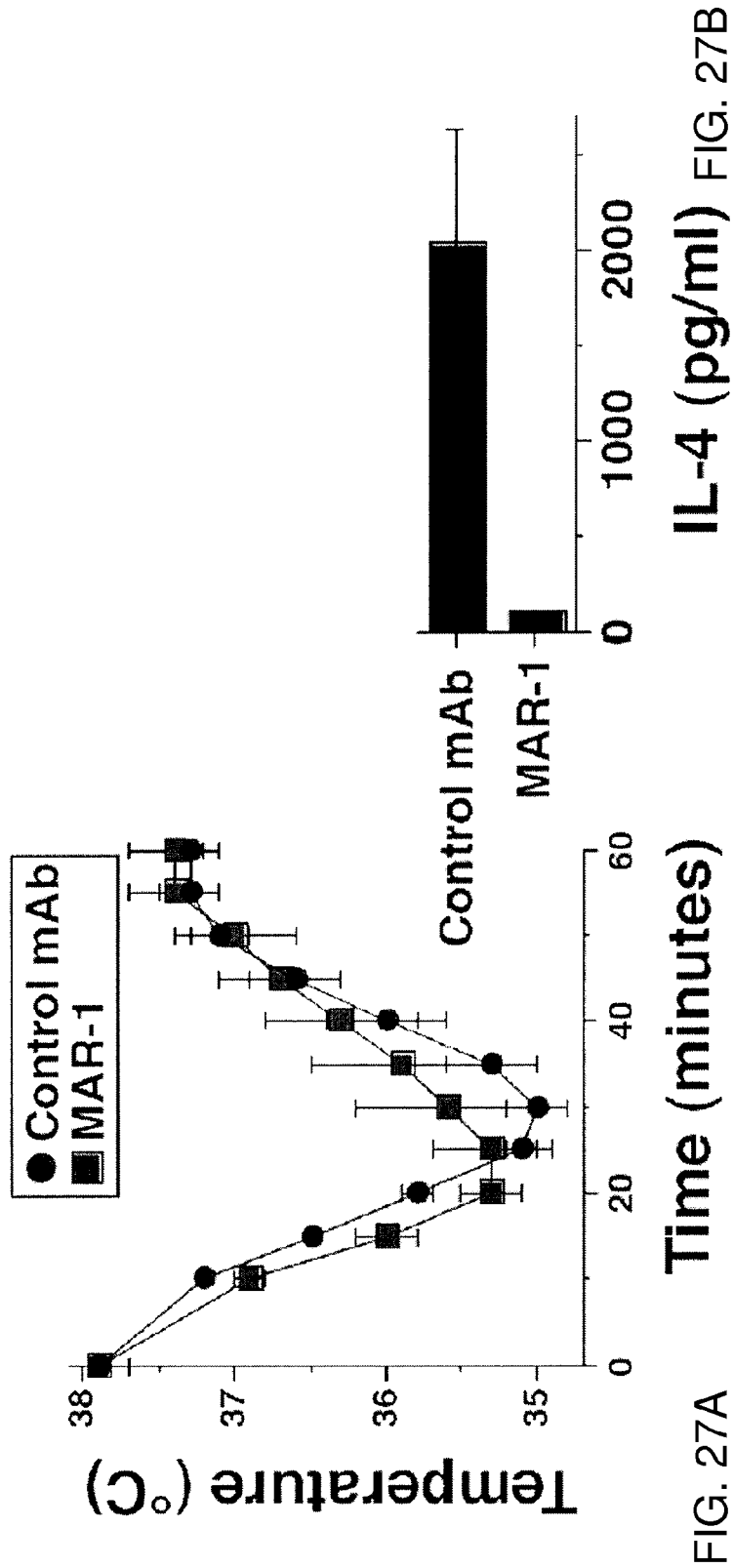
FIG. 27 shows that MAR-1 rapid desensitization fails to suppress the anaphylactic response to Anti-IgE mAB 70 hours later.
Figure 29:
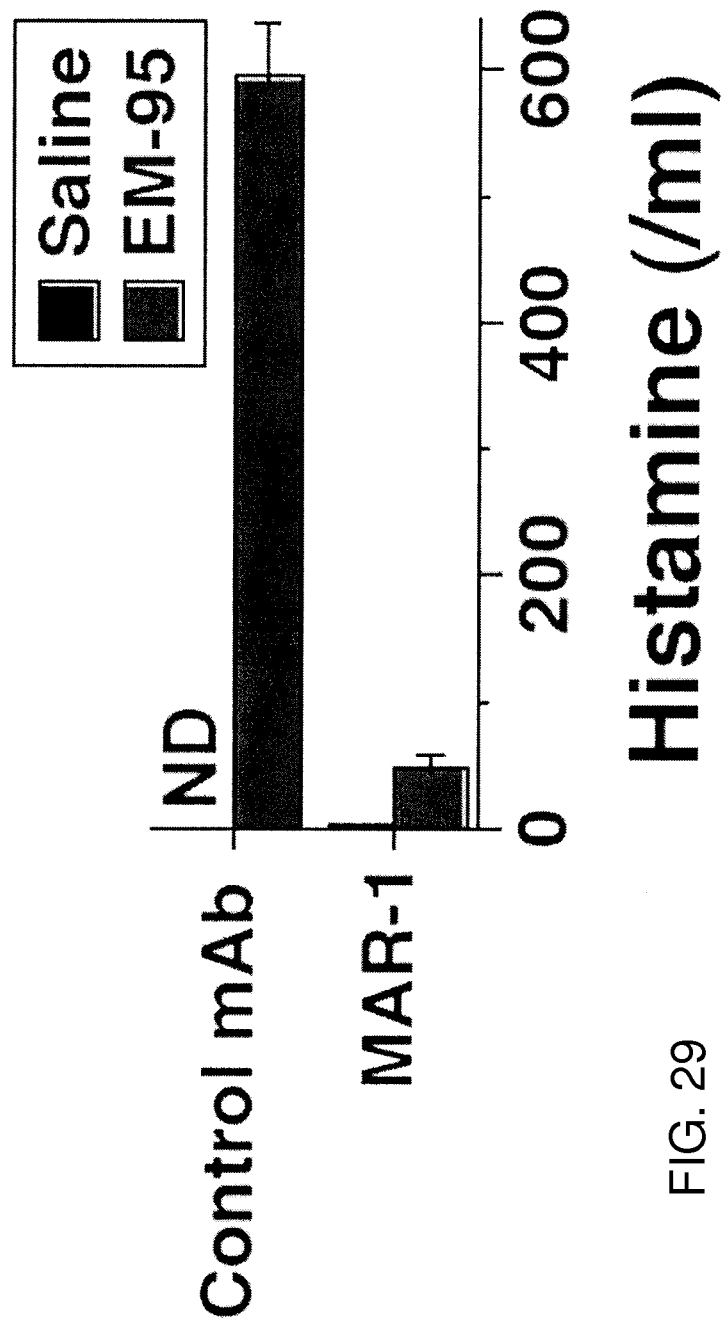
FIG. 29 shows that treatment with MAR-1 for 22 days strongly suppresses the histamine response to anti-IgE mAB.
Figure 30:
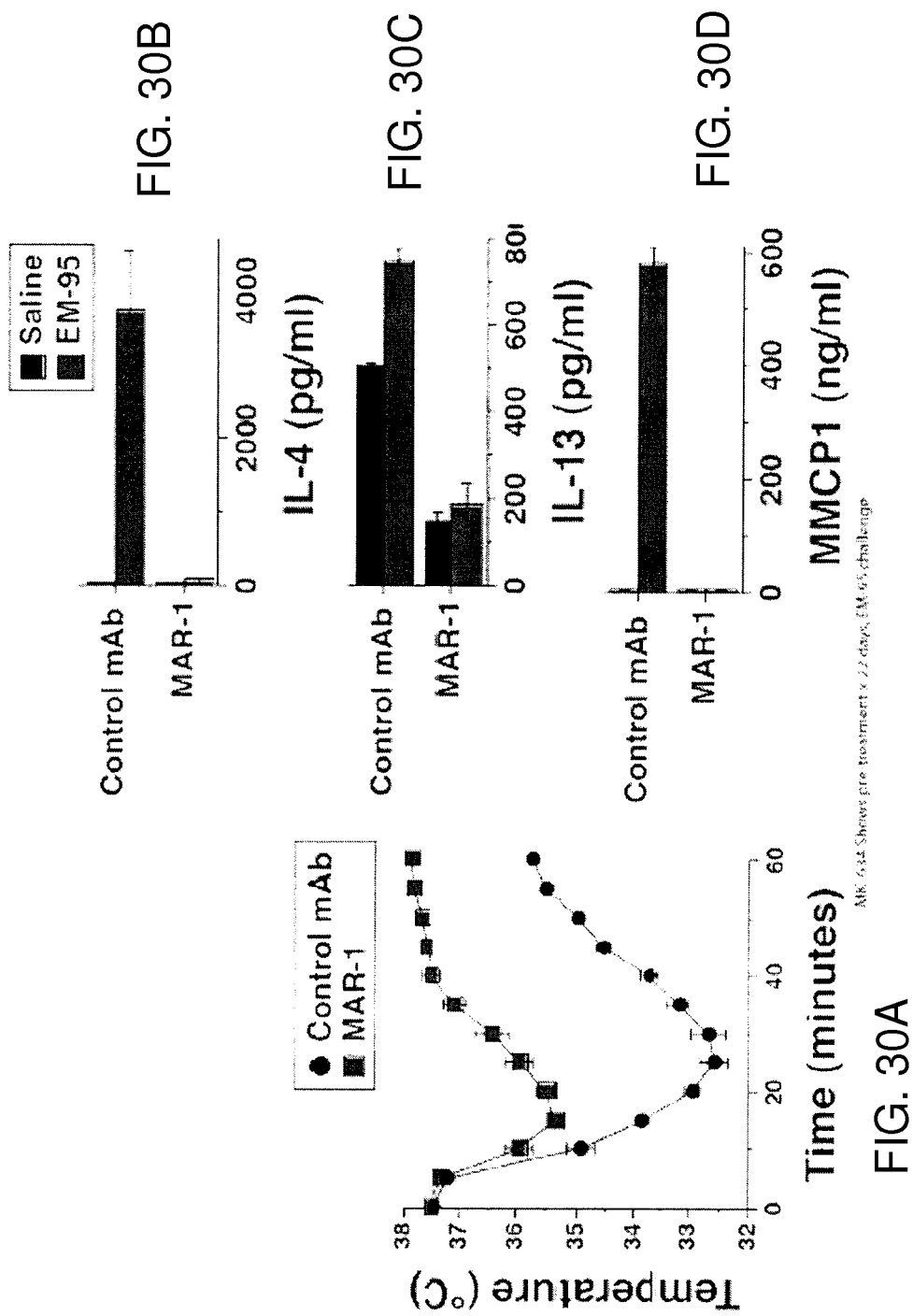
FIG. 30 shows that treatment with MAR-1 for 22 days strongly suppresses the IL-4 (B), IL-13 (C), MMCP1 (D), and anaphylactic (A) responses to anti-IgE mAB.
Figure 31:
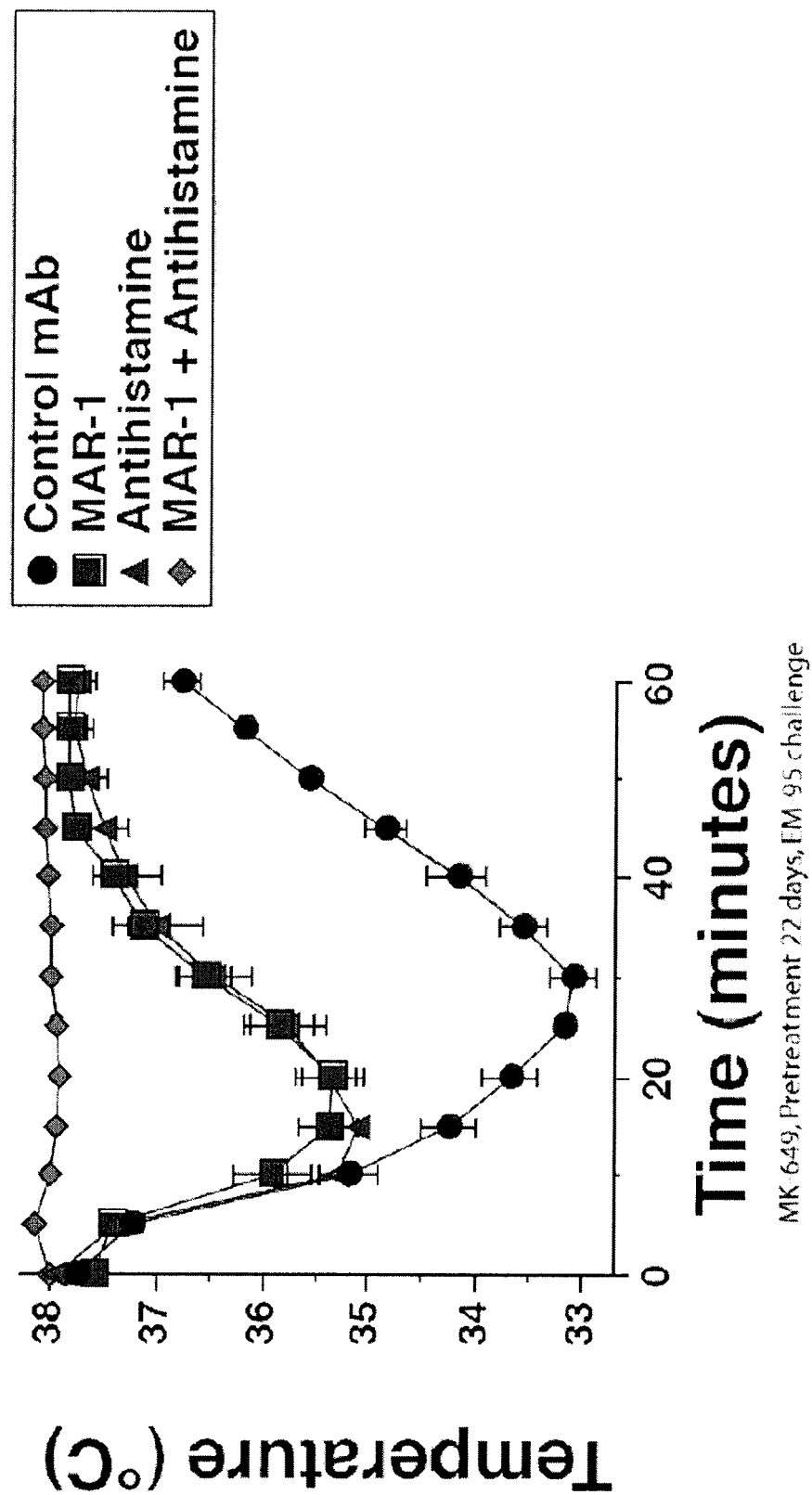
FIG. 31 shows that treatment with MAR-1 for 22 days plus antihistamine completely blocks the anaphylactic response to anti-IgE mAB.
Figure 32:
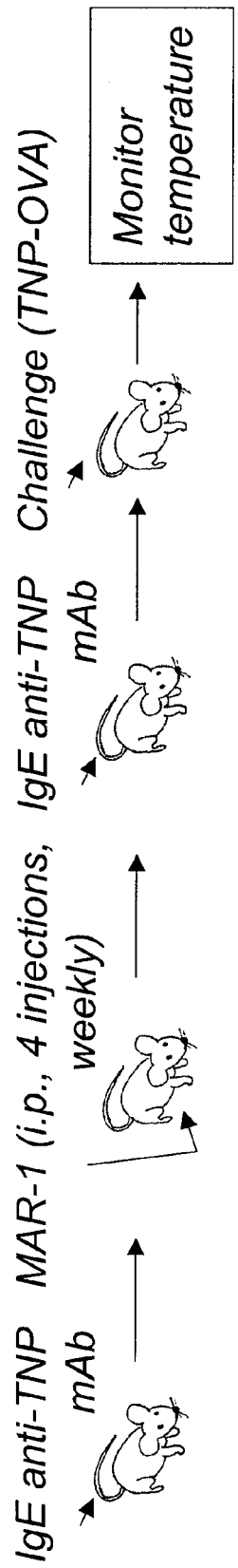
FIG. 32 shows treatment of mice with IgE anti-TNP mAB followed by MAR-1, IgE anti-TNP mAB and TNP-OVA challenge, with temperature monitoring.
Figures 33A, 33B, 33C:
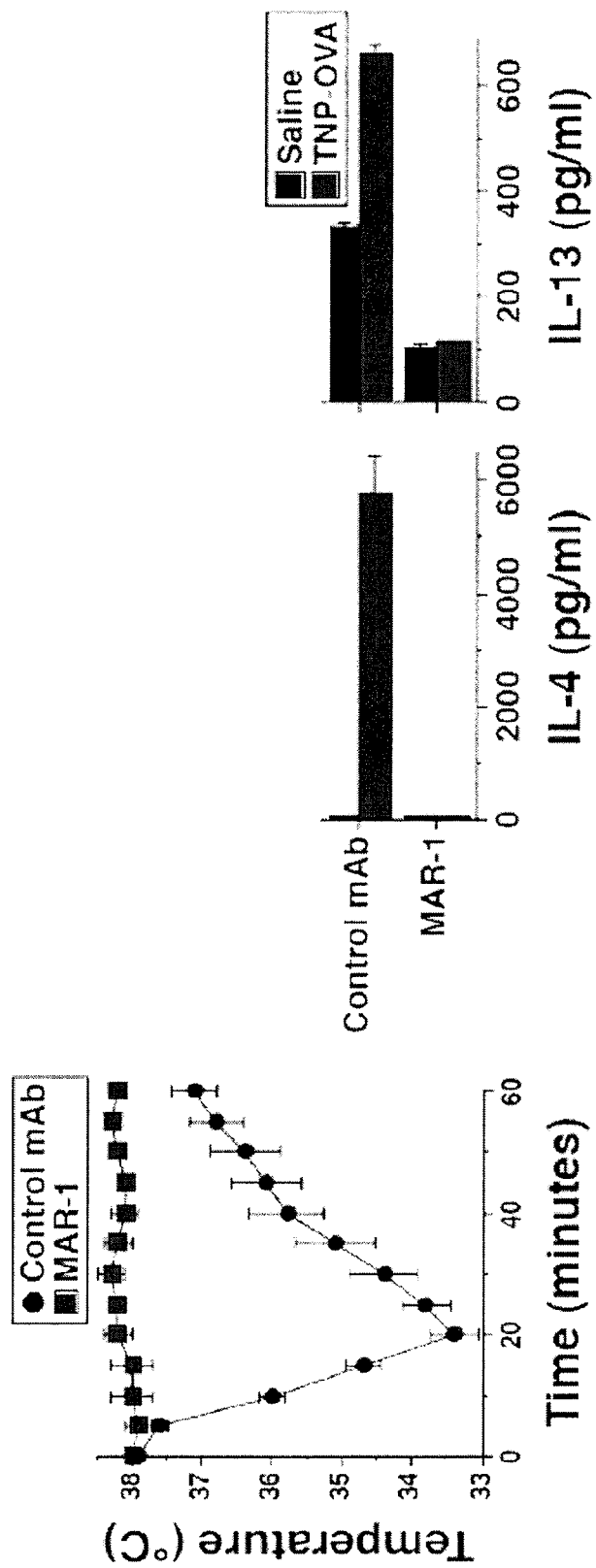
FIG. 33 shows that treatment of IgE anti-TNP-sensitized mice with MAR-1 for 21 days blocks the IL-4 (B), IL-13 (C) and anaphylactic (A) responses to TNP-OVA, despite additional exposure to IgE anti-TNP mAB.
Figure 34:
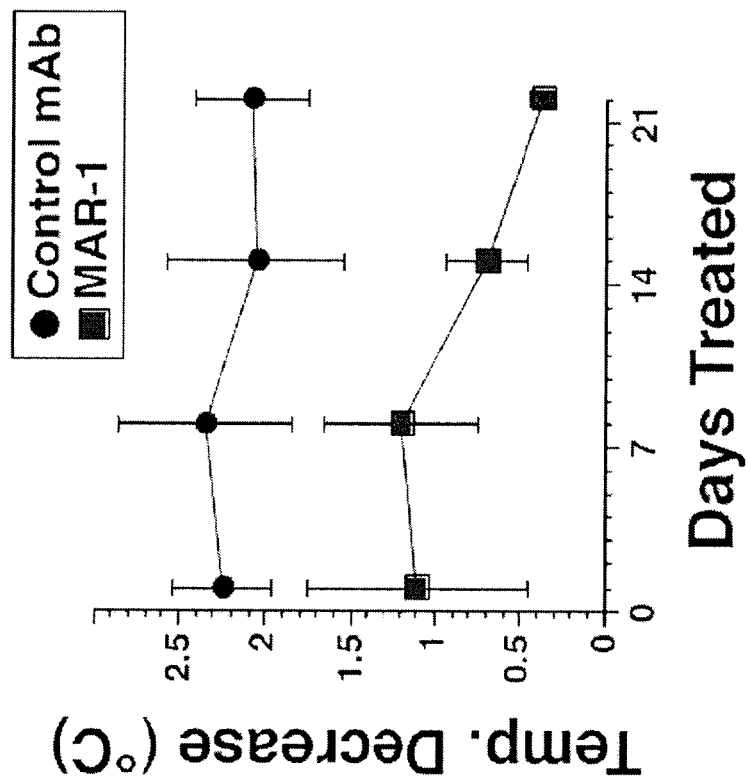
FIG. 34 shows the kinetics of MAR-1 suppression of the anaphylactic response to TNP-OVA in mice primed with IgE anti-TNP mAB.

FIG. 61 MAR-1 anti-FcεRIα mAb blocks IgE-mediated anaphylaxis in mice actively immunized with goat anti-mouse IgD antibody (GaMD). Mice immunized i.p. with goat anti-mouse IgD antiserum were treated i.p. 8 and 12 d later with MAR-1 or control mAb. All mice were injected i.p. 2 d after that with anti-FcRIIb/RIII mAb (to prevent IgG-mediated anaphylaxis) and challenged i.v. with 5 mg of goat IgG. Rectal temperatures and IL-4, IL-13 and MMCP1 secretion were determined. Results demonstrate that MAR-1 can suppress IgE-mediated, antigen-induced anaphylaxis that is primed by active immunization in addition to IgE-mediated anaphylaxis that is primed by passive immunization, as shown in FIG. 26. Double asterisks denote a significant decrease as compared to the control mAb-treated groups.

FIG. 62 Treatment with MAR-1 anti-FcεRIα mAb suppresses IgE-mediated anaphylaxis in mice actively sensitized with ovalbumin (OVA). BALB/c mice were immunized twice i.p. with OVA/alum, then injected i.p. on days 2, 4 and 6 with 40 µg of MAR-1 or control mAb. Mice were injected with 500 µg of 2.4G2 on day 7 and challenged i.v. with 200 µg of OVA the next day. Changes in rectal temperature and IL-4, IL-13 and MMCP1 secretion were determined. These observations provide a second example of the ability of chronic MAR-1 treatment to suppress antigen-induced, IgE-mediated anaphylaxis in actively sensitized mice that have relatively high serum IgE levels.

Figure 63:
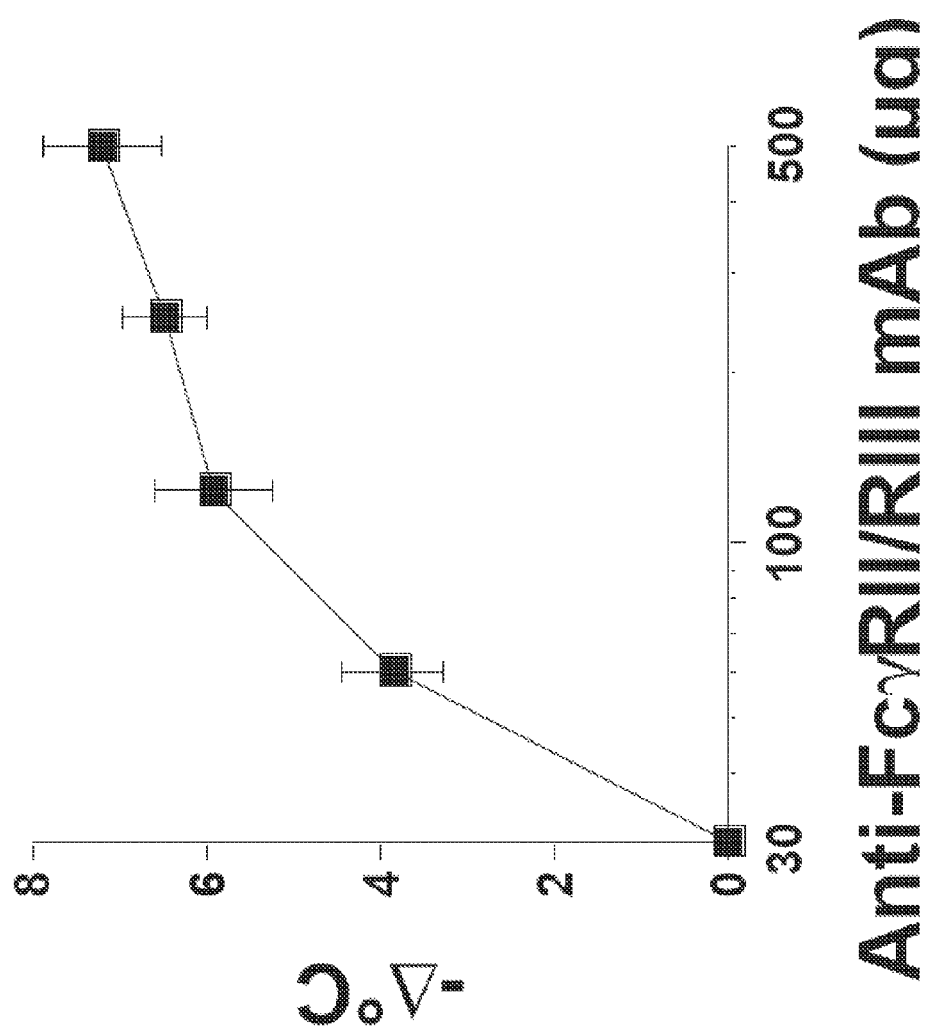
FIG. 63 shows induction of anaphylaxis by 2.4G2 anti-FcγRII/RIII monoclonal antibody

FIG. 63 Induction of anaphylaxis by 2.4G2 anti-FcγRII/RIII mAb. BALB/c mice were injected i.v. with the doses of anti-FcγRIIb/RIII mAb shown. Rectal temperatures were determined. Mean maximum temperature decrease is shown. These observations demonstrate that the crosslinking of FcγRIII can induce anaphylaxis (note that FcγRII is an inhibitory receptor, while FcγRIII is a stimulatory receptor).

FIG. 64 Mice can safely be rapidly desensitized with 2.4G2 anti-FcgRII/RIII mAb. BALB/c mice were IL-4C-pretreated (to make them more sensitive to inducers of anaphylaxis), then rapidly desensitized i.p. hourly with doubling doses of anti-FcRIIb/RIII mAb, starting with a dose of 15 μg. Mean maximum rectal temperature decreases for the 60 min after each injection are shown. Thus, although a single large injection of 2.4G2 induces anaphylaxis, this is prevented by 2.4G2 injection through a rapid desensitization approach.

FIG. 65 Rapid desensensitization with 2.4G2 anti-FcγRII/RIII mAb suppresses antigen-induced anaphylaxis in mice passively sensitized with IgG1 or IgG2a mAb. BALB/c mice were pretreated with IgG1 or IgG2a anti-TNP mAb, then rapidly desensitized with anti-FcγRII/RIII or control mAb (J1.2). Mice were then challenged by i.v. injection of 100 μg of TNP-BSA. Rectal temperatures were determined. These observations indicate that an antibody that binds to FcγRII and FcγRIII is sufficient to suppress IgG-mediated anaphylaxis even though cells implicated in anaphylaxis also express the stimulatory IgG Fc receptors FcγRI and FcγRIV.

Figure 2:
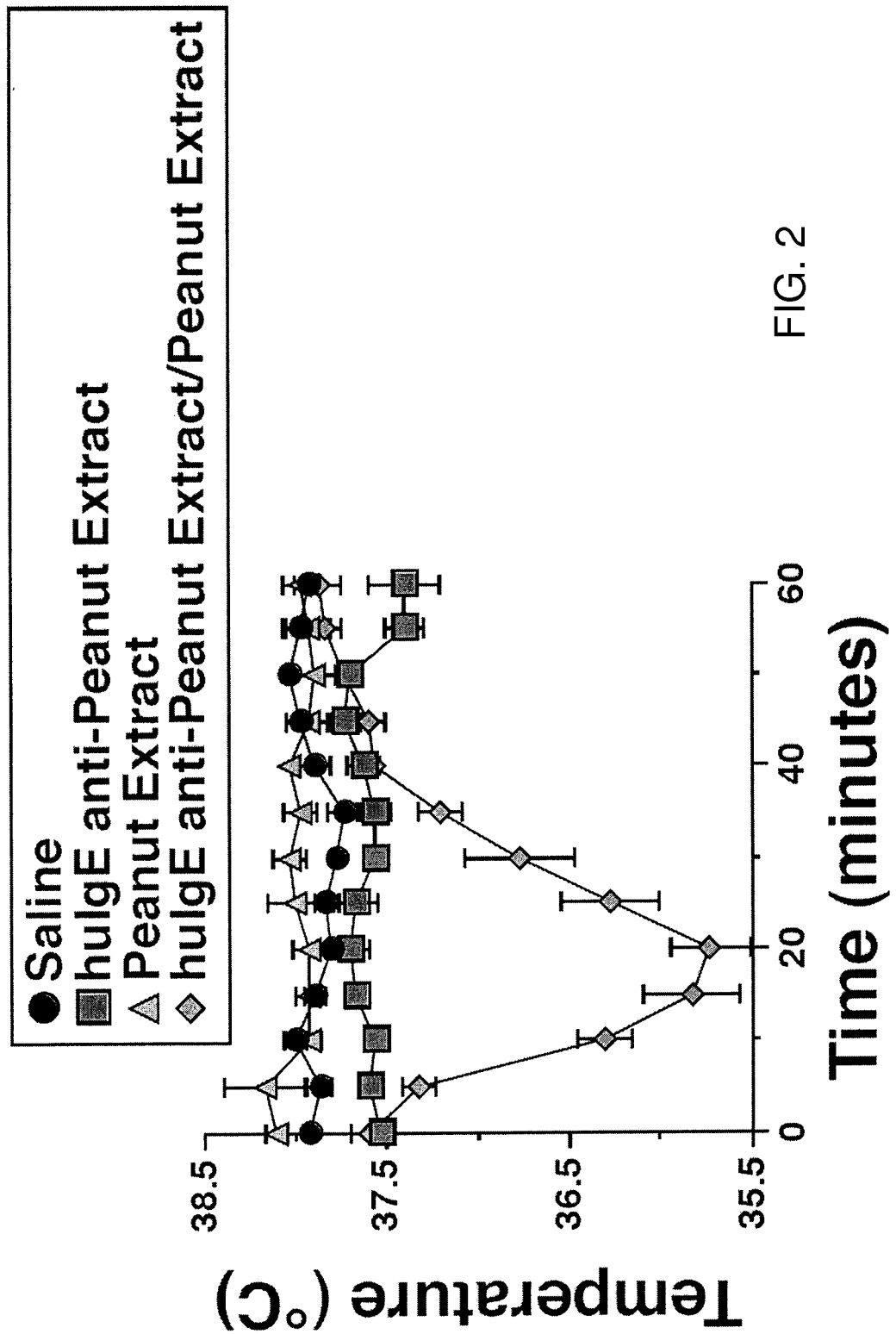
FIG. 2 shows peanut extract induces anaphylaxis in huFcεRIα transgenic mice primed with IgG-depleted serum from a peanut allergic individual and challenged with peanut extract.

FIG. 66 2.4G2 anti-FcγRII/RIII mAb does not block binding of FcγRI or FcγRIV mAb but decreases neutrophil and monocyte expression of these receptors. Left panel: 10⁶ murine blood leukocytes were pelleted, incubated for 30 min at 4° C. in the presence of $NaN_3$ with 1 μg of anti-FcγRII/RIII or control mAb, then stained for FcγRI, FcγRIII, or FcγRIV and analyzed by flow cytometry. Right panel: BALB/c mice were injected with anti-FcγRII/RIII or control mAb. Blood cells obtained 24 hr later were stained for FcγRI, FcγRIIb, FcγRIII, or FcγRIV and analyzed by flow cytometry. These observations indicate that 2.4G2 binds to FcγRI and/or FcγRIV at epitopes that do not inhibit binding with the anti-FcγRI and FcγRIV mAbs used in this experiment, that 2.4G2-ligated FcγRIIb and/or FcγRIII interact with FcγRI and/or FcγRIV in the cell membrane, or that the activation of FcγRIIb and/or FcγRIII by 2.4G2 indirectly effects FcγRI and/or FcγRIV expression. Daggers denote a significant decrease as compared to the control mAb-treated groups. Percentages denote decrease from control mAb-treated groups.

Figures 67A, 67B:
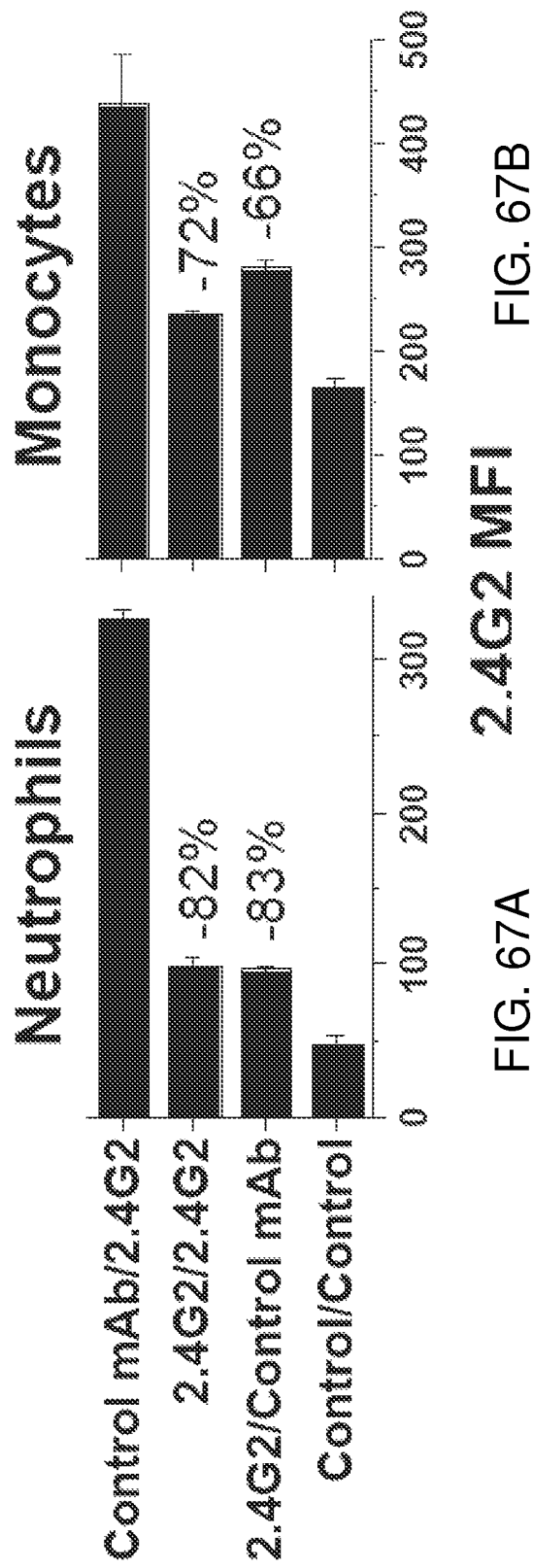
FIGS. 67A-B show that injection of mice with 2.4G2 anti-FcγRII/RIII monoclonal antibody partially removes these receptors from the neutrophil and monocyte cell surface.

FIG. 67 Injection of mice with 2.4G2 anti-FcγRII/RIII mAb partially removes these receptors from the neutrophil and monocyte cell surface. BALB/c WT mice were injected i.p. with 500 μg of biotin-labeled 2.4G2 or control mAb. Blood leukocytes obtained the next day were incubated on ice with biotin-2.4G2 or control mAb, than stained with fluorochrome-labeled streptavidin, as well as with mAbs to identify neutrophils and monocytes. Results show that 2.4G2 partially, but not completely removes FcγRII and/or FcγRIII from the surface of neutrophils and monocytes. Percentages denote decreases as compared to groups initially treated with control mAb.

FIG. 68 Rapid desensitization with 2.4G2 anti-FcγRII/RIII mAb is FcγRII independent. WT and FcγRIIb-deficient mice (FcγRIIb-) were pretreated with IgG2a anti-TNP mAb, then rapidly desensitized with anti-FcγRII/RIII or control mAb or injected with saline and challenged i.v. with TNP-BSA. Rectal temperatures were determined. Data pooled from 2 experiments. †$p<0.05$ for decrease as compared to control. Result show that 2.4G2 rapid desensitization does not require negative signaling through FcγRIIb.

FIG. 69 MAR-1 hamster IgG anti-mouse FcεRIα mAb and GK1.5 rat IgG anti mouse CD4 mAb synergistically suppress established IgE-mediated anaphylaxis that is triggered by antigen ingestion. BALB/c mice were immunized i.p. with OVA alum or egg white/alum, then challenged by oral gavage with OVA or egg white until they developed shock (hypothermia) and diarrhea in response to oral gavage with OVA or egg white. Groups of mice then were treated i.p. with anti-CD4 mAb (a single dose on day 0), MAR-1 (3×/week for day 0 until day 30) and challenged o.g. with OVA or egg white on the days shown (day 0=the start of treatment for mice that had already developed diarrhea and shock in response to OVA or egg white ingestion). Panels show: A) the development of hypothermia in the different groups of mice in response to oral challenge with OVA; B) the development of diarrhea; C) MMCP1 responses; D) the development of mouse IgG1 antibodies to hamster IgG in mice that received MAR-1 plus control mAb or MAR-1+GK1.5; and E) IgG1 anti-OVA responses, IL-4 responses to oral antigen challenge and IL-13 responses to oral antigen challenge at the time points indicated. Overall, these observations demonstrate that: 1) anti-CD 4 mAb enhances the rapidity and extent to which MAR-1 suppresses established IgE-mediated food allergy 2) a single dose of anti-CD4 mAb prevents the development of neutralizing mouse antibody to MAR-1, which otherwise blocks the MAR-1 effect; and 3) the suppressive effect of anti-CD4+ anti-FcεRIα mAb treatment is long lasting.

IV. Conclusions Regarding Selected Data

MAR-1 anti-FcεRIα mAb and IgE each block the binding of the other to mast cell FcεRI. MAR-1 has limited ability to displace IgE that is bound to mast cell FcεRI, either at 4° C. or 37° C., but rapidly internalizes free mast cell FcεRI and appears to increase the turnover rate of mast cell FcεRI that has bound IgE in vivo. Pretreatment with MAR-1 blocks the ability of subsequent treatment with IgE anti-TNP mAb to prime for TNP-OVA-induced anaphylaxis and IL-4 production.

Additionally, in vivo treatment with MAR-1 for 8 days eliminates most, but not all, mast cell IgE and FcεRI. MAR-1 is an activating mAb that induces IL-4 and MMCP1 production, as well as shock. Saturating mast cell FcεRI with IgE prevents MAR-1-induced shock and decreases the ability of MAR-1 to elicit IL-4 production, presumably by preventing MAR-1 binding to FcεRI. Antihistamine and corticosteroid treatment can suppress shock induced by MAR-1 injection.

Also, rapid desensitization with MAR-1 (i.e.; injection of progressively increasing doses of MAR-1, starting with a dose too low to induce shock), allows the eventual injection of large doses of MAR-1 without inducing shock. Rapid desensitization with MAR-1 suppresses anaphylaxis and IL-4 and MMCP1 responses induced by anti-IgE mAb challenge 2 hours after the completion of rapid desensitization. Suppression of mast cell degranulation reflects activation-induced desensitization, as shown by suppression of the mast cell calcium response to FcεRI crosslinking. This type of desensitization is no longer present 48 hours after the completion of rapid desensitization, even in the continued presence of MAR-1. Rapid desensitization with MAR-1 does not suppress the ability of histamine or PAF to induce shock. Rapid desensitization with MAR-1 completely eliminates the ability of subsequent large doses of MAR-1 to induce shock, as long as MAR-1 is still present in serum prior to a subsequent MAR-1 injection.

MAR-1 eliminates basophils, but not mast cells or other inflammatory cell types. MAR-1 gradually induces long-lasting desensitization by removing all or nearly all FcεRI and IgE from mast cells. This occurs even when serum IgE levels are high. Treatment with MAR-1 for 22 days blocks IL-4, IL-13, MMCP1 and shock induced by TNP-OVA challenge of IgE anti-TNP mAb-primed mice. Treatment with MAR-1 for 2-3 weeks blocks IgE-mediated IL-4, IL-13, MMCP1 responses and shock induced by i.v. antigen challenge in mice actively immunized with that antigen. Treatment with MAR-1 for 22 days inhibits mast cell degranulation and shock induced by anti-IgE mAb. Treatment with MAR-1 for 22 days synergizes with antihistamine treatment to completely block the anaphylactic response to anti-IgE mAb.

MAR-1 considerably suppresses established, IgE-mediated food allergy and anti-CD4 mAb synergistically completely suppress IgE-mediated, established food allergy. Injection of a single dose of an antibody (2.4G2) that binds both to a stimulatory FcεR, FcγRIII, and an inhibitory FcγR, FcγRIIb, causes dose-related shock. Rapid desensitization of mice with progressively increasing doses of 2.4G2 prevents the induction of shock by injection of a single large dose of 2.4G2. Rapid desensitization with 2.4G2 prevents IgG-mediated anaphylaxis, regardless of whether anaphylaxis is mediated by IgG1 or IgG2a. In vivo treatment with 2.4G2 blocks the binding of mAbs specific for FcγRIIb or FcγRIII. It also inhibits the binding of a mAb specific for FcγRIV to approximately the same extent that FcγRIIb and FcγRIII are removed from the macrophage cell surface. Rapid desensitization with 2.4G2 is not FcγRIIb-dependent.

Overall, rapid desensitization with MAR-1 anti-FceRIα mAb or 2.4G2 anti-FcgRIIb/RIII mAb can be used in mice to safely suppress IgE- and IgG-mediated allergic reactions, respectively. A similar approach could be used to safely suppress IgE- and IgG-mediated allergic reactions in humans.

In specific embodiments herein described, methods contemplated may comprise one or more of the following (among others): wherein the escalating doses are at least one of doubled or tripled in relation to each immediately preceding dose of the monoclonal antibody; wherein about 8 to about 10 total doses are provided in a single 24 hour period; wherein the doses are administered every about 1 to about 3 hours; wherein the monoclonal antibody is anti-FcγRIIb/RIII; wherein the monoclonal antibody is anti-FceRIα; wherein from 1 to 4 doses of the monoclonal antibody are administered over about 8 days. Other specific embodiments include wherein: the method comprises providing an additional single dose of either anti-FceRIα or anti-FcγRIIb/RIII on each of every 2 to 3 days following the last administration of the sequentially escalating dose of step (c) of claim 1 for a total of about 8 days up to about day 22 (which can be repeated after the injected antibody half-life makes it less effective necessitating reintroduction such as (for example) after three weeks following day 22, and can be indefinitely repeated); wherein the additional single dose is equal to the maximum dose administered in the last administration of the sequentially escalating dose of step (c) of claim 1 from the sequentially escalating doses of monoclonal antibody; wherein approximately 21 days after the last additional single dose, the subject is administered at least one dose of anti-FceRIα or anti-FcγRIIb/RIII; wherein after the last additional single dose, the subject is administered at least one dose of anti-FceRIα or anti-FcγRIIb/RIII at a time interval set so as to match an estimated half-life of either IgG or IgE in relation to the time of the last additional single dose (the at least one dose can be a series of doses at intervals such as every 2-3 days; also the antibody half-life can be estimated or based on known clinical lives; in certain embodiments the half-life of IgE may be considered less than 1 week and the half-life of IgG may be considered from two to four weeks; injections can be made at any time of degradation of the immunoglobulins, such as at an estimated 10-90%); wherein the subject is a human; wherein the allergic reaction is related to a food allergy; wherein the subject is additionally treated with anti CD4 monoclonal antibodies; as well as wherein the subject is additionally treated with an antihistamine or a corticosteroid, or both.

V. Examples

The following are non-limiting examples of various aspects of the methods and models described herein. The examples are given solely for the purpose of illustration and are not to be construed as limiting the invention, as many variations thereof are possible.

EXAMPLE 1

Materials and Methods of Studies Described Herein

Mice

Female BALB/c and C57BL/6 mice were purchased from Taconic (Hudson, N.Y.) and were used at 7-12 wk of age. FVB/N wild-type mice (purchased from Jackson Labs, Bar Harbor, Me.) and IgE-deficient mice on an FVB/N (a gift from Hans Oettgen and Philip Leder, Harvard, Cambridge, Mass.) were bred in our colony. BALB/c background FceRIα-deficient mice (a gift of Jean-Pierre Kinet, Harvard) were bred in our colony. IL-4 transgenic mice on a BALB/c background (a gift of Robert Tepper, Harvard) were bred in our colony and backcrossed >6 generations to C57BL/6 mice.

Antibodies

Monoclonal antibodies or the hybridomas that produce them were obtained from the following sources: 2.4G2 (rat IgG2b anti-mouse FcγRII/RIII mAb (ATCC, Rockville, Md.)), EM-95 (rat IgG2a antimouse IgE (Zelig Eshhar, Weizmann Instititue, Rehovot, Israel)), MAR-1 (hamster antimouse FceRIα mAb (eBioscience, San Diego, Calif.)), 5B11 (rat IgG2a anti-mouse IL-3R mAb; eBioscience), M1/70 (rat IgG2b anti-mouse CD 11b mAb, (ATCC)), 1A8 (rat IgG2a anti-mouse Ly6G mAb (BD Pharmingen)), (DX5, rat IgM anti-mouse CD49b BD Pharmingen), ACK-2 (rat IgG anti-mouse ckit mAb (Richard Grencis, University of Manchester, Manchester, UK)); IGEL 2a (mouse IgE anti-TNP mAb (ATCC)), 1B7.11 (mouse IgG1 anti-TNP mAb (ATCC)); BVD4-1D11(rat IgG2b anti-mouse IL-4 mAb (Robert Coffman, DNAX, Palo Alto, Calif.)); J1.2 (rat IgG2b anti-4-hydroxy-3-nitrophenylacetyl, used as a control mAb (John Abrams, DNAX)); B3B4 (rat IgG2a anti-mouse CD23 (Daniel Conrad, Va. Commonwealth University, Richmond, Va.); x54-5/7.1 (rat IgG anti-mouse FcγRI mAb, eBioscience), K9.361(anti-Ly17.2, a mouse IgG anti-mouse FcγRIIb mAb, a gift of Ulrich Hammerling (Sloan-Kettering, N.Y.), clone 275003 (rat IgG2a anti-mouse FcγRIII (R&D Systems)), and 9F9 (hamster IgG anti-mouse FcγRIV mAb), a gift of Jeffrey Ravetch, Rockefeller University, New York, N.Y.). MAbs produced as ascites in Pristane-primed athymic nude mice were purified as described. A goat antiserum to mouse IgD was produced as described.

Antigens, Pharmaceuticals and Chemicals

Dexamethasone, triprolidine (an H-1-specific antihistamine), histamine, PAF, OVA and BSA were purchased from Sigma. OVA and BSA were labeled with TNP-OSu (Biosearch). pHrodo-SE was purchased from Invitrogen and used to label mAbs as described by the supplier.

Serum Assays: A kit for measuring in vivo IL-4 production by the IVCCA was purchased from Becton-Dickinson. A similar IVCCA for measurement of in vivo IL-13 production injected mice with biotin-labeled 54D1 and coated plates with 53F5 (both mAbs a gift of Abbott Pharmaceuticals, Worcester, Mass.). A kit for measuring serum levels of MMCP1 was purchased from Moredun (Midlothian, Scotland). A kit for measuring serum histamine concentration was purchased from IBL (Hamburg, Germany). IgE was measured by ELISA.

IL-4C

A long-acting complex of IL-4 that dissociates in vivo to release free, biologically active IL-4 was produced by mixing IL-4 (Peprotech) with anti-IL-4 mAb (BVD4-1D11) at a 2:1 molar (1:5 weight) ratio for at least 5 minutes prior to injection.

Detection of Systemic Anaphylaxis

Mice were challenged i.v. with the appropriate antigen, after which body temperature was determined ever 5-15 min with a rectal probe to detect and quantify hypothermia, a sign of shock.

Preparation of Peritoneal Mast Cells

Peritoneal lavage was collected by ip injection of 10 ml of sterile Hanks Buffer with 5% new born calf serum (HN) and plated on 25 cm2 cell culture flasks (Corning) for 2 hrs, 37° C., 5% CO2. Non-adherent cells were collected and washed with HN. Preparation of nucleated blood cells. Blood obtained by tail vein incision was collected in BD microtainers with K2EDTA (BD Bioscience). Red blood cells were lysed with ACK lysis buffer; cells were washed twice with Hanks' buffer, and resuspended in HN plus 0.2% NaN3 (HNA).

Immunofluorescence Staining:

$1 \times 10^6$ cells in 0.1 ml HNA were incubated of 24G2 for 15 min on ice, and then stained with 1 µg each of mAbs to CD49b, IgE, and IL-3R to identify basophils or with mAbs to IgE, c-kit, and IL-3R to identify basophils. Cells were washed twice, fixed with 2% paraformaldehyde and analyzed with a FACScalibur (BD Biosciences). Basophils were also distinguished as having relatively low forward and side scatter while mast cells have very high forward and side scatter.

EXAMPLE 2

Saturation of FcεRI with IgE and Anaphylaxis

FIG. 1 shows in vivo saturation of FcεRI with IgE suppresses the anaphylactic response to MAR-1. More specifically, FIG. 1 shows that anaphylaxis induction by MAR-1 (hamster anti-mouse FcεRI can be prevented by pretreating mice with IgE. The IgE binds to FcεRI without crosslinking it and prevents the binding of MAR-1 to the receptor. As a result, MAR-1 only binds to receptor that is newly synthesized and inserted into the mast cell membrane. This happens too slowly to cause anaphylaxis and should result in desensitization over a period of a few weeks, as MAR-1 slowly replaces IgE on the mast cell and removes FcεRI from the cell surface. Pretreating mice with a univalent Fab of MAR-1 followed by intact MAR-1 mAB can provide benefits Like IgE, the univalent fragment should occupy mast cell FcεRI without crosslinking it, and, therefore, without activating the mast cells. The intact MAR-1 will slowly, over time, replace the MAR-1 univalent fragment on mast cells and remove FcεRI from these cells. This technique could be used to facilitate treatment with other immunomodulating mAbs that are potentially toxic in bivalent (intact antibody) form, such as anti-CD3 monoclonal antibody.

EXAMPLE 3

Transgenic Studies Regarding huFcεRIα and Peanut Allergies

FIG. 2 shows that peanut extract induces anaphylaxis in huFCεRIα transgenic mice primed with IgG-depleted serum from a peanut allergic individual and challenged with peanut extract. More specifically the data shown in FIG. 2 establishes that mast cells in transgenic mice in which mouse FcεRIα has been replaced by human FcεRIα bind human IgE and cause the mice to develop anaphylaxis when desensitized with IgE from a peanut-allergic individual and injected with peanut extract. Mice develop anaphylaxis when injected with anti-human FcεRIα monoclonal antibody. Taken together, observations show that a desensitization approach similar to that used with MAR-1 may be used to eliminate human FcεRI from mast cells and prevent antigen-specific anaphylaxis that is mediated by human IgE.

EXAMPLE 4

Rapid Desensitization with an Activating Anti-IgE mAb

Rapid desensitization with an activating anti-IgE mAb is described in FIG. 36. In 3 separate experiments, BALB/c mice (4/group in this and other figures) that had been injected with 10 µg of IgE anti-TNP mAb were treated every 90 min with doubling or tripling doses of anti-IgE mAb (EM-95), starting with 50 ng, then challenged the next day i.v. with 10 µg of TNP-BSA or TNP-OVA. Rectal temperatures were determined during the 60 min after the 10 µg challenge. Means of maximum decreases in temperature±SEs are shown. B. In the same 3 experiments, BALB/c mice were serially injected i.v. every 90 min with doses of EM-95 that were 2-3-fold higher than the preceding dose, starting at a dose of 50 ng. The lowest temperature after each dose is shown. Additional experiments that varied dose number and dose increment did not reliably avoid temperature drops >0.5° C. * signifies p<0.05 as compared to mice desensitized with control mAb. † signifies p<0.05 compared to temperature of unchallenged mice.

EXAMPLE 5

Anti-FcεRIα mAb Induces Anaphylaxis that can be Blocked by Rapid Desensitization or Antihistamine Plus Corticosteroid Pretreatment Anti-FcεRIα mAb induces anaphylaxis that can be blocked by rapid desensitization or antihistamine plus corticosteroid pretreatment (see FIGS. 37-42). BALB/c mice were injected i.v. with 50 µg of hamster anti-mouse FcεRIα mAb (MAR-1) or a hamster IgG control mAb (panels A, B and F) or the doses of these mAbs shown (panels C, D and E). Rectal temperature was followed for 45 min (A). MMCP1 in serum 4 hr after mAb injection (B) and histamine in serum 5 min after mAb injection (C) were determined by ELISA. IL-4 secretion during the 4 hr after mAb injection (D) was determined by IVCCA. E. Mice were serially injected i.p. every 60-90 min with the doses of MAR-1 or control mAb shown, starting with 100 ng. The mean maximum decrease in temperature±SE during the 60 min after each injection is shown. F. BALB/c mice were pretreated with IL-4C and injected i.p. the next day at 90 min intervals with doubling doses of MAR-1, starting with 50 ng. Rectal temperatures were determined for 60 min following each injection. Mean maximum decreases from baseline±SE are shown. G. Mice were injected i.v. with a single dose of MAR-1 45 minutes after pretreatment with saline, antihistamine (triprolidine), dexamethasone, or antihistamine+dexamethasone. Rectal temperatures were determined during the subsequent 60 min. * signifies p<0.05 for increase from control; † signifies p<0.05 for increase from 10 µg dose.

EXAMPLE 6

Mechanism of MAR-1 Rapid Desensitization

The mechanism of MAR-1 rapid desensitization has been studied using data from FIGS. 46-49 and 51. A. Peritoneal mast cells from IgE deficient mice were incubated on ice with IgE αTNP mAb or control mAb, then stained for IgE (upper bars) or incubated on ice with MAR-1 and stained for hamster IgG (lower bars). Cells were analyzed for surface fluorescence. B. WT and FcεRIα-mice were injected i.v. with saline or mouse IgE, then challenged i.v. with MAR-1. Rectal temperatures were determined. C. IL-4 secretion was determined by IVCCA for 4 hr following MAR-1 challenge. D. Peritoneal mast cells from wild-type BALB/c mice were cultured for 1 hr at 4° C. or 37° C. with MAR-1 or control mAb, then stained for IgE and analyzed by flow cytometry. E. BALB/c mice were injected i.v. with 10 µg of IgE anti-TNP mAb, then rapidly desensitized with MAR-1 or control mAb. Mice were injected i.v. with TNP-OVA or EM-95 2 hr after the last MAR-1 or control mAb dose. Rectal temperatures were determined. F. BALB/c mice were left untreated or were desensitized with MAR-1. Some mice were injected i.v. 2 hr after the last MAR-1 dose with anti-IgE mAb. Serum MMCP1 and IL-4 production were evaluated. G. BALB/c mice were rapidly desensitized with MAR-1 or control mAb and injected daily i.p. with MAR-1 or control mAb for 2 days, then injected i.v. with anti-IgE mAb. Rectal temperatures were determined. H. BALB/c mice were left untreated or MAR-1 desensitized, then injected i.v. with 3.5 mg of histamine or 500 ng of PAF. Rectal temperatures were determined. *p <0.05 for increase as compared to control; †p<0.05 for decrease as compared to control.

EXAMPLE 7

Effects of Anti-FcεRIα mAb on Basophil Number and Mast Cell IgE Expression

The effects of anti-FcεRIα mAb on basophil number and mast cell IgE expression have been studies herein (see FIGS. 54-56). WT, IL-4 transgenic and OVA-immune mice were left untreated or injected i.v. with MAR-1. Peritoneal mast cells obtained prior to or 1 or 4 days after MAR-1 injection were stained for IgE and analyzed by flow cytometry. Peripheral blood was analyzed for percent basophils. B. C57BL/6 wild-type and TG.UG mice were bled at age 8 weeks and serum IgE levels were determined by ELISA. C. BALB/c peritoneal mast cells were incubated on ice with pHRhodo-labeled MAR-1 or control mAb. Mice were injected i.v. with the same mAbs and peritoneal mast cells were obtained 3 hr later. Cells were analyzed by flow cytometry. D. IgE-deficient mice were injected i.v. with anti-CD23 mAb, then with IgE anti-TNP mAb. The next day, mice were injected with MAR-1 or control mAb. Peritoneal mast cells obtained prior to or 1 or 4 days after MAR-1 or control mAb injection were analyzed for membrane IgE. E. Mice were injected with MAR-1 or control mAb on days 0, 2, 4 and 6. Peritoneal mast cells obtained on day 8 were incubated at 4° C. with no mAb, MAR-1 or IgE anti-TNP mAb, and assayed for IgE and hamster IgG. *p<0.05 for increase as compared to control; †p<0.05 for decrease as compared to control. **p<0.05 for decrease as compared to control mAb-treated mice.

EXAMPLE 8

Suppression of Anaphylaxis by Anti-FcεRIα mAb

Suppression of anaphylaxis by anti-FcεRIα mAb has been studied herein (see FIGS. 58-61). A. Mice were treated with MAR-1 or control mAb on days 0, 5, 12, and 18, then injected on day 22 with antihistamine or saline and challenged with anti-IgE mAb. Rectal temperature was determined. Sera obtained 5 min and 4 hr later were assayed for histamine and MMCP1, respectively. B. BALB/c mice were initially injected with IgE anti-TNP mAb, followed by 4 doses of MAR-1 or control mAb over 21 days. All mice received a second dose of IgE anti-TNP mAb on day 23 and were challenged on day 24 with TNP-OVA (left panel) or either saline or TNP-OVA (right panels). Rectal temperatures and IL-4 and IL-13 secretion were determined. C. Mice immunized i.p. with goat anti-mouse IgD antiserum were treated i.p. 8 and 12 d later with MAR-1 or control mAb. All mice were injected i.p. 2 d after that with anti-FcγRIIb/RIII mAb and challenged i.v. with 5 mg of goat IgG. Rectal temperatures and IL-4, IL-13 and MMCP1 secretion were determined. D. BALB/c mice (8/group) were immunized i.p. with OVA/alum on d 0 and 14 and inoculated i.p. with 60 µg of MAR-1 or control mAb on d 16, 18 and 20 and 500 µg of anti-FcγRII/RIII mAb on d 21. Mice were challenged i.v. with 200 µg of OVA on d 22 and rectal temperatures, IL-4 and MMCP1 secretion were determined. *p<0.05 for increase as compared to control; †p<0.05 for decrease as compared to control. **p<0.05 for decrease as compared to control mAb-treated mice.

EXAMPLE 9

Rapid Desensitization with Anti-FcγR mAb

Rapid desensitization with anti-FcγR mAb has been studies herein (See FIGS. 63-66 and 68). Mice were injected i.v. with anti-FcγRIIb/RIII mAb. Rectal temperatures were determined. Mean maximum temperature decrease is shown. B. IL-4C-pretreated mice were rapidly desensitized i.p. hourly with doubling doses of anti-FcγRIIb/RIII mAb, starting with a dose of 15 µg. Mean maximum rectal temperature decreases for the 60 min after each injection are shown. C. BALB/c mice were pretreated with IgG1 or IgG2a anti-TNP mAb, then rapidly desensitized as in "A" with anti-FcγRII/RIII or control mAb (J1.2). Mice were then challenged by i.v. injection of 100 µg of TNP-BSA. Rectal temperatures were determined. D. Left panels: 106 murine blood leukocytes were pelleted, incubated for 30 min at 4° C. in the presence of NaN3 with 1 µg of anti-FcγRII/RIII or control mAb, then stained for FcγRI, FcγRIIb, FcγRIII, or FcγRIV and analyzed by flow cytometry. Right panels: BALB/c mice were injected with anti-FcγRII/RIII or control mAb. Blood cells obtained 24 hr later were stained for FcγRI, FcγRIIb, FcγRIII, or FcγRIV and analyzed by flow cytometry. E. WT and FcγRIIb-deficient mice (FcγRIIb-) were pretreated with IgG2a anti-TNP mAb, then rapidly desensitized with anti-FcγRII/RIII or control mAb or injected with saline and challenged i.v. with TNP-BSA. Rectal temperatures were determined. Data pooled from 2 experiments. †p<0.05 for decrease as compared to control.

The invention claimed is:

1. A method of treating a subject suffering from an allergic disorder, the method comprising inducing rapid desensitization to an allergen, said rapid desensitization effectuated by:
   a. providing a monoclonal antibody selected from the group consisting of anti-FcεRIa and an antibody that specifically binds FcγRIIb and FcγRIII;
   b. administering the monoclonal antibody to the subject at a dose that is lower than a level required to induce shock; and
   c. administering sequentially escalating doses of the monoclonal antibody, wherein 8 to 10 total doses are administered in a single 24 hour period, thereby inducing rapid desensitization to the allergen.

2. The method of claim 1 wherein the escalating doses are at least one of doubled or tripled in relation to each immediately preceding dose of the monoclonal antibody.

3. The method of claim 1 wherein the doses are administered every 1 to 3 hours.

4. The method of claim 1 wherein the monoclonal antibody is an antibody that specifically binds FcγRIIb and FcγRIII.

5. The method of claim 1 wherein the monoclonal antibody is anti-FcεRIα.

6. The method of claim 1 further comprising providing an additional single dose of either anti-FcεRIα or the antibody that specifically binds FcγRIIb and FcγRIII on each of every 2 to 3 days following a last administration of the sequentially escalating dose of step (c) of claim 1 for a total of about 8 days up to about day 22.

7. The method of claim 6 wherein the additional single dose is equal to the maximum dose administered in the last administration of the sequentially escalating dose of step (c) of claim 1 from the sequentially escalating doses of monoclonal antibody.

8. The method of claim 6 wherein approximately 21 days after the last additional single dose, the subject is administered at least one dose of anti-FcεRIα or the antibody that specifically binds FcγRIIb and FcγRIII.

9. The method of claim 6 wherein after the last additional single dose, the subject is administered at least one dose of anti-FcεRIα or the antibody that specifically binds FcγRIIb and FcγRIII at a time interval set so as to match an estimated immunoglobulin (Ig) half-life of IgG in relation to the time of the last additional dose.

10. The method of claim 1 wherein the subject is a human.

11. The method of claim 1 wherein the allergic disorder is an allergic reaction to a food.

12. The method of claim 1 wherein the subject is additionally treated with anti-CD4 monoclonal antibodies.

13. The method of claim 1 wherein the subject is additionally treated with an antihistamine or a corticosteroid, or both.

14. The method of claim 13 wherein the subject is treated with both the antihistamine and the corticosteroid.

15. The method of claim 11 wherein the suppressing of the allergic reaction comprises the suppressing of a peanut allergy reaction.

16. The method of claim 11 wherein the food comprises a protein.

17. The method of claim 1 wherein the allergen is selected from the group consisting of protein, food, pollen, mold spores, dust, animal dander, insect debris, blood serum, drugs, cosmetics, and combinations thereof.

* * * * *